United States Patent
Mantri et al.

(10) Patent No.: US 12,089,907 B2
(45) Date of Patent: Sep. 17, 2024

(54) ROBOTIC ARMS AND METHODS FOR TISSUE RESECTION AND IMAGING

(71) Applicant: PROCEPT BioRobotics Corporation, Redwood City, CA (US)

(72) Inventors: Surag Mantri, East Palo Alto, CA (US); Nikolai Aljuri, Hillsborough, CA (US); Kevin Patrick Staid, Lowell, MA (US); Jason Hemphill, Los Gatos, CA (US); Keegan Mik, San Francisco, CA (US); Alex Hsia, San Jose, CA (US)

(73) Assignee: PROCEPT BioRobotics Corporation, San Jose, CA (US)

( * ) Notice: Subject to any disclaimer, the term of this patent is extended or adjusted under 35 U.S.C. 154(b) by 0 days.

(21) Appl. No.: 16/940,100

(22) Filed: Jul. 27, 2020

(65) Prior Publication Data

US 2020/0360100 A1   Nov. 19, 2020

Related U.S. Application Data

(63) Continuation of application No. PCT/US2020/021756, filed on Mar. 9, 2020.
(Continued)

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/25* (2016.02); *A61B 34/74* (2016.02);
(Continued)

(58) Field of Classification Search
CPC ........ A61B 17/320016; A61B 1/00149; A61B 1/015; A61B 2017/00725;
(Continued)

(56) References Cited

U.S. PATENT DOCUMENTS

| 4,389,071 A | 6/1983 | Johnson, Jr. |
| 4,561,798 A | 12/1985 | Elcrin |

(Continued)

FOREIGN PATENT DOCUMENTS

| CN | 101394877 | 3/2009 |
| CN | 102905633 | 1/2013 |

(Continued)

OTHER PUBLICATIONS

Lim et al., "Robotic Transrectal Ultrasound-Guided Prostate Biopsy", IEEE Trans Biomed Eng, published online Jan. 7, 2019 (Year: 2019).*
(Continued)

*Primary Examiner* — Christopher L Cook
(74) *Attorney, Agent, or Firm* — FisherBroyles, LLP; John K. Shimmick

(57) ABSTRACT

A system for treating a target tissue of a patient comprises a first robotic arm coupled to a treatment probe for treating the target tissue of the patient, and a second robotic arm coupled to an imaging probe for imaging the target tissue of the patient. The system further comprises one or more computing devices operably coupled with the first robotic arm and the second robotic arm, the one or more computing devices configured to execute instructions for controlling movement of one or more of the first robotic arm or the second robotic arm.

17 Claims, 33 Drawing Sheets

Related U.S. Application Data

(60) Provisional application No. 62/933,793, filed on Nov. 11, 2019, provisional application No. 62/814,966, filed on Mar. 7, 2019.

(51) Int. Cl.
| | |
|---|---|
| A61B 1/00 | (2006.01) |
| A61B 1/015 | (2006.01) |
| A61B 5/055 | (2006.01) |
| A61B 6/00 | (2006.01) |
| A61B 8/12 | (2006.01) |
| A61B 17/32 | (2006.01) |
| A61B 34/30 | (2016.01) |
| A61B 90/00 | (2016.01) |
| A61B 90/57 | (2016.01) |

(52) U.S. Cl.
CPC .......... *A61B 1/00149* (2013.01); *A61B 1/015* (2013.01); *A61B 5/055* (2013.01); *A61B 6/487* (2013.01); *A61B 8/12* (2013.01); *A61B 17/320016* (2013.01); *A61B 2034/301* (2016.02); *A61B 2034/303* (2016.02); *A61B 2090/065* (2016.02); *A61B 2090/571* (2016.02)

(58) Field of Classification Search
CPC .... A61B 2034/2048; A61B 2034/2055; A61B 2034/2059; A61B 2034/2065; A61B 2034/301; A61B 2034/303; A61B 2090/065; A61B 2090/378; A61B 2090/571; A61B 2217/005; A61B 2217/007; A61B 34/20; A61B 34/25; A61B 34/30; A61B 34/37; A61B 34/74
See application file for complete search history.

(56) References Cited

U.S. PATENT DOCUMENTS

| | | | |
|---|---|---|---|
| 4,932,956 A | 6/1990 | Reddy | |
| 5,876,325 A | 3/1999 | Mizuno | |
| 6,039,695 A | 3/2000 | Sakamoto | |
| 6,331,181 B1 | 12/2001 | Tierney | |
| 6,338,714 B1 | 1/2002 | Krause | |
| 6,375,635 B1 | 4/2002 | Moutafis | |
| 7,021,173 B2 | 4/2006 | Stoianovici | |
| 7,882,841 B2 | 2/2011 | Aljuri | |
| 8,062,246 B2 | 11/2011 | Moutafis | |
| 8,152,816 B2 | 4/2012 | Tuma | |
| 8,229,188 B2 | 7/2012 | Rusko | |
| 8,398,541 B2 | 3/2013 | Dimaio | |
| 8,660,635 B2 | 2/2014 | Simon | |
| 8,814,921 B2 | 8/2014 | Aljuri | |
| 8,827,948 B2 | 9/2014 | Romo | |
| 8,961,533 B2 | 2/2015 | Stahler | |
| 9,072,452 B2 | 7/2015 | Vayser | |
| 9,144,461 B2 | 9/2015 | Kruecker | |
| 9,277,969 B2 | 3/2016 | Brannan | |
| 9,314,306 B2 | 4/2016 | Yu | |
| 9,364,251 B2 | 6/2016 | Aljuri | |
| 9,610,131 B2 | 4/2017 | Stoianovici | |
| 9,737,371 B2 | 8/2017 | Romo | |
| 9,867,635 B2 | 1/2018 | Alvarez | |
| 9,877,788 B2 | 1/2018 | Stoianovici | |
| 10,130,427 B2 | 11/2018 | Tanner | |
| 10,226,298 B2 | 3/2019 | Ourselin | |
| 10,231,867 B2 | 3/2019 | Alvarez | |
| 10,307,214 B2 | 6/2019 | Lathrop | |
| 10,423,757 B2 | 9/2019 | Kruecker | |
| 10,441,371 B2 | 10/2019 | Hendrick | |
| 10,448,956 B2 | 10/2019 | Gordon | |
| 10,555,780 B2 | 2/2020 | Tanner | |
| 10,555,785 B2 | 2/2020 | Yeung | |
| 10,646,295 B2 | 5/2020 | Stoianovici | |
| 10,779,897 B2 | 9/2020 | Rockrohr | |
| 11,071,601 B2 | 7/2021 | Staid | |
| 11,096,753 B1 | 8/2021 | Mantri | |
| 11,278,451 B2 | 3/2022 | Andrews | |
| 11,357,586 B2 | 6/2022 | Huang | |
| 11,590,319 B2 | 2/2023 | Debuys | |
| 11,771,512 B2 | 10/2023 | Mantri | |
| 2002/0121577 A1 | 9/2002 | Metelski | |
| 2004/0024311 A1* | 2/2004 | Quaid, III | A61B 34/10 600/428 |
| 2004/0034282 A1* | 2/2004 | Quaid, III | A61B 34/70 600/300 |
| 2004/0230211 A1 | 11/2004 | Moutafis | |
| 2006/0118495 A1 | 6/2006 | Kondratalv | |
| 2006/0142657 A1* | 6/2006 | Quaid | A61B 17/1703 600/424 |
| 2006/0205996 A1 | 9/2006 | Presthus | |
| 2008/0009747 A1 | 1/2008 | Saadat | |
| 2008/0027420 A1 | 1/2008 | Wang | |
| 2009/0227998 A1 | 9/2009 | Aljuri | |
| 2009/0306692 A1 | 12/2009 | Barrington | |
| 2009/0326489 A1 | 12/2009 | Kensy | |
| 2010/0010524 A1 | 1/2010 | Barrington | |
| 2010/0036245 A1 | 2/2010 | Yu | |
| 2011/0184391 A1 | 7/2011 | Aljuri | |
| 2011/0282356 A1 | 11/2011 | Solomon | |
| 2012/0035462 A1 | 2/2012 | Maurer, Jr. | |
| 2012/0071894 A1 | 3/2012 | Tanner | |
| 2012/0095498 A1 | 4/2012 | Stefanchik | |
| 2013/0218186 A1 | 8/2013 | Dubois | |
| 2013/0239392 A1 | 9/2013 | Solomon | |
| 2014/0039314 A1 | 2/2014 | Stoianovici | |
| 2014/0094968 A1* | 4/2014 | Taylor | B25J 13/006 700/257 |
| 2014/0142438 A1 | 5/2014 | Ludwin | |
| 2014/0194896 A1* | 7/2014 | Frimer | A61B 1/00009 606/130 |
| 2014/0309649 A1 | 10/2014 | Alvarez | |
| 2015/0025539 A1 | 1/2015 | Alvarez | |
| 2015/0080907 A1 | 3/2015 | Herrell | |
| 2015/0088107 A1 | 3/2015 | Aljuri | |
| 2015/0173726 A1 | 6/2015 | Lohmeier | |
| 2015/0366546 A1 | 12/2015 | Kamen | |
| 2016/0067450 A1 | 3/2016 | Kowshik | |
| 2016/0100898 A1 | 4/2016 | Jinno | |
| 2016/0143778 A1 | 5/2016 | Aljuri | |
| 2016/0262827 A1 | 9/2016 | Ross | |
| 2016/0302653 A1 | 10/2016 | Inoue | |
| 2017/0014269 A1 | 1/2017 | Draheim | |
| 2017/0105785 A1 | 4/2017 | Shelton, IV | |
| 2017/0189127 A1 | 7/2017 | Weir | |
| 2017/0202537 A1* | 7/2017 | Ippolito | A61B 5/4381 |
| 2017/0245878 A1 | 8/2017 | Aljuri | |
| 2017/0245949 A1 | 8/2017 | Randle | |
| 2017/0273797 A1 | 9/2017 | Gordon | |
| 2018/0014891 A1 | 1/2018 | Krebs | |
| 2018/0021960 A1 | 1/2018 | Grant | |
| 2018/0028261 A1 | 2/2018 | Chen | |
| 2018/0263647 A1 | 9/2018 | Aljuri | |
| 2018/0263685 A1 | 9/2018 | Onik | |
| 2018/0318011 A1 | 11/2018 | Leibinger | |
| 2018/0353253 A1 | 12/2018 | Bowling | |
| 2019/0015166 A1* | 1/2019 | Mahoney | A61B 17/32056 |
| 2019/0021753 A1 | 1/2019 | Jinno | |
| 2019/0076674 A1* | 3/2019 | Ergun | B06B 1/0292 |
| 2019/0105023 A1 | 4/2019 | Aljuri | |
| 2019/0105117 A1 | 4/2019 | Brisson | |
| 2019/0142396 A1 | 5/2019 | Stoianovici | |
| 2019/0151148 A1 | 5/2019 | Alvarez | |
| 2019/0201214 A1 | 7/2019 | Miller | |
| 2019/0202066 A1* | 7/2019 | Maret | B25J 17/025 |
| 2019/0223967 A1 | 7/2019 | Abbott | |
| 2019/0231450 A1* | 8/2019 | Waterbury | A61B 17/0281 |
| 2019/0262057 A1 | 8/2019 | Grant | |
| 2019/0321119 A1 | 10/2019 | Yeung | |
| 2019/0336238 A1 | 11/2019 | Yu | |
| 2020/0008874 A1 | 1/2020 | Barbagli | |
| 2020/0020249 A1 | 1/2020 | Jarc | |
| 2020/0138454 A1 | 5/2020 | Patel | |

(56) References Cited

U.S. PATENT DOCUMENTS

| | | |
|---|---|---|
| 2020/0197108 A1 | 6/2020 | Usui |
| 2020/0261297 A1 | 8/2020 | Strydom |
| 2020/0360097 A1 | 11/2020 | Dimaio |
| 2020/0360100 A1 | 11/2020 | Mantri |
| 2020/0405403 A1 | 12/2020 | Shelton, IV |
| 2021/0030496 A1 | 2/2021 | Devengenzo |
| 2021/0137612 A1 | 5/2021 | Staid |
| 2021/0378766 A1 | 12/2021 | Staid |
| 2021/0401521 A1 | 12/2021 | Mantri |
| 2021/0401522 A1 | 12/2021 | Mantri |
| 2022/0273166 A1 | 9/2022 | Nord |

FOREIGN PATENT DOCUMENTS

| | | |
|---|---|---|
| CN | 105764436 A | 7/2016 |
| CN | 105848552 | 8/2016 |
| CN | 109662779 | 4/2019 |
| CN | 111449694 | 7/2020 |
| EP | 1486900 | 12/2004 |
| JP | H7136173 | 5/1995 |
| JP | H07136173 | 5/1995 |
| JP | 2010142575 | 7/2010 |
| JP | 2015123201 | 7/2015 |
| JP | 2018198750 | 12/2018 |
| JP | 2019055287 | 4/2019 |
| NL | 1019547 | 5/2003 |
| WO | 2004004914 | 1/2004 |
| WO | 2008083407 | 7/2008 |
| WO | 2009111736 | 9/2009 |
| WO | 2011097505 | 8/2011 |
| WO | 2013053614 | 4/2013 |
| WO | 2013130895 | 9/2013 |
| WO | 2014127242 | 8/2014 |
| WO | 2014165703 | 10/2014 |
| WO | 2015035249 | 3/2015 |
| WO | 2015200538 | 12/2015 |
| WO | 2016004071 | 1/2016 |
| WO | 2016037132 | 3/2016 |
| WO | 2016037137 | 3/2016 |
| WO | 2016054256 | 4/2016 |
| WO | 2016187290 | 11/2016 |
| WO | 2017161331 | 9/2017 |
| WO | WO 2017/0192603 | * 11/2017 |
| WO | 2018013848 | 1/2018 |
| WO | 2018216382 | 11/2018 |
| WO | 2019032986 | 2/2019 |
| WO | 2019137665 | 7/2019 |
| WO | 2019246580 | 12/2019 |
| WO | 2020180724 | 9/2020 |
| WO | 2020181278 | 9/2020 |
| WO | 2020181280 | 9/2020 |
| WO | 2020181281 | 9/2020 |
| WO | 2020181290 | 9/2020 |
| WO | 2021130229 | 7/2021 |

OTHER PUBLICATIONS

International Search Report and Written Opinion for International Application No. PCT/US2020/021756, 17 pages (Jul. 6, 2020).
U.S. Appl. No. 16/939,972, filed Jul. 27, 2020.
U.S. Appl. No. 16/940,085, filed Jul. 27, 2020.
U.S. Appl. No. 16/939,880, filed Jul. 27, 2020.
Christoforou et al., Robotic Arm for Magnetic Resonance Imaging Guided Interventions, 2006, IEEE, p. 1-6 (Year: 2006).
Dwyer et al., A miniaturised robotic probe for real-time intraoperative fusion of ultrasound and endomicroscopy, 2015, IEEE, pg. ( Year: 2015).
International Search Report and Written Opinion for PCT/US2020/058884, 11 pages (Feb. 1, 2021).
Lim et al. "Robotic Transrectal Ultrasound-Guided Prostate Biopsy." IEEE Trans BME. Jan. 7, 2019. 11 pages. (Year: 2019).
Marmol etal., ArthroSLAM: Multi-Sensor Robust Visual Localization for Minimally Invasive Orthopedic Surgery, 2018, IEEE, p. 3882-3889 (Year: 2018).
Rosa et al., Laparoscopic optical biopsies: In vivo robotized mosaicing with probe-based confocal endomicroscopy, 2011, IEEE, p. 1339-1345 (Year: 2011).
Stoianovici et al. "MRI-Safe Robot for Endorectal Prostate Biopsy." IEEE/ASME Trans Mechatronics, vol. 19, No. 4 Aug. 2014. pp. 1289-1299. (Year: 2014).
Office Action (final) for U.S. Appl. No. 16/939,880, 7 pages (filed Mar. 8, 2021).
Office Action (final) for U.S. Appl. No. 16/939,972, 13 pages (filed Jan. 8, 2021).
Response to Non-Final Office Action for U.S. Appl. No. 16/939,880, 9 pages (filed Mar. 1, 2021).
Response to Non-Final Office Action for U.S. Appl. No. 16/940,085, 8 pages (filed Mar. 2, 2021).
Notice of Allowance for U.S. Appl. No. 16/939,880, 8 pages (filed Jun. 2, 2021).
Notice of Allowance for U.S. Appl. No. 16/939,972, 12 pages (filed May 13, 2021).
Office Action (Final) for U.S. Appl. No. 16/940,085, 14 pages (filed Apr. 13, 2021).
Response to Final Office Action for U.S. Appl. No. 16/940,085, 8 pages (filed Jun. 3, 2021).
Chirstoforou et al., Manipulator for magnetic resonance imaging guided interventions: design, prototype and feasibility, 2006, IEEE p. 3838-3843 (Year: 2006).
Xiao et al., Ultrasound Guided Robotic System for Transperineal Biopsy of the Prostate, 2006, IEEE, p. 1315-1320 (Year: 2006).
Office Action (Non-Final) for U.S. Appl. No. 16/940,085, 10 pages (filed May 25, 2022).
Office Action (Final) for U.S. Appl. No. 16/940,085, 11 pages (filed Sep. 29, 2022).
Office Action (Non-Final) for U.S. Appl. No. 16/940,085, 14 pages (Dec. 20, 2022).
Notice of Allowance for U.S. Appl. No. 17/304,572, 8 pages (filed Feb. 27, 2023).
Office Action for U.S. Appl. No. 17/304,572, 8 pages (filed Nov. 29, 2022).
Caponero, M.A., et al., "Fabrication and calibration of three temperature probes for monitoring the effects of thermal cancer ablation," 2017, IEEE, pp. 1-5 (2017).
Jakopec et al., Acrobot: a "hands-on" robot for total knee replacement surgery, 2002, IEEE, p. 116-120 (Year: 2002).
Sen et al., A cooperatively controlled robot for ultrasound monitoring of radiation therapy, 2013, IEEE, p. 3071-3076 (Year: 2013).
Non-Final Office Action for U.S. Appl. No. 16/940,085, 14 pages (filed Jun. 23, 2023).
Notice of Allowance for U.S. Appl. No. 17/304,572, 9 pages (filed Jun. 5, 2023).

* cited by examiner

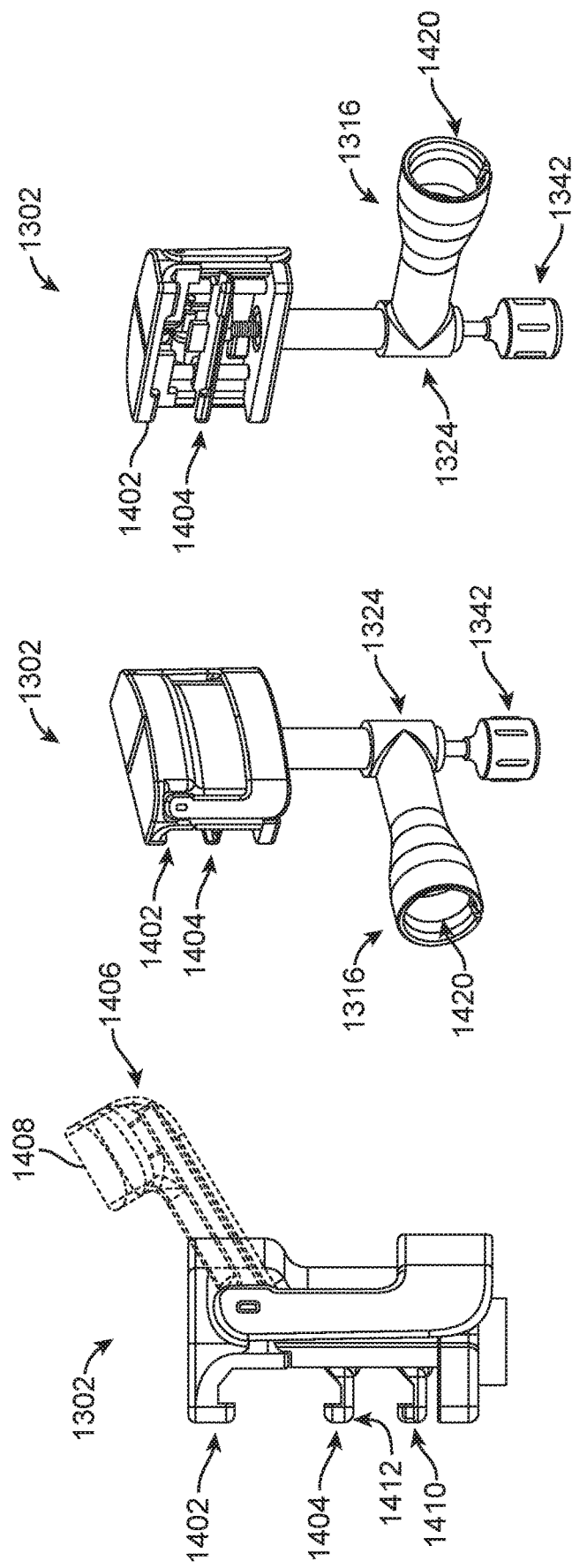

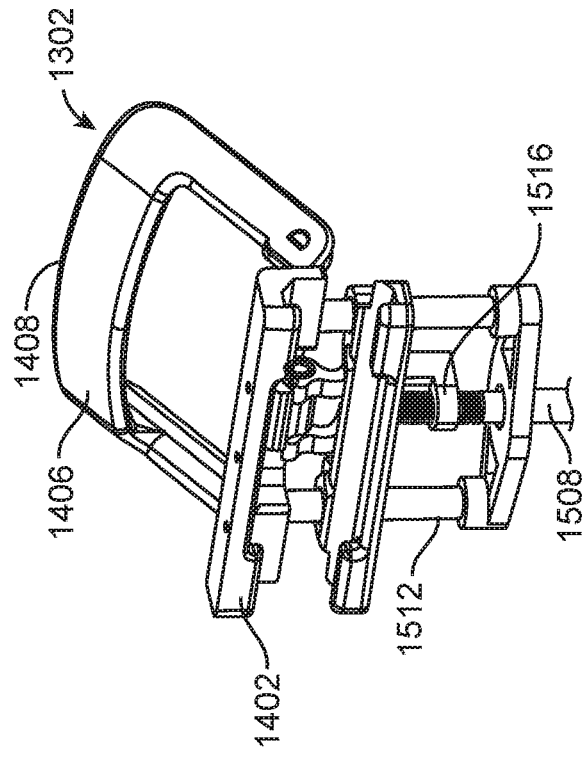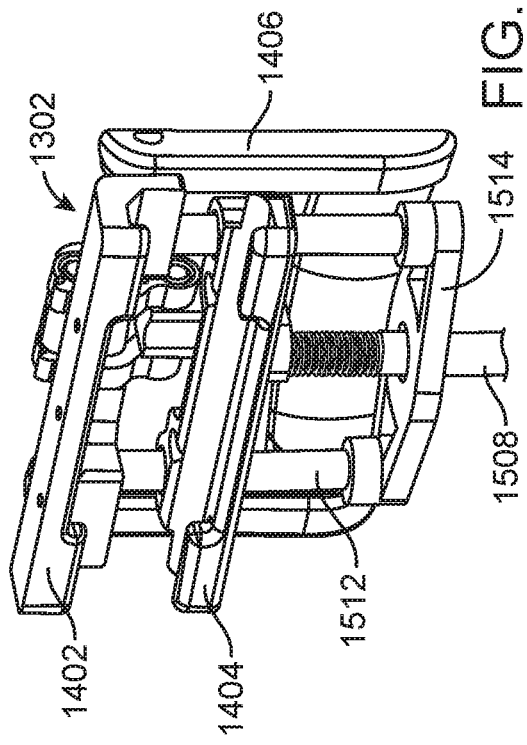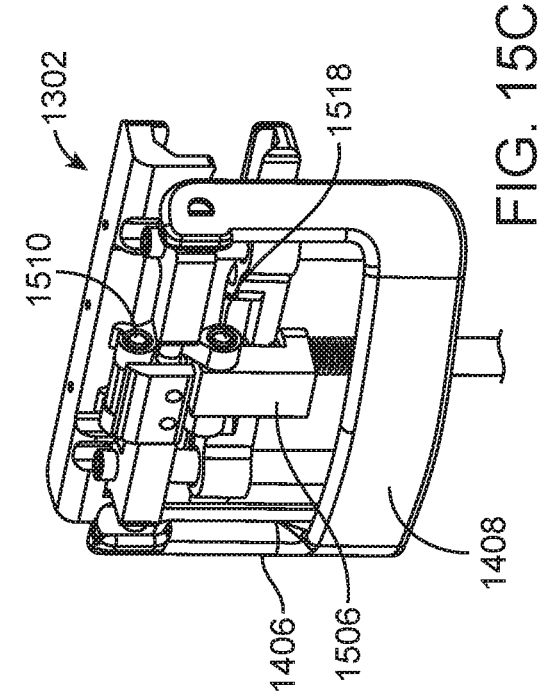

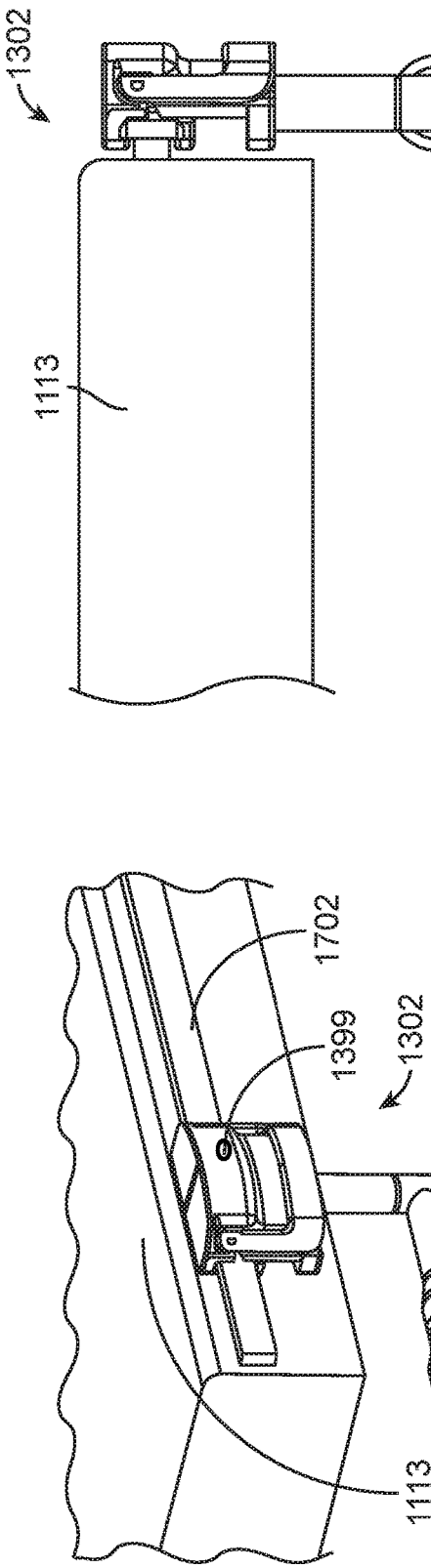
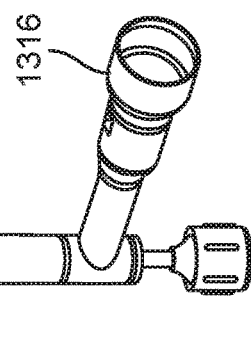
FIG. 17A
FIG. 17B
FIG. 17C

ROBOTIC ARMS AND METHODS FOR TISSUE RESECTION AND IMAGING

CROSS-REFERENCE TO RELATED APPLICATIONS

This application is a continuation application of International Patent Application No. PCT/US2020/021756, filed Mar. 9, 2020, entitled "ROBOTIC ARMS AND METHODS FOR TISSUE RESECTION AND IMAGING", which claims the benefit under 35 U.S.C. § 119(e) of U.S. Provisional Application No. 62/933,793, filed Nov. 11, 2019, and of U.S. Provisional Application No. 62/814,966, filed Mar. 7, 2019, the disclosures of which are incorporated, in their entirety, by this reference.

The subject matter of this application is related to the following patents and patent applications: U.S. patent application Ser. No. 11/968,445, filed Jan. 2, 2008, now U.S. Pat. No. 7,882,841; U.S. patent application Ser. No. 12/399,585, filed Mar. 6, 2009, now U.S. Pat. No. 8,814,921; U.S. patent application Ser. No. 14/334,247, filed Jul. 17, 2014, now U.S. Pat. No. 9,364,251; and International Application No. PCT/US2015/048695, filed Sep. 4, 2015; the entire contents of which are incorporated herein by reference.

BACKGROUND

The field of the present disclosure is related to the treatment of tissue with energy, and more specifically to the treatment of an organ such as the prostate with fluid stream energy.

Prior methods and apparatus of treating subjects such as patients can result in less than ideal tissue removal in at least some instances. For example, prior methods of prostate surgery can result in longer healing time and less than desirable outcome than would be ideal in at least some instances.

Prior methods and apparatus of imaging tissue can be less than ideal for imaging a treated tissue. For example, prior ultrasound methods and apparatus may not be well suited to view the treatment site during treatment, and alignment of diagnostic images with treatment images can be less than ideal. Also, at least some of the prior treatment methods and apparatus of treating tissue may not be well suited from combination with imaging systems of the prior art. In at least some instances, it would be helpful to provide improved imaging of tissue during surgery, for example to provide real time imaging of tissue that would allow a user to adjust the treatment based on real time images of the tissue. At least some of the prior methods and apparatus to image tissue during surgery can be somewhat cumbersome to use, and can result in delays in the patient treatment.

Prior methods and apparatus to treat an organ such as the prostate may provide a user interface that is somewhat cumbersome for the user, and can provide less than ideal planning of the surgery. Also, at least some of the prior methods and apparatus to treat tissue such as the prostate tissue can be somewhat less accurate than would be ideal. In at least some instances, the prior methods and apparatus may provide a less than ideal user experience. Also, at least some of the prior interfaces may provide less than ideal coupling of the treatment apparatus with tissue structures.

Prior methods and apparatus of treating tissue with robotic instrumentation can be less than ideal during a treatment. The robotic arms and surgical probes of a robotic surgery system may be aligned with one another and with the patient prior to the treatment. In some instances, the robotic arms and surgical probes are first manually moved and positioned before they are coupled to each other and locked in position for further controller-based adjustments. For example, a surgical probe or other tool coupled to a robotic arm may be manually guided through the anatomy to reach a target site, such as through the anus and rectum in the case of transrectal ultrasound ("TRUS"), or through the tortuous path of the urethra, prostate, and bladder neck which involves sharp turns through sensitive anatomy. In at least some instances, the maintenance of the desired alignment and the stability of the robotic arms after the manual adjustment and during treatment can be less than ideal. For example, the prior robotic arms and end surgical probes could be held too rigidly which could potentially lead to tissue injury related to patient movement, or may be held with less than ideal support strength, which could lead to less than ideal alignment with the target site if the robotic arms and surgical probes were to be disturbed, e.g. upon being bumped or being released from the grasp of a user subsequent to coupling.

Work in relation to the present disclosure suggests that prior approaches to aligning probes with robotic arms can be less than ideal in at least some instances.

While these aforementioned methods and apparatuses can be very effective and may represent a significant advance over prior luminal tissue treatment approaches, it would be desirable to provide improvements to assist in more accurate tissue removal in both fully automated and physician assisted operating modes. At least some of these objectives will be met by the inventions described hereinafter.

SUMMARY

Embodiments of the present disclosure provide improved methods and apparatus for performing tissue treatment such as tissue resection. In some embodiments, an image-guided treatment system comprises a treatment probe and an imaging probe. The imaging probe may be configured to provide an image of the target site while the treatment probe performs resection of the target tissue. In some embodiments, the treatment probe and the imaging probe are each coupled to robotic arms under control of one or more computing devices. The treatment probe may be coupled to a first robotic arm configured to provide computer-controlled movement of the treatment probe during tissue resection with the treatment probe. The imaging probe may be coupled to a second robotic arm configured to provide computer-controlled movement of the imaging probe during scanning of the target site with the imaging probe, before and/or during the tissue resection procedure with the treatment probe. One or more computing devices may be configured to execute instructions for operating the robotic arms in a passive mode in which the robotic arms are configured to be manually adjusted to position the treatment and imaging probes to a manually-set position, such as for imaging from and treatment in the same or different tissue sites. The one or more computing devices may be configured to execute instructions for maintaining the manually set position of the probes after robotic arms are released from manual adjustment. The robotic arms may be configured to maintain the manually set position with one or more of a in one or more of translational axis or a rotational axis. In some embodiments, the rotational angle is maintained to within 5° and the translational position to within 5 mm, or less. In some embodiments, the rotational angle and translational position are maintained for each of three axes, which can improve the accuracy of imaging and treatment with a probe.

The one or more computing devices operably coupled to the first and second robotic arms may be configured to automatically control the movement of the treatment probe and/or the imaging probe, for example based on a pre-planned or programmed scanning profile, or according to various pre-programmed parameters. The automatically controlled movement of the treatment probe along a treatment profile can perform treatment of the target site, for example. The automatically controlled movement of the image probe along an imaging profile can generate a 3-dimensional rendering of the target site, for example. The automatic, computer-controlled scanning of the target site with the imaging probe using the robotic arm can also be used to generate useful information regarding the target site for additional treatment. For example, the imaging probe may be configured to perform a color/Doppler scan of the target site after a resection procedure, in order to locate bleeding sites within the target site that require hemostasis. The 3-dimensional scan of the target site using the imaging probe may also be used to identify tissue anomalies at the target site, such as tumors.

Alternatively or additionally, the one or more computing devices may be configured to control movement of the treatment probe and/or the imaging probe in response to user inputs, for example through a graphical user interface of the treatment apparatus. In some embodiments, the one or more computing devices may be configured to limit the movement of the treatment probe and/or imaging probe within an allowable range of motion, which may be programmed into the first and/or second robotic arm prior to initiating use of the first or second arm under computer control.

The first robotic arm and/or the second robotic arm may be configured to adjust the position and/or orientation of the first arm and/or the second arm to maintain proper position or alignment of the treatment probe and the imaging probe, and/or to prevent collision or interference between the treatment probe and the imaging probe outside of the patient's body.

The first robotic arm and/or the second robotic arm may comprise one or more feedback sensing mechanisms. For example, the first robotic arm and/or the second robotic arm may be operably coupled with a force sensor configured to detect a compression of the tissue anterior to the treatment probe and/or imaging probe. The one or more computing devices may comprise instructions to control movement of the robotic arms in response to forces detected by the sensor, for example to prevent over-compression of the anterior tissue and resultant damage to the tissue and/or the probe. Another exemplary feedback sensing mechanism may comprise position and/or motion sensors operably coupled with the first and/or second robotic arm. The one or more computing devices may comprise instructions to control movement of the robotic arms in response to the position and/or motion detected by the sensors, for example to adjust the position of the treatment and/or imaging probe in response to patient movement during a treatment and/or scanning procedure.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the present disclosure are utilized, and the accompanying drawings of which:

FIGS. 14A, 14B, and 14C illustrate a perspective view and perspective views of a clamp for us with a treatment system, in accordance with some embodiments;

FIGS. 15A, 15B, 15C, and 15D illustrate perspective internal views of a clamp for use with a treatment system, in accordance with some embodiments;

FIGS. 17A, 17B, and 17C illustrated perspective, side and perspective view respectively of a clamping system, in accordance with some embodiments;

DETAILED DESCRIPTION

Figure 1:
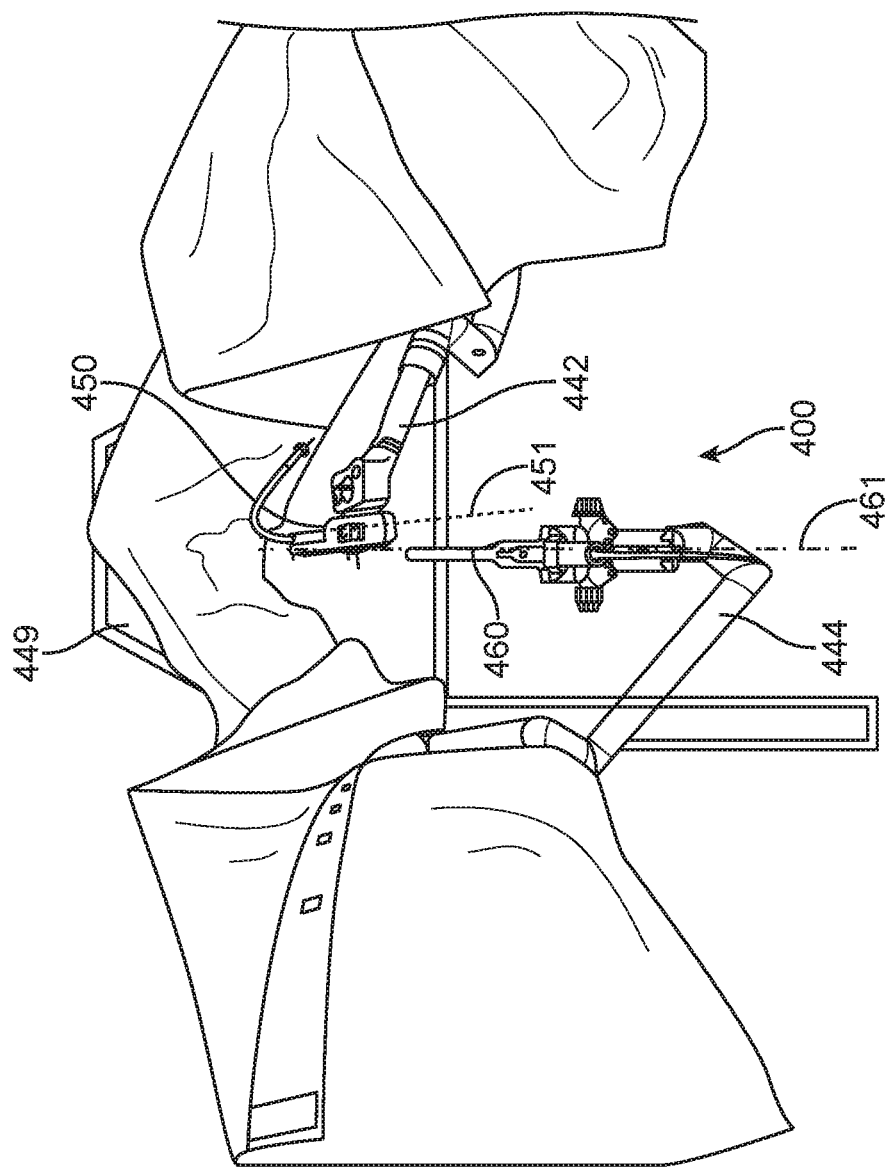
FIG. 1 shows a front view of a system for performing tissue resection in a patient, in accordance with some embodiments.

Embodiments of the present disclosure provide improved methods and apparatus for performing tissue treatment such as tissue resection, for example prostate tissue resection. The methods and apparatus disclosed herein are well suited for many types of surgical procedures, and can be incorporated into many prior systems and methods. While some embodiments of the present disclosure are directed to transurethral treatment of the prostate, some aspects of the present disclosure may also be used to treat and modify other tissues and associated organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

The presently disclosed methods and apparatus are well suited for treating many types of tissue with an energy source. The tissue may comprise soft tissue, such as glandular tissue or capsular tissue, or hard tissue such as bone or blockages, such as kidney stones, for example. The energy source may comprise one or more of a laser beam, a water jet, an electrode, ultrasound, high intensity focused ultrasound, mechanical vibrations, radiofrequency (RF) energy an ultrasound transducer, microwave energy, cavitating energy such as a cavitating water jet or ultrasonic cavitations, radiation such as ionizing radiation from a radioisotope, or ion energy from ionization electrodes or plasma energy from plasma electrodes. The presently disclosed methods and apparatus are well suited for performing lithotripsy to break up kidney stones, for example. The presently disclosed methods and apparatus are well suited for treatment with radiation, such as a radio isotope on the treatment probe. The radiation treatment can be provided on the probe and removed with the probe, or implanted from the treatment probe, for the treatment of cancer for example.

In some embodiments, an image-guided treatment system comprises a treatment probe and an imaging probe. The imaging probe may be configured to provide an image of the target site while the treatment probe performs resection of the target tissue. The treatment probe and the imaging probe may each be coupled to robotic arms under control of one or more computing devices, in order to enable more precisely controlled movement of one or both of the arms and to improve the safety and efficiency of treatment using the treatment system.

The robotic arms can be configured in many ways. Work in relation to the present disclosure suggests that a TRUS probe can exert force on a robotic arm. In some embodiments this force is related to force from the patient against the probe. In some embodiments this force is related to force caused by the practitioner surgeon moving the probe against and moving the tissue for the purpose of improving imaging or tissue position relative to the intended treatment. The length of the probe can result in a corresponding torque on the robotic arm.

The present inventors have conducted experiments to determine the amount of force from the TRUS probe that can be applied to the robotic arm. This force can be measured at a motor mount exterior to the patient, for example. The force can range from 0 to about 5-kilograms, depending on the surgical placement of the probe and patient. In some embodiments, the distance from the arm to the point of contact with prostate corresponds to an amount of torque on the arm.

Instrument positioning can have three categories of motion control and capability in accordance with some embodiments disclosed herein. The three categories of motion generally comprise a 1) coarse motion capability for movement, storage and preparation for surgery, 2) an intermediate movement capability for aligning the probe with the patient and inserting the probe into the patient, and 3) a fine movement capability corresponding to positional tolerances for accurate surgery.

Coarse motion capability allows for storage below and adjacent to the table and during patient positioning, for example.

Intermediate motion allows for instrument positioning with respect to the patient on the surgical support structure, e.g. an operating room ("OR") table, for example when the system is being prepared and positioned for patient entry. A typical range of position for the TRUS probe or any suitable surgically invasive probe is to have free motion for insertion into the patient, which can be describe with a X,Y,Z coordinate system. With an appropriate coordinate reference system, the entry to a lumen of the patient may correspond to values of 0, 0, 0 in an X,Y,Z coordinate system. The coordinate reference may also comprise angular coordinate references of X',Y',Z'. The entry to the lumen may comprise an anus of the patient. With an anal entrance at 0,0,0 and the probe colinear with the patient axis, the intermedia motion may comprise an X motion tolerance of +/−2 to 15 cm, Y motion tolerance of +/−2 to 15 cm, and Z motion tolerance of +/−2 to 30 cm. In some embodiments, the X and Y motion corresponds to translation of the probe along the X and Y coordinate references. The Z axis position corresponds to movement along an axis of the lumen, and may correspond to advancement and retraction of the probe along the body lumen, e.g. translational movement into and out of the patient. With an angular adjustment of X',Y', Z', the angular position capability may comprise X'+/−zero to 30 degrees, Y'+/−zero to 30 degrees, Z'+/−zero to 30 degrees, with respect to the natural axis of the patient. Work in relation to the present disclosure suggests that a probe with these angular capabilities can be manipulated by a user for insertion into the patient.

In some embodiments, the fine movement capability and tolerances correspond to a configuration of the robotic probe and arms with the probe positioned in the patient, for example during tissue resection and imaging. When the system is in use with instruments positioned for diagnosis and treatment, the sensors and controls and described herein can be configured to prevent tissue damage, and also to position treatment probe and imaging probe to obtain reliable images, e.g. optimal images, and the treatment and imaging probes can be precisely positioned and firmly held in position against tissue pressures. The X,Y,Z reference frame can be centered on the lumen entrance at 0,0,0 and (the probe colinear with the patient axis). In some embodiments, X motion tolerance is +/−0 to 5 cm; the Y motion tolerance is +/−0 to 5 cm; and Z motion tolerance is +/−0 to 15 cm. The X and Y motion generally corresponds to translation of the probe, and the Z axis corresponds to advancement and retraction of the probe in and out of the patient. The corresponding angular adjustment ranges for X',Y',Z' are X'+/−zero to 10 degrees, Y'+/−zero to 10 degrees, and Z'+/−zero to 15 degrees, with respect to a natural axis of the patient, for example with reference to a midline of the patient with the Z axis extending along the midline of the patient. While the above values represent ranges of motion, the robotics arms and surgical probes may provide tighter tolerances for fixed position configurations of the probe. For example, when the probe is intended to be held in a fixed position, the rotational tolerances can maintain one or more of X',Y',Z' within a within +/−5 tolerance or less, e.g. +/−3°. With respect to translational movement, the manually set position can be maintained to a positional tolerance of 5 mm or less, 3 mm or less, or 2 mm or less for one or more of the X, Y, Z axes, for example. In some embodiments, these tolerances are maintained for each of X, Y, Z and X', Y', Z'. In some embodiments, the probe is manually set, and the translational and rotational tolerances are maintained to within the above values, which can improve the accuracy of the tissue treatment and associated imaging. These tolerance may correspond a maximal structural relaxing or loading of the arm with the probe mounted thereon, for example.

The probe can be manipulated and inserted into the patient in many ways. For example the probe can be manipulated manually, and the robotic arm moved into alignment with the probe and coupled to the probe, with the probe maintaining the above tolerances when released by the user and the arm subsequently supporting the full load of the patient and probes. The arm can be brought into alignment with the probe manually, or with at least some automation in which sensors and guidance circuitry are used to bring the arm into alignment with the probe held by the user. The arm may comprise a coupling structure to engage the probe with 6 degrees of freedom, such that a coupling structure on the arm can be brought into precise alignment with the coupling structure on the probe. The coupling structures can be subsequently engaged and coupled to each other in response to detection of the alignment. In some embodiments, sensors are provided on one or more of the arm or the probe to detect alignment between the arm and probe, and the coupling structures engaged in response to the detected alignment. The robotic arm may comprise a linkage coupled to a processor, in which the processor controls movement of the arm and brings the arm into alignment with the probe held by the user.

In some embodiments, the urethral probe has similar dimensional, motion and tolerance capabilities to the TRUS probe.

In some embodiments, the probe comprises a mass within a range from about 250 grams to 1500 grams, and the arm maintains the tolerances described herein with the probe comprising the mass within this range.

The robotics arms as described herein can improve alignment between the treatment probe and the imaging probe, which may comprise sagittal plane of an imaging TRUS probe. For example, the treatment probe be aligned substantially coplanar along the sagittal plane of the imaging probe. This coplanarity can provide clear imaging and alignment of coordinates of the treatment probe and imaging probe. In some embodiments, the tolerance of this coplanarity is related to the combination of the width of the treatment probe and the width of the imaging plane capability, e.g. width of the image captured with ultrasound beam forming. The relative position of the TRUS to the treatment probe can be substantially parallel and aligned within an angular tolerance. The alignment can be within a range from +/−zero (parallel) to about 30 degrees. In some embodiments, the elongate axis of the treatment probe and TRUS probe are aligned in a substantially co-planar configuration, with the separation distance between the probes varying along the length of the imaging and treatment probes. For example, the distal tip of the treatment probe can be farther away from the TRUS probe and the proximal end closer to the TRUS probe, in which the two probes are inclined relative to each other, although substantially coplanar. The inclination between the two probes can be related to the tissue constraints of natural orifices of each unique human. The distances between the entrances to the naturally available orifices can vary, for example within a range from about 5 cm to about 25 cm separation.

In some embodiments, the imaging probe and the treatment probe are aligned so that the treatment probe is within the field of view of the imaging probe. In some embodiments, the alignment is configured to maintain the treatment probe within a field of view of the imaging probe. In some embodiments, the treatment probe is configured to move to a position and the imaging probe is configured to maintain the treatment probe within the field of view.

FIG. 1 shows an exemplary embodiment of a system 400 for performing tissue resection in a patient. The system 400 may comprise a treatment probe 450 and an imaging probe 460. The treatment probe 450 may be coupled to a first arm 442, and the imaging probe 460 coupled to a second arm 444. One or both of the first arm 442 and the second arm 444 may comprise robotic arms whose movements may be controlled by one or more computing devices operably coupled with the arms. The treatment probe 450 may comprise a device for removing target tissue from a target site within a patient. The treatment probe 450 may be configured to deliver energy from the treatment probe 450 to the target tissue sufficient for removing the target tissue. For example, the treatment probe 450 may comprise an electrosurgical ablation device, a laser ablation device, a transurethral needle ablation device, a water jet ablation device, or any combination thereof. The imaging probe 460 may be configured to deliver energy from the imaging probe 460 to the target tissue sufficient for imaging the target tissue. The imaging probe 460 may comprise an ultrasound probe, a magnetic resonance probe, an endoscope, or a fluoroscopy probe, for example. The first arm 442 and the second arm 444 may be configured to be independently adjustable, adjustable according to a fixed relationship, adjustable according to a user selected relationship, independently lockable, or simultaneously lockable, or any combination thereof. The first arm 442 and the second arm 444 may have multiple degrees of freedom, for example six degrees of freedom, to manipulate the treatment probe 450 and the imaging probe 460, respectively. The treatment system 400 may be used to perform tissue resection in an organ of a patient, such a prostate of a patient. The patient may be positioned on a patient support 449 such as a bed, a table, a chair, or a platform. The treatment probe 450 may be inserted into the target site of the patient along an axis of entry that coincides with the elongate axis 451 of the treatment probe. For example, the treatment probe 450 may be configured for insertion into the urethra of the patient, so as to position an energy delivery region of the treatment probe within the prostate of the patient. The imaging probe 460 may be inserted into the patient at the target site or at a site adjacent the target site of the patient, along an axis of entry that coincides with the elongate axis 461 of the imaging probe. For example, the imaging probe 460 may comprise a transrectal ultrasound (TRUS) probe, configured for insertion into the rectum of the patient to view the patient's prostate and the surrounding tissues. As shown in FIG. 1, the first arm 442 and the second arm 444 may be covered in sterile drapes to provide a sterile operating environment, keep the robotic arms clean, and reduce risks of damaging the robotic arms. Further details regarding the various components of the system 400 suitable for incorporation with embodiments as disclosed herein may be found in U.S. Pat. Nos. 7,882,841, 8,814,921, 9,364,251, and PCT Publication No. WO2013/130895, the entire disclosures of which are incorporated herein by reference.

Figure 2:
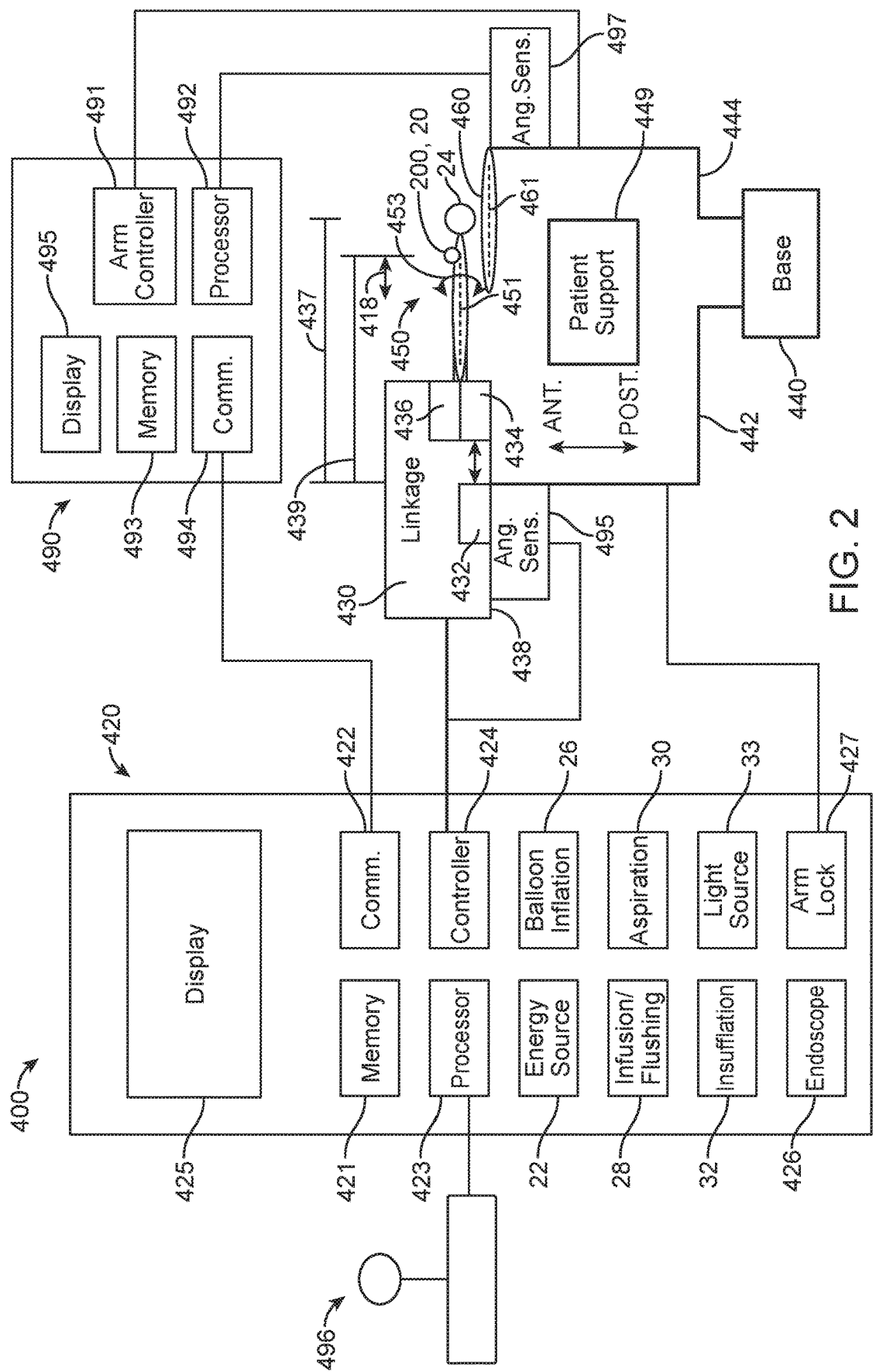
FIG. 2 schematically illustrates a system for performing tissue resection in a patient, in accordance with some embodiments.

FIG. 2 schematically illustrates an exemplary embodiment of the system 400 for performing tissue resection in a patient. The system 400 comprises a treatment probe 450 and may optionally comprise an imaging probe 460. The treatment probe 450 is coupled to a console 420 and a linkage 430. The linkage 430 may comprise one or more components of the robotic arm 442. The imaging probe 460 is coupled to an imaging console 490. The imaging probe may be coupled to the second robotic arm 444, for example. The patient treatment probe 450 and the imaging probe 460 can be coupled to a common base 440. The patient is supported with the patient support 449. The treatment probe 450 is coupled to the base 440 with a first arm 442. The imaging probe 460 is coupled to the base 440 with a second arm 444. One or both of the first arm 442 and the second arm 444 may comprise robotic arms whose movements may be controlled by one or more computing devices operably coupled with the arms, as described in further detail herein.

Although reference is made to a common base, the robotic arms can be coupled to a bed rail, a console, or any suitable supporting structure to support the base of the robotic arm.

In some embodiments, system 400 comprises a user input device 496 coupled to processor 423 for a user to manipulate the surgical instrument on the robotic arm. A user input device 496 can be located in any suitable place, for example, on a console, on a robotic arm, on a mobile base, and there may be one, two, three, four, or more user input devices used in conjunction with the system 400 to either provide redundant avenues of input, unique input commands, or a combination. In some embodiments, the user input device comprises a controller to move the end of the treatment probe or the imaging probe with movements in response to mechanical movements of the user input device. The end of the probe can be shown on the display 425 and the user can manipulate the end of the probe. For example, the user input device may comprise a 6 degree of freedom input controller in which the user is able to move the input device with 6 degrees of freedom, and the distal end of the probe moves in response to movements of the controller. In some embodiments, the 6 degrees of freedom comprise three translational degrees of freedom and three rotational degrees of freedom. The processor can be configured with instructions for the probe control to switch between automated image guidance treatment with the energy source and treatment with the energy source with user movement of the user input device, for example.

The patient is placed on the patient support 449, such that the treatment probe 450 and ultrasound probe 460 can be inserted into the patient. The patient can be placed in one or more of many positions such as prone, supine, upright, or inclined, for example. In some embodiments, the patient is placed in a lithotomy position, and stirrups may be used, for example. In some embodiments, the treatment probe 450 is inserted into the patient in a first direction on a first side of the patient, and the imaging probe is inserted into the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each of the first and second arms may comprise a substantially unlocked configuration such the treatment or imaging probe can be desirably rotated and translated in order to insert the probe into the patient. When the probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In some embodiments, the treatment probe 450 is coupled to the imaging probe 460 in order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In some embodiments, the first arm 442 is a movable and lockable arm such that the treatment probe 450 can be positioned in a desired location in a patient. When the probe 450 has been positioned in the desired location of the patient, the first arm 442 can be locked with an arm lock 427. The imaging probe can be coupled to base 440 with the second arm 444, which can be used to adjust the alignment of the imaging probe when the treatment probe is locked in position. The second arm 444 may comprise a lockable and movable arm under control of the imaging system or of the console and of the user interface, for example. The movable arm 444 may be micro-actuatable so that the imaging probe 460 can be adjusted with small movements, for example a millimeter or so in relation to the treatment probe 450.

In some embodiments, the treatment probe 450 and the imaging probe 460 are coupled to angle sensors so that the treatment can be controlled based on the alignment of the imaging probe 460 and the treatment probe 450. A first angle sensor 495 may be coupled to the treatment probe 450 with a support 438. A second angle sensor 497 may be coupled to the imaging probe 460. The angle sensors may comprise one or more of many types of angle sensors. For example, the angle sensors may comprise goniometers, accelerometers and combinations thereof. In some embodiments, the first angle sensor 495 comprises a 3-dimensional accelerometer to determine an orientation of the treatment probe 450 in three dimensions. In some embodiments, the second angle sensor 497 comprises a 3-dimensional accelerometer to determine an orientation of the imaging probe 460 in three dimensions. Alternatively or in combination, the first angle sensor 495 may comprise a goniometer to determine an angle of treatment probe 450 along an elongate axis 451 of the treatment probe. The second angle sensor 497 may comprise a goniometer to determine an angle of the imaging probe 460 along an elongate axis 461 of the imaging probe 460. The first angle sensor 495 is coupled to a controller 424 of the treatment console 420. The second angle sensor 497 of the imaging probe is coupled to a processor 492 of the imaging console 490. Alternatively or in combination, the second angle sensor 497 may be coupled to the controller 424 of the treatment console 420.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging console 490 via the communication circuitry 494 of the imaging console. Arm lock 427 of console 420 may be coupled to the first arm 442 to lock the first arm or to allow the first arm to be freely movable to insert probe 450 into the patient.

Optionally, the console 420 may comprise components of an endoscope 426 that is coupled to anchor 24 of the treatment probe 450. Endoscope 426 can comprise components of console 420 and an endoscope insertable with treatment probe 450 to treat the patient.

Optionally, the console 420 may comprise one or more of modules operably coupled with the treatment probe 450 to control an aspect of the treatment with the treatment probe. For example, the console 420 may comprise one or more of an energy source 22 to provide energy to the treatment probe, balloon inflation control 26 to affect inflation of a balloon used to anchor the treatment probe at a target treatment site, infusion/flushing control 28 to control infusion and flushing of the probe, aspiration control 30 to control aspiration by the probe, insufflation control 37 to control insufflation of the target treatment site (e.g., the prostate), or a light source 33 such as a source of infrared, visible light or ultraviolet light to provide optical energy to the treatment probe.

The processor, controller and control electronics and circuitry can include one or more of many suitable components, such as one or more processor, one or more field-programmable gate array (FPGA), and one or more memory storage devices. In some embodiments, the control electronics controls the control panel of the graphic user interface (hereinafter "GUI") to provide for pre-procedure planning according to user specified treatment parameters as well as to provide user control over the surgery procedure.

The treatment probe 450 may comprise an anchor 24. The anchor 24 can anchor the distal end of the probe 450 while energy is delivered to energy delivery region 20 with the probe 450. The probe 450 may comprise a nozzle 200.

The treatment probe 450 may be coupled to the first arm 442 with a linkage 430. The linkage 430 may comprise components to move energy delivery region 20 to a desired target location of the patient, for example, based on images of the patient. The linkage 430 may comprise a first portion 432, a second portion 434 and a third portion 436. The first portion 432 may comprise a substantially fixed anchoring portion. The substantially fixed anchoring portion 432 may be fixed to support 438. Support 438 may comprise a reference frame of linkage 430. Support 438 may comprise a rigid chassis or frame or housing to rigidly and stiffly couple the first arm 442 to treatment probe 450. The first portion 432 can remain substantially fixed, while the second portion 434 and third portion 436 can move to direct energy from the probe 450 to the patient. The first portion 432 may be fixed to the substantially constant distance 437 to the anchor 24. The substantially fixed distance 437 between the anchor 24 and the fixed first portion 432 of the linkage allows the treatment to be accurately placed. The first portion 432 may comprise a linear actuator to accurately position the high-pressure nozzle 200 in the energy delivery region 20 at a desired axial position along an elongate axis 451 of treatment probe 450.

The elongate axis 451 of treatment probe 450 generally extends between a proximal portion of the probe 450 near linkage 430 to a distal end having anchor 24 attached thereto. The third portion 436 can control a rotation angle 453 around the elongate axis 451. During treatment of the patient, a distance 439 between the energy delivery region 20 and the first portion 432 of the linkage may vary with reference to anchor 24. The distance 439 may adjust in manner 418 in response to computer control to set a target location along the elongate axis 451 of the treatment probe referenced to anchor 24. The first portion of the linkage remains fixed, while the second portion 434 adjusts the position of the energy delivery region 20 along the axis 451. The third portion of the linkage 436 adjusts the angle 453 around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging console 490 may comprise a memory 493, communication circuitry 494 and processor 492. The processor 492 in corresponding circuitry is coupled to the imaging probe 460. An arm controller 491 is coupled to arm 444 to precisely position imaging probe 460. The imaging console may further comprise a display 425.

In order to facilitate precise control of the treatment probe and/or the imaging probe during treatment of the patient, each of the treatment probe and the imaging probe may be coupled to a robotic, computer-controllable arm. For example, referring to system 400 shown in FIG. 2, one or both of the first arm 442 coupled to the treatment probe 450 and the second arm 444 coupled to the imaging probe 460 may comprise robotic, computer-controllable arms. The robotic arms may be operably coupled with one or more computing devices configured to control movement of the robotic arms. For example, the first robotic arm 442 may be operably coupled with the processor 423 of the console 420, or the second robotic arm 444 may be operably coupled with the processor 492 of the imaging console 490 and/or to the processor 423 of the console 420. The one or more computing devices, such as the processors 423 and 492, may comprise computer executable instructions for controlling movement of the one or more robotic arms. The first and second robotic arms may be substantially similar in construction and function, or they may be different to accommodate specific functional requirements for controlling movement of the treatment probe versus the imaging probe.

The robotic arm may comprise 6 or 7 or more joints to allow the arm to move under computer control. Suitable robotic arms are commercially available from several manufacturers such as RoboDK Inc., Kinova Inc. and several other manufacturers.

The one or more computing devices operably coupled to the first and second robotic arms may be configured to automatically control the movement of the treatment probe and/or the imaging probe. For example, the robotic arms may be configured to automatically adjust the position and/or orientation of the treatment probe and/or imaging probe during treatment of the patient, according to one or more pre-programmed parameters. The robotic arms may be configured to automatically move the treatment probe and/or imaging probe along a pre-planned or programmed treatment or scanning profile, which may be stored on a memory of the one or more computing devices. Alternatively or additionally to automatic adjustment of the robotic the one or more computing devices may be configured to control movement of the treatment probe and/or the imaging probe in response to user inputs, for example through a graphical user interface of the treatment apparatus. Alternatively or additionally to automatic adjustment of the robotic arms, the one or more computing devices may be configured to control movement of the treatment probe and/or the imaging probe in response to real-time positioning information, for example in response to anatomy recognized in one or more images captured by the imaging probe or other imaging source (from which allowable ranges of motion of the treatment probe and/or the imaging probe may be established) and/or position information of the treatment probe and/or imaging probe from one or more sensors coupled to the probes and/or robotic arms.

Figure 3B:
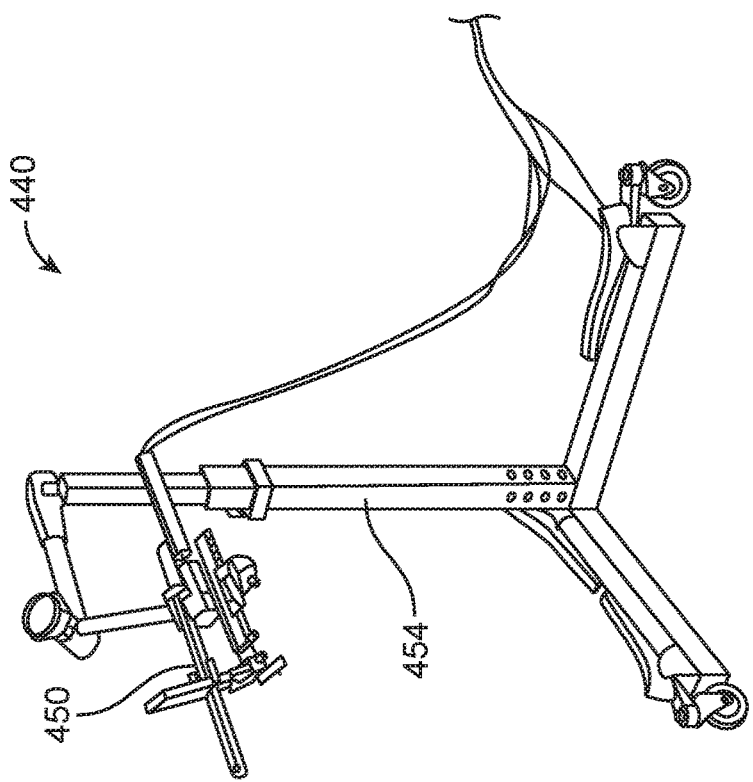
FIGS. 3A and 3B show perspective views of a common base or mount for supporting one or more robotic arms, in accordance with some embodiments.
Figure 3A:
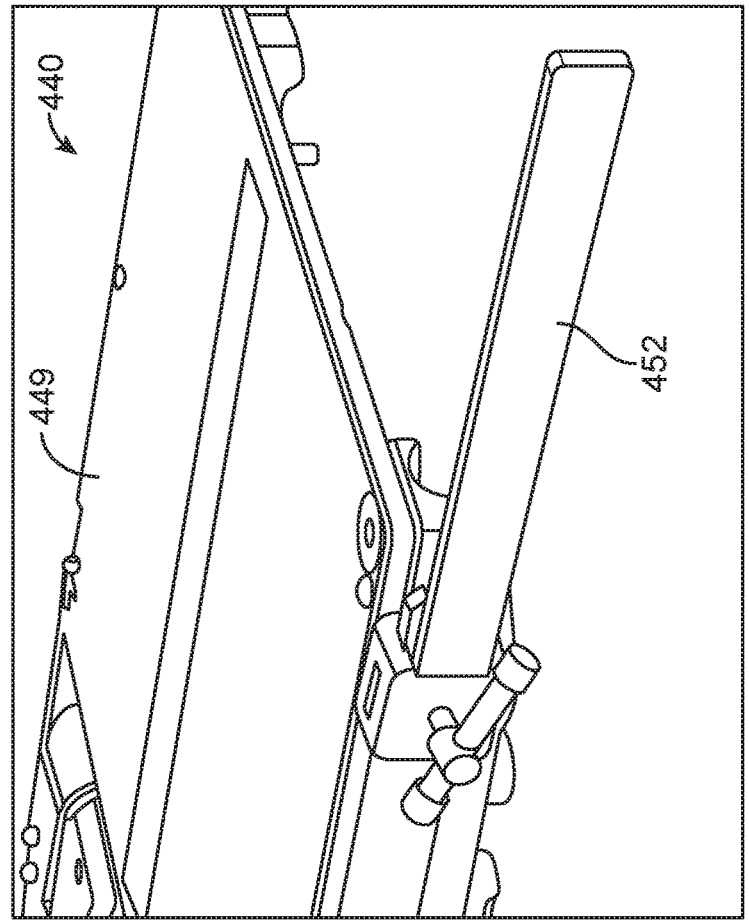

FIGS. 3A and 3B show exemplary embodiments of a common base or mount 440 for supporting one or more robotic arms of an image-guided treatment system as disclosed herein. FIG. 3A shows a patient support 449 comprising one or more rails 452. The patient support 449 may comprise a surgical table or a platform. One or more robotic arms associated with one or more of the treatment probe or the imaging probe may be mounted to the rails 452, such that the rails function as the common base 440. FIG. 3B shows a common base 440 comprising a floor stand 454 configured to couple to the first robotic arm connected to the treatment probe and/or the second robotic arm connected to the imaging probe. The floor-stand 454 may be positioned between the patient's legs during the treatment procedure.

Figure 4A:
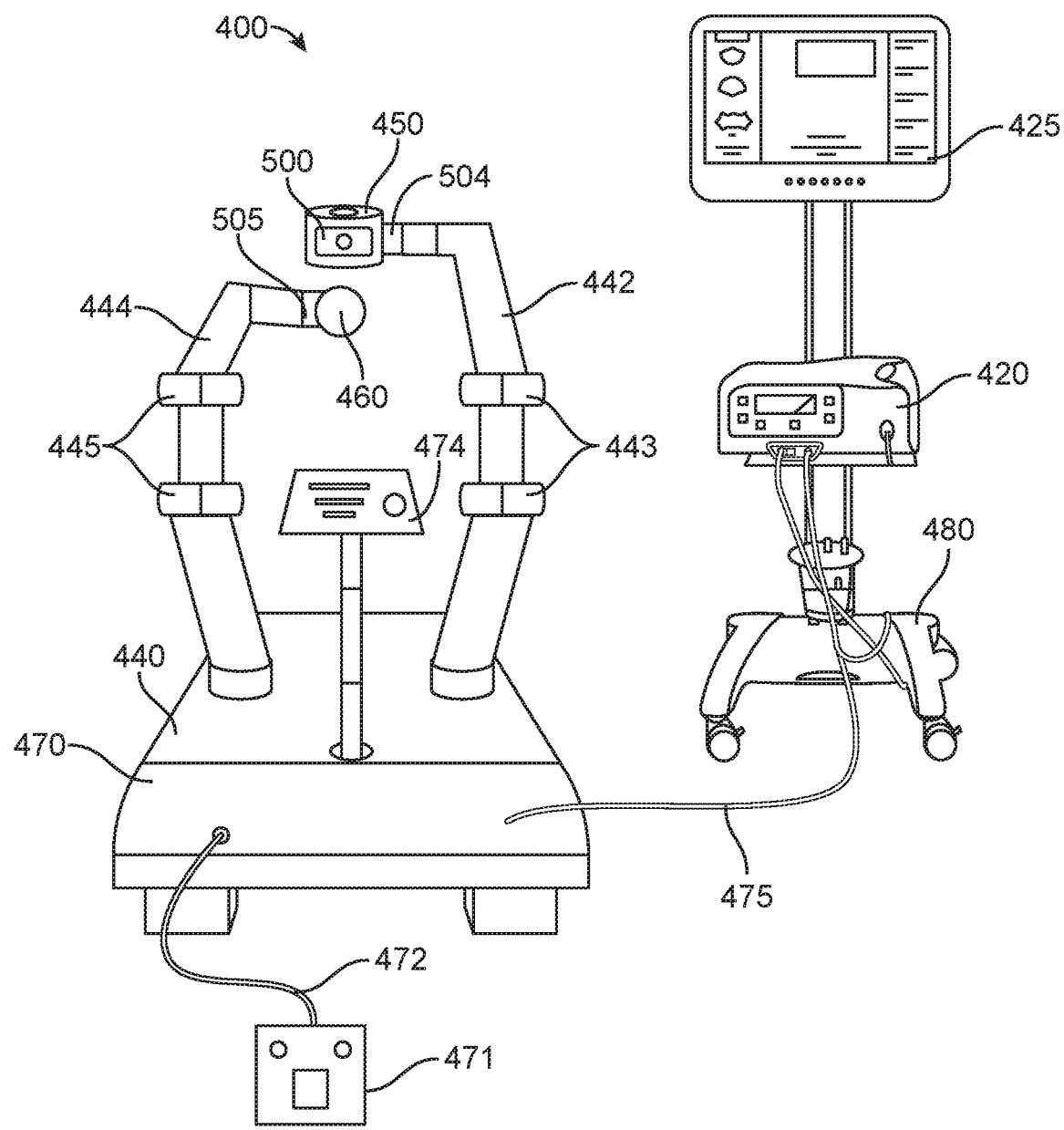
FIGS. 4A and 4B illustrate a perspective and side view, respectively, of a system for performing tissue resection in a patient that comprises a mobile base, in accordance with some embodiments.
Figure 4B:
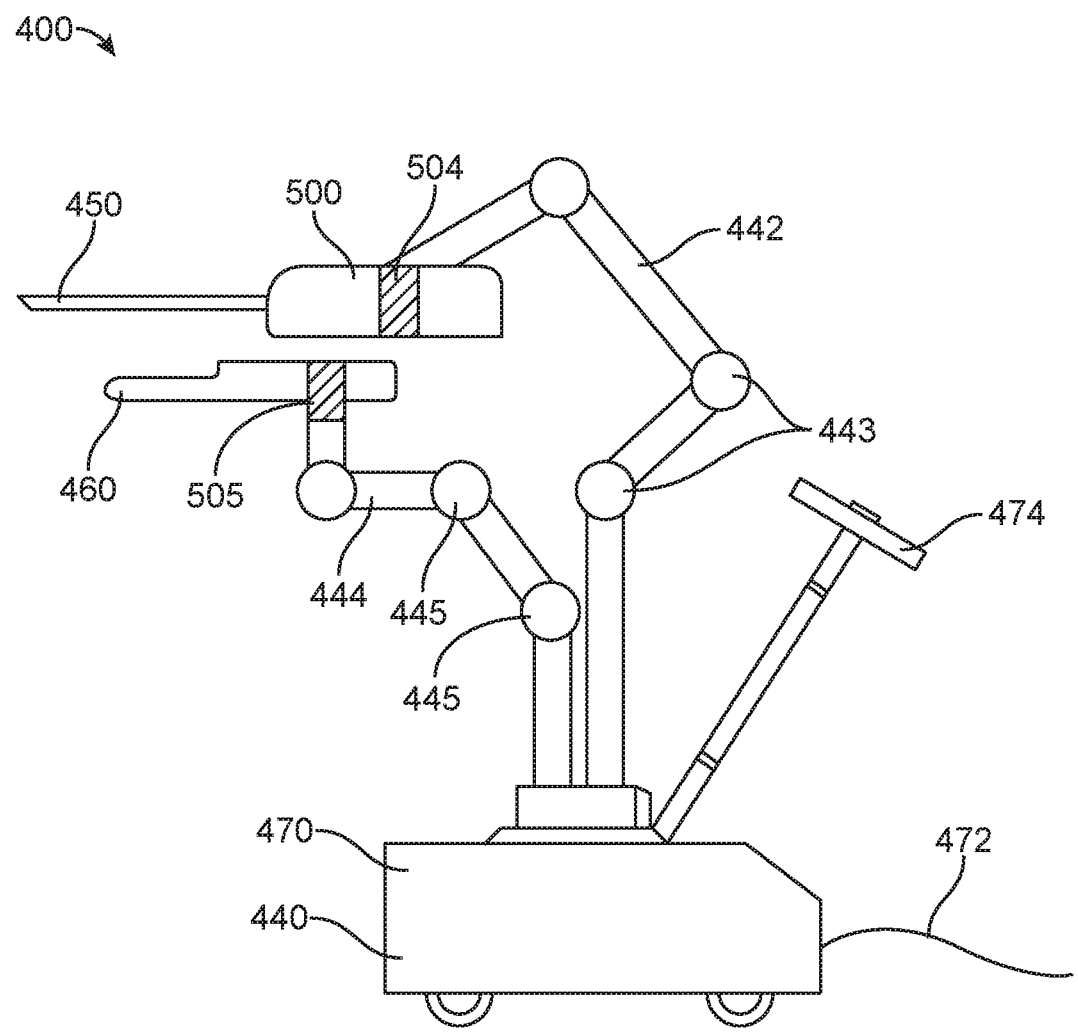

FIGS. 4A and 4B illustrate an exemplary embodiment of a treatment system 400 as described herein comprising a mobile base 470. FIG. 4A is a front view and FIG. 4B is a side view of the treatment system 400. The treatment system 400 comprises a treatment probe 450 coupled to a first robotic arm 442, and an imaging probe 460 coupled to a second robotic arm 444. The first robotic arm 442 and the second robotic arm 444 each comprises a proximal end and a distal end, the distal end coupled to the treatment probe 450 and the imaging probe 460, respectively, and the proximal end coupled to a common base 440 comprising a mobile base 470. The first robotic arm 442 may comprise a first arm coupling structure 504 to couple to the treatment probe 450, and the second robotic arm 444 may comprise a second arm coupling structure 505 to couple to the imaging probe 460. The treatment probe 450 may be coupled to the distal end of the first robotic arm 442 via an attachment device 500, which may comprise a linkage configured to affect movement of the treatment probe as described herein (e.g., rotation, translation, pitch, etc.). Coupling of the treatment probe 450 to the first robotic arm 442 may be fixed, releasable, or user adjustable. Similarly, coupling of the imaging probe 460 to the second robotic arm 444 may be fixed, releasable, or user adjustable.

The first robotic arm 442 may articulate at one or more first arm joints 443. The imaging arm 444 may articulate at one or more second arm joints 445. Each arm joint 443 or 445 may be operably coupled with a computer-controllable actuator, such as a stepper motor, to affect movement at the joint. Each arm joint 443 or 445 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each arm joint 443 or 445 may comprise a linear, orthogonal, rotational, twisting, or revolving joint, or any combination thereof.

The system 400 may further comprise a console 420 as described herein, which may be supported by a mobile support 480 separate from the mobile base 470. The console 420 may be operably coupled with the mobile base 470 via a power and communication cable 475, to allow control of the treatment probe 450 coupled to the mobile base via the first robotic arm. The treatment console 420 comprises a processor and a memory having stored thereon computer-executable instructions for execution by the processor, to control various modules or functionalities of the treatment console, such as an energy source, infusion/flushing control, aspiration control, and other components as described herein with reference to FIG. 2. The treatment console 420 may further comprise a display 425 in communication with the processor. The display 425 may be configured to display, for example, one or more of: subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that has been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 470 may further comprise one or mom computing devices to control operation of the one or more robotic arms. For example, the mobile base may comprise processors and a memory having stored thereon computer executable instructions for execution by the one or more processors. The memory may have stored thereon instructions for operating the one or mom robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console 420 or a separate imaging console (such as imaging console 490 shown in FIG. 2), wherein the one or more console processors may be configured to execute instructions for controlling movement of the one or more robotic arms, and may communicate the instructions to the robotic arms via communication circuitry (such as communication circuitry 422 of console 420 or communication circuitry 494 of console 490 shown in FIG. 2). The computer executable instructions for controlling movement of the robotic arms may be pre-programmed and stored on a memory, or may be provided by a user via one or more user inputs before or during treatment of the patient using the treatment system.

The one or more computing devices operably coupled with the first and/or second robotic arms may be configured to control movement of the arms so as to adjust the pitch, yaw, roll, and/or linear position of the treatment probe and/or imaging probe along the target site.

The mobile base 470 may comprise one or more user input devices to enable a user to control movement of the robotic arms under computer instructions. For example, as shown in FIGS. 4A and 4B, the mobile base may comprise a keyboard 474 and/or a footswitch 471, the footswitch operably coupled with the mobile base via a footswitch cable 472. The keyboard 474 and the footswitch 471, independently or in combination, may be configured to control operation of the first robotic arm 442 and/or the second robotic arm 444, for example via articulation of one or both robotic arms at one or more joints. The keyboard and the footswitch may be in communication with the one or more processors configured to control movement of the robotic arms. When a user inputs instructions into the keyboard and/or the footswitch, the user instructions can be received by the one or more processors, converted into electrical signals, and the electrical signals may be transmitted to the one or more computer-controllable actuators operably coupled with the one or more robotic arms. The keyboard and/or the footswitch may control movement of one or both arms towards or away from a treatment position, a position of interest, a predetermined location, or a user-specified location, or any combination thereof.

Optionally, the keyboard 474 and the footswitch 471, independently or in combination, may be configured to control operation of the treatment probe 450 and/or imaging probe 460. For example, the keyboard 474 and/or footswitch 471 may be configured to start, stop, pause, or resume treatment with the treatment probe. The keyboard 474 and/or footswitch 471 may be configured to begin imaging or freeze, save, or display on the display 425 an image or sequence of images previously or currently acquired by the imaging probe.

The mobile base 470 and the mobile support 480 of the console 420 may be independently positionable around a patient, supported by a patient support 449 such as a platform. For example, the mobile base 470, supporting the first and second robotic arms and the treatment and imaging probes, may be positioned between the patient's legs, while the mobile support 480 carrying the console 420 and the display 425 may be positioned to the side of the patient, such as near the torso of the patient. The mobile base 470 or the mobile support 480 may comprise one or more movable elements that enable the base or the support to move, such as a plurality of wheels. The mobile base 470 may be covered with sterile draping throughout the treatment procedure, in order to prevent contamination and fluid ingress.

Figure 5B:
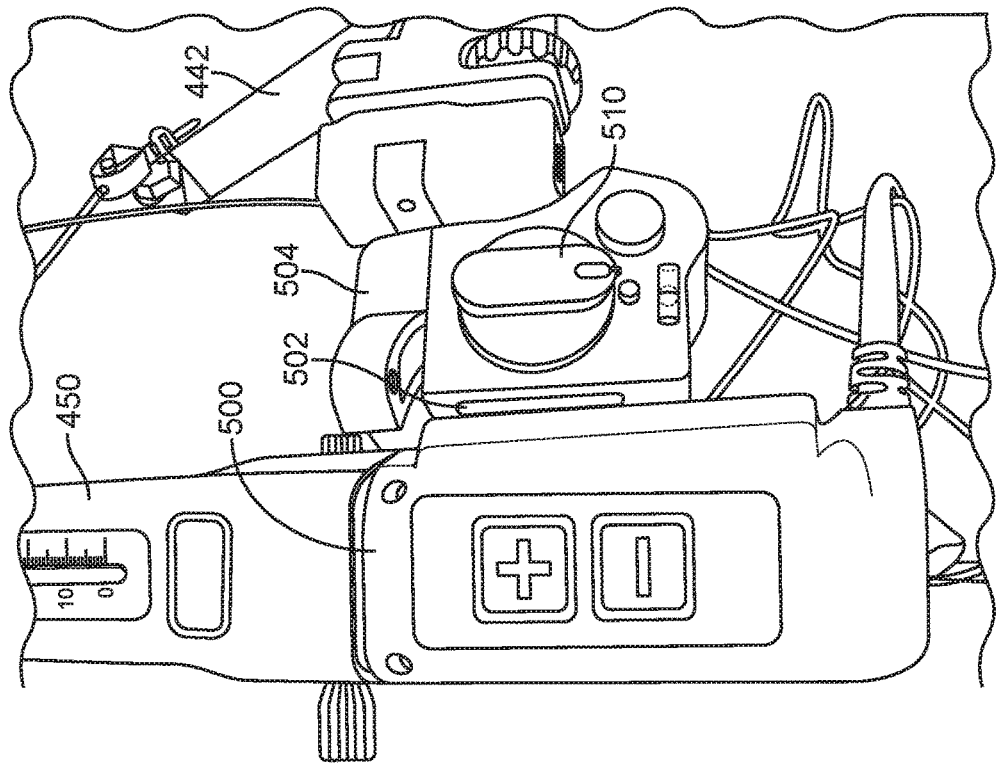
FIGS. 5A and 5B show top views of a coupling between a treatment probe and a first robotic arm, in accordance with some embodiments, with FIG. 5A showing the treatment probe and the first robotic arm uncoupled and FIG. 5B showing the treatment probe and the first robotic arm coupled.
Figure 5A:
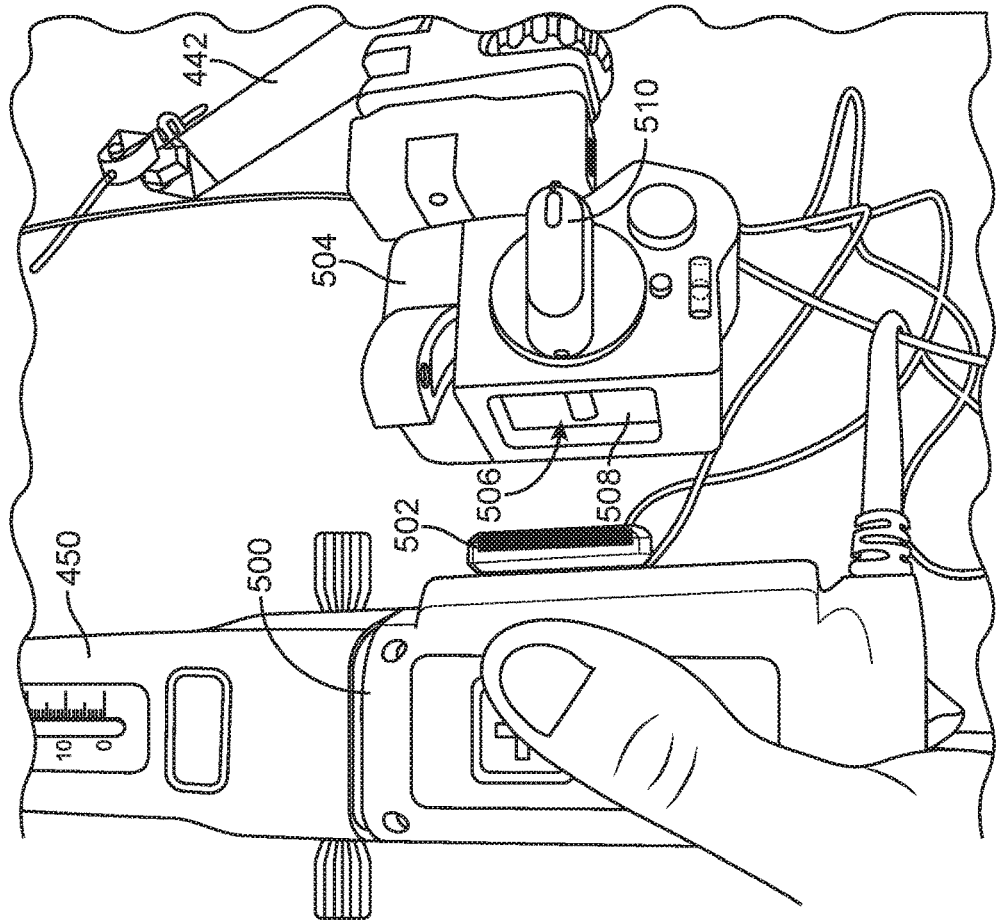

FIGS. 5A-5B show an exemplary coupling between a treatment probe 450 and a first robotic arm 442. FIG. 5A shows the treatment probe uncoupled from the robotic arm. FIG. 5B shows the treatment probe coupled to the robotic arm. As shown, the treatment probe 450 may be coupled to the robotic arm 442 with an attachment device 500 which may comprise a reusable motor pack. The treatment probe 450 may be removably coupled to the attachment device 500. The attachment device may further comprise a connector 502 configured to couple to the robotic arm and lock the attachment device in place. The robotic arm 442 may comprise a coupling structure 504 disposed at the distal end of the arm, configured to lockingly receive the connector 502 of the attachment device 500. Once the treatment probe and the robotic arm are coupled together, movement of the treatment probe may be controlled by moving the robotic arm (e.g., by articulating one or more joints of the robotic arm under computer control).

In some embodiments, the treatment probe is coupled to the robotic arm via a quick release mechanism, such that the coupling between the probe and the robotic arm is capable of a quick disconnect in order to prevent injury to the patient in case the robotic arm loses position or otherwise fails to operate correctly. The treatment probe and the robotic arm may be coupled to one another in many ways such as mechanically (e.g., a broom clip) and/or magnetically. For example, in the embodiment shown in FIGS. 5A and 5B, the coupling structure 504 may comprise a slot 506 having a magnet 508 disposed therein, and the connector 502 may comprise a ferromagnetic fixture configured to fit within the slot 506 to engage the magnet 508. The coupling structure 54 may further comprise a latching mechanism 510 to selectively engage or disengage the connector 502 with the magnet 508. For example, as shown in FIGS. 5A and 5B, the latching mechanism 510 may comprise a rotatable knob that can be rotated to affect engagement of the magnet 508 of the coupling structure 504 with the connector 502 of the attachment device 500. The latching mechanism may be automatically or manually engaged or disengaged by a user to couple or de-couple, respectively, the attachment device 500, and hence the treatment probe 450 coupled thereto, to the robotic arm 442. In some embodiments, the coupling structure 504 may be operably coupled with the one or more computing devices configured to control the robotic arm, and the one or more computing devices may comprise instructions to release the coupling of the coupling structure to the probe when an error is detected in the operation of the robotic arm.

In some embodiments, the first robotic arm 442 may be configured to automatically locate the treatment probe 450 in response to sensor location data from one or more of the attachment device 500 or coupling structure 504. The first robotic arm 442 may be operated in a "seek" mode, for example, to locate the attachment device 500. In some embodiments, the probe comprises one or more fiducial targets and the robotic arm comprises corresponding sensors of sufficient resolution and positioning to identify the relative position of the probe in 3D space. In some embodiments, the processor is configured with instructions to seek the treatment probe or imaging probe with the mounting structures on the robotic arm while the user holds the probe stead, for example when the probe has been positioned in the patient.

Figure 8A:
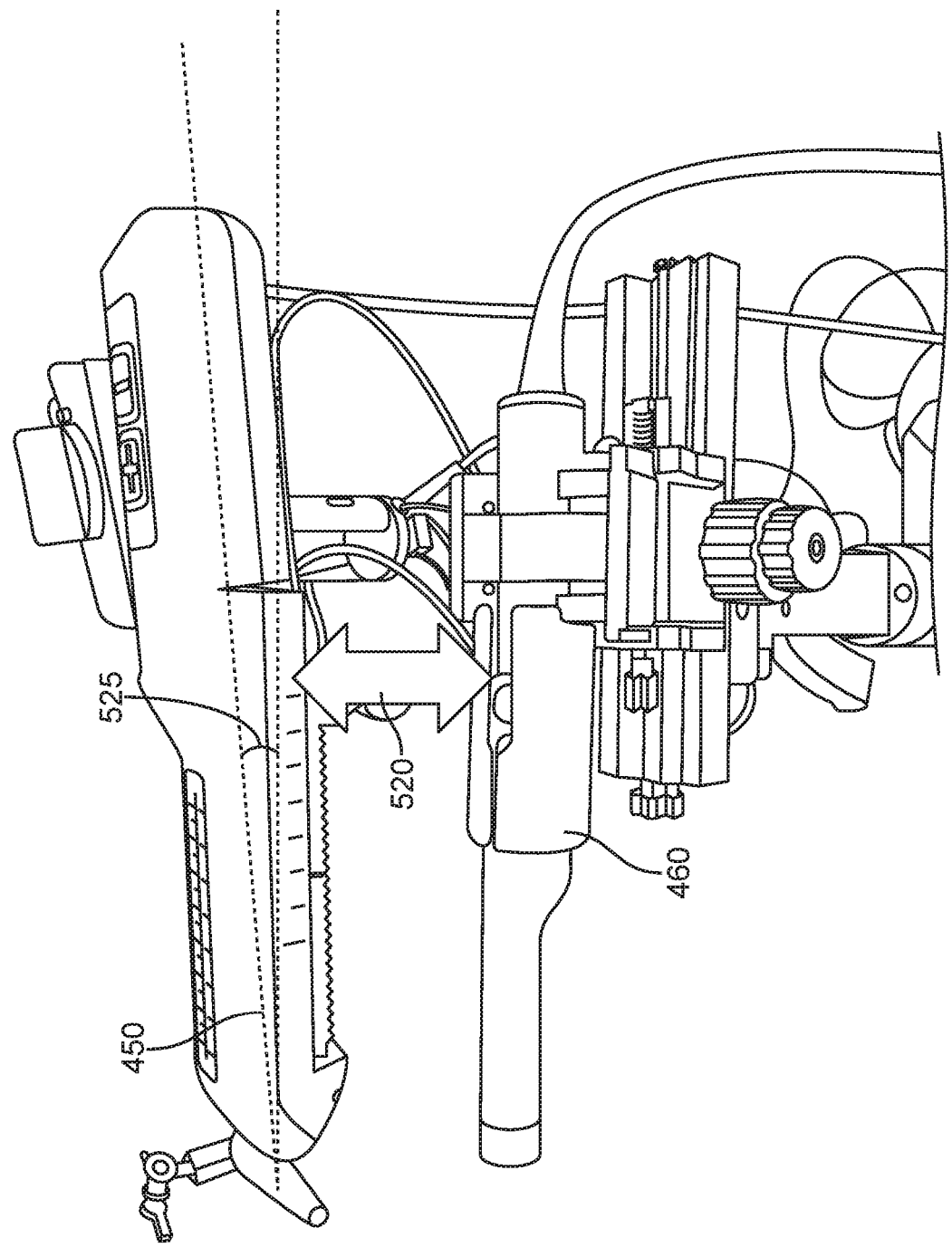
FIG. 8A illustrates a configuration of a treatment probe and an imaging probe during treatment of a patient, in accordance with some embodiments.
Figure 8B:
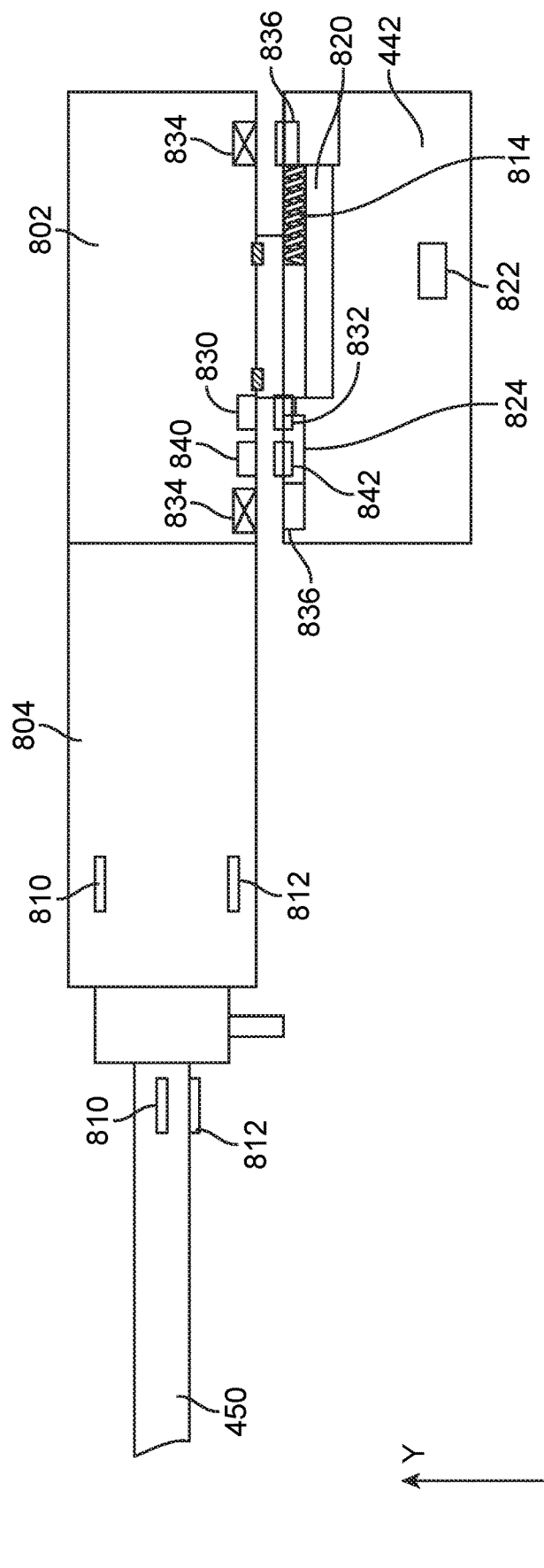
FIG. 8B is a schematic illustration of a probe and a robotic arm with force detection sensors, in accordance with some embodiments.

The sensors on the robotic arm such as the first robotic arm 442 and sensors on the probe such as the treatment probe can be arranged in many ways, for example as shown in FIG. 8B.

The processor can be coupled to the sensors near the end of the robotic arm or on the probe to dynamically update the relative location during the movement of the robot arm while seeking to engage the probe on the arm. The sensors on the robotic arm may comprise a plurality of sensors comprising one or more of capacitive, capacitive displacement, doppler, inductive, magnetic, optical, radar, sonar, ultrasonic or Hall effect sensors, in order to determine relative distances between the robotic arm and the probe. In some embodiments the probe comprises a plurality of targets and the sensors are configured to generate signals in response to distances from the plurality of targets. Alternatively or in combination, the sensors can be located on the probe and the targets on the robotic arm. In some embodiments, the sensors comprise close contact mechanical sensors to confirm docking of the probe on the robotic arm or in proximity to the arm, for example to sense the position of the probe in relation to the robotic arm when the probe and arm are within a few millimeters of docking with each other. The close contact mechanical sensors may comprise one or more of micro-motion switches, whisker touch sensors, or a pin-in-hole contact switch. In some embodiments, the probe and robotic arm comprise an integrated locking mechanism to provide a non-movement locking engagement at the final position of contact. The integrated locking mechanism may comprise one or more of magnetics, electromagnetics, a latching, screw such as a multi turn latching screw or quarter turn locking screw, a vacuum, or other mechanical means of reversible attachment as will be understood by one of ordinary skill in the art.

In some embodiments, a plurality of sensors is used, such as one or more sensors for near, one or more sensors for intermediate and one or more sensors for far separation distances between the probe and the robotic arm. A coarse location sensor can be used to determine the approximate location of the probe, e.g. a beacon. One or more sensors can be used for fine location positioning of the probe in relation to the robotic arm, e.g. proximity sensors. In some embodiments, one or more markers on the probe are used with a camera and machine vision detection of the one or more markers.

In some embodiments, coarse location sensors may be provided which may be an infrared (IR) beacon which enables the coarse positional spatial location for homing detection of the robotic arm to the probe. In some cases, a homing beacon, such as an IR beacon, allows for homing across larger distances as compared to a sensor that may rely on visual recognition of fiducials.

In some embodiments, a docking detection sensor confirms that the robotic arm has engaged or is in close proximity with a probe. As an example, a Hall effect sensor can be used in conjunction with a permanent magnet to affect the sensors output. In some embodiments, a Hall effect sensor is noise immune, non-contact, and has a consistent detection range. Any of a number of different types of Hall sensors may be utilized, and in many cases, the sensor functions as a simple switch and linear range measurement and detection in which the overall output voltage is set by the supply voltage and varies in proportion to the strength of the magnetic field. This results in a distance measurement between the sensor and a locating magnet and may be used to measure the distance between the robotic arm and the probe and aid in docking. The sensor and beacon may be located within respective housings of the robotic arm and probe.

In some embodiments, positional sensing of the robotic arm is performed by an inertial measurement unit (IMU), which may include up to 9-axis detection. In some cases, a 6-axis IMU can be used for motion detection, vibration detection, positional orientation information, redundancy and backup of the primary encoder signals that may be located in the joints of the robotic arms. The IMUs may perform a dual function of seeking a probe for docking with the robotic arm as well as force detection and motion compensation as described herein. The described sensors can be used in combination with any robotic arms or probes described herein.

According to some embodiments, the procedure for docking a robotic arm with a probe may comprise an IR beacon to provide coarse positional and spatial location for homing detection, fiducials on either the arm or the probe and an optical sensor to view the fiducials which can be used to allow fine alignment of positional location in the XY plane, and a Hall effect sensor to detect Z direction proximity for docking. An IR beacon allows for larger distance seek for the home position of the robotic arm relative to the probe. The fiducials and optical sensor may allow for rapid, low-latency detection of the 2D location and 2D orientation of the probe by the robotic arm. A user interface, which may be located on the robotic arm, on the probe, or on a robotic arm control unit, may indicate distance, position, docked status or other information. In some embodiments, the user interface includes one or more visual cues, such as LED indicators, to indicate the relative position and/or docking status of the arm and probe.

While the coupling mechanism shown in FIGS. 5A and 5B is described in the context of coupling the treatment probe to the first robotic arm, a substantially similar mechanism may also be used for coupling the imaging probe to the second robotic arm 444. For example, the coupling structure of the second robotic arm 444 may comprise a similar coupling mechanism for engaging an attachment device connected to the imaging probe.

Figure 6:
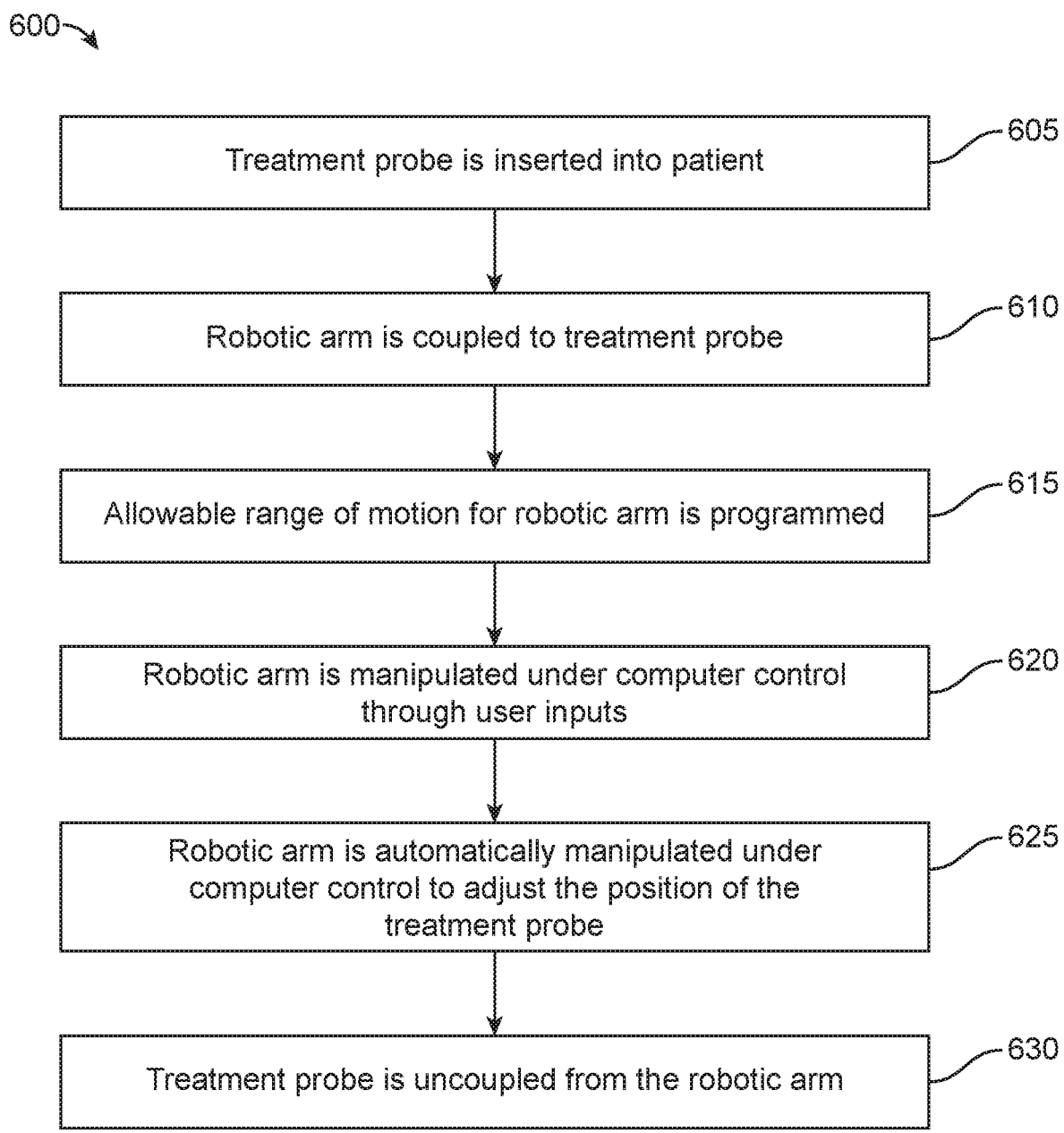
FIG. 6 shows a flow chart for a method of operating a robotic arm coupled to a treatment probe, in accordance with some embodiments.

FIG. 6 shows a method 600 for operating a robotic arm coupled to a treatment probe in accordance with some embodiments.

With a step 605, a treatment probe is inserted into the patient, with the robotic arm on standby to one side of the patient, manually, semi-automatically, or automatically. For example, for a prostatic tissue resection system, the treatment probe may be manually inserted into the urethra of the patient towards the prostate. The treatment probe may be manipulated as it is advanced to track the tortuous path of the urethra, prostate, and bladder neck. After entering the urethra, the treatment probe may be turned (e.g., by 90 degrees) before further advancement through the urethral bulb. Instructions may be provided to the user to perform such a turn, or in cases where insertion is automatic or semi-automatic, the robotic arm may be instructed to make such a turn in response to image, position, and/or force feedback data. In some embodiments, the treatment probe is inserted into the patient concurrently with or after the imaging probe, and in some instances, the treatment probe insertion may be guided by image data from the inserted image probe.

With a step 610, the robotic arm is coupled to the treatment probe. A user can manually align the robotic arm coupling structure to the attachment device of the treatment probe as described herein, while the robotic arm remains in a passive or "zero-gravity" mode. The attachment device and the coupling structure of the robotic arm can couple together in to attach the robotic arm to the treatment probe.

With a step 615, the allowable range of motion for the robotic arm is programmed. For example, a user can manually move, rotate, and angulate the treatment probe to set the boundaries for the allowable range of motion of the treatment probe, while the probe is connected to the robotic arm with the robotic arm still in passive mode. The user may set the boundaries based on a combination of cystoscopic, ultrasound, and haptic feedback. Alternatively, the boundaries may be based on anatomy such as anatomical models or tissue conditions. The processor operably coupled with the robotic arm can detect and store the boundaries for the allowable range of motion, such that the robotic arm, when switched to active mode, can use these boundaries to avoid moving outside of the allowable range of motion.

In some embodiments, a treatment probe is manually inserted within a penile urethra and placed with the distal end about 1 cm past the medium lobe and within a bladder of the patient. The probe can be imaged, for example with ultrasound such as a TRUS probe. The images of the probe may show the probe manually positioned near the final location in the patient anatomy, for example about 1 cm past the median lobe within the bladder. In some embodiments, the range of motion is manually calibrated by the medical practitioner manipulating the probe parallel to an angle of initial insertion docking the treatment probe upward in the pubic or urethral arch and restricting motion to within a range from about 3 mm to about 5 mm laterally in the X plane, within a range from about 0 mm to 10 about mm downward in the Y plane. The trained motion for the Z plane (into and out of the patient) would be set to zero cm inward toward the patient and full extraction out of the patient. For example a 30 cm probe could be retracted as much as 30+ cm to remove it from the patient and much less if adjusting the effective area for clinical treatment. Angularly, as measured from the physician's full insertion position, the range of safe motion within the patient depends on anatomic structures such as tissue elasticity and bony structure. An example of angular positioning with the fulcrum at the pelvic notch bone structure the allowable angular range of motion can be set to be within a range from about 0 degrees to about +/−5 degrees in the lateral X direction, within a range from about zero degrees to +/−25 degrees in the vertical direction along a Y plane, or a combination of motions within these ranges depending on the patient anatomy, for example.

Alternatively or in addition, the boundaries for the allowable range of motion of the treatment probe may be automatically or semi-automatically determined with one or more system processors in response to an automated analysis of image data of the target site such as from the imaging probe or other imaging source (e.g., a cystoscope, an external ultrasound source, a CT scanner, an MRI system, a fluoroscopic imaging system, etc.). The image data may be generated in real-time. For example, the one or more system processors may be instructed to recognize anatomy (e.g., the prostate, the external sphincter, the verumontanum, the bladder neck, etc.), and in some cases the treatment and/or imaging probes, in the image data and determine the boundaries for the allowable range of motion in response. Alternatively or in addition, the boundaries for the allowable range of motion of the treatment probe may be automatically or semi-automatically determined with one or more system processors in response to position and/or force feedback data of the treatment probe from one or more position and/or force sensors on the treatment probe and/or treatment probe robotic arm. For example, the one or more force sensors on the treatment probe and/or treatment probe robotic arm can provide tissue pressure data which may indicate areas to where probe advancement is more resisted and can present risks of tissue damage.

In some embodiments, the joint sensors within the robotic arms comprise force feedback sensors to detect force to the probe inserted into patient. Alternatively or in combination, sensors coupled to the processor can be located at one or more of the probe or at an interface between the probe and the robotic arm. For example, probe sensors within the probe can sense pressure near the distal end of the probe. The processor can be configured with instructions to adjust the distal end of the probe translationally or rotationally in response to the distal pressures sensed. The sensors may comprise one or more of multi plane strain gage elements located along the probe to sense pressures of the probe against tissue. The processor can be configured with instructions to implement threshold limits to avoid undesirable tissue damage. The multiplane strain gauge elements may comprise one or more of electrical conductance thin film sensors, semiconductor sensors, piezoresistors, nanoparticle-based strain sensors, capacitive sensors, optical ring resonators, fiber optic sensors, or conductive fluid in an elastomer. In some embodiments, a probe shaft comprises a spring constant and embedded strain gages at periodic locations along the shaft to measure bending, and axial pressure at specific points along the shaft. These sensor measurements can be combined with the arm joint sensors.

In some embodiments, the processor is configured with instructions to identifying if a source of pressure resistance, such as one or more of a bony constraint related to proximity to bone, a tough tissue entry fulcrum, or the distal tip of the probe being forced against inner anatomy tissue. Alternatively or in combination, the probe on the probe may comprise elastomeric tubular sheaths having exposed "touch areas" coupled with pressure sensors reporting information from elements such as rings around the probe, a linear side structure, or button sensor elements near the distal end of the probe.

With a step 620, the robotic arm is manipulated under computer control through user inputs. The user may manipulate the robotic arm motion via inputs provided to the graphic user interface of the image-guided treatment system (e.g., user interface software provided through the treatment console as described herein). For example, the user may affect rotation, translation, and/or adjustment of pitch angle of the treatment probe. While in active mode, the robotic arm may be configured to move only within the boundaries of allowable range of motion as set in step 615. The robotic arm, while in active mode, may be configured to retract the treatment probe from the patient, but not advance the treatment probe into the patient, to ensure safety of the patient; any advancement of the probe into the patient can be performed manually by the user. During retraction of the probe, the robotic arm may be programmed to maintain the probe on a linear track so that the z-axis position of the probe remains substantially constant. The robotic arm and the treatment probe may be manipulated under computer control to perform a treatment protocol, which may be automated. In some embodiments, a tissue resection procedure is automatically planned based on the image data from the imaging probe or other imaging source. For example, the one or more system processors may be instructed to recognize the prostate or other relevant anatomy thereof, generate a treatment protocol in response to the locations of the anatomy and probes, and allow the user to modify and/or accept the treatment protocol before it is implemented by manipulating the robotic arm and/or treatment probe.

With a step 625, the robotic arm is automatically manipulated under computer control to adjust the position of the treatment probe. The position of the treatment probe may be adjusted according to pre-programmed parameters, user instructions, real-time feedback (from imaging, position, and/or force feedback data, for example), or combinations thereof. For example, the imaging system may be configured to detect the location of the treatment probe during treatment, for example using smart image recognition based on ultrasound images of the target site obtained with an ultrasound imaging probe. Based on the detected location of the treatment probe, the robotic arm may be manipulated automatically to adjust the position and/or orientation of the treatment probe, in order to align the treatment probe to the target tissue of the patient and/or to the imaging probe and/or in order to compensate for patient movement.

With a step 630, the treatment probe is uncoupled from the robotic arm. When the treatment procedure is completed, the user can disconnect the treatment probe from the robotic arm, manually move the robotic arm to the side, and then remove the treatment probe from the patient.

One or more steps of the method 600 may be performed with circuitry as described herein, for example, one or more of a processor or a logic circuitry of the systems described herein. The circuitry may be programmed to provide one or more steps of the method 600, and the program may comprise program instructions stored on a computer readable memory or programmed steps of the logic circuitry such as with programmable array logic or a field programmable gate array.

Although the above steps show a method 600 of operating a robotic arm coupled to a treatment probe in accordance with some embodiments, a person of ordinary skill in the art will recognize many variations based on the teachings described herein. For example, the steps may be completed in a different order. One or more steps may be added or omitted. Some of the steps may comprise sub-steps. Many of the steps may be repeated as often as necessary or desired.

Figure 7:
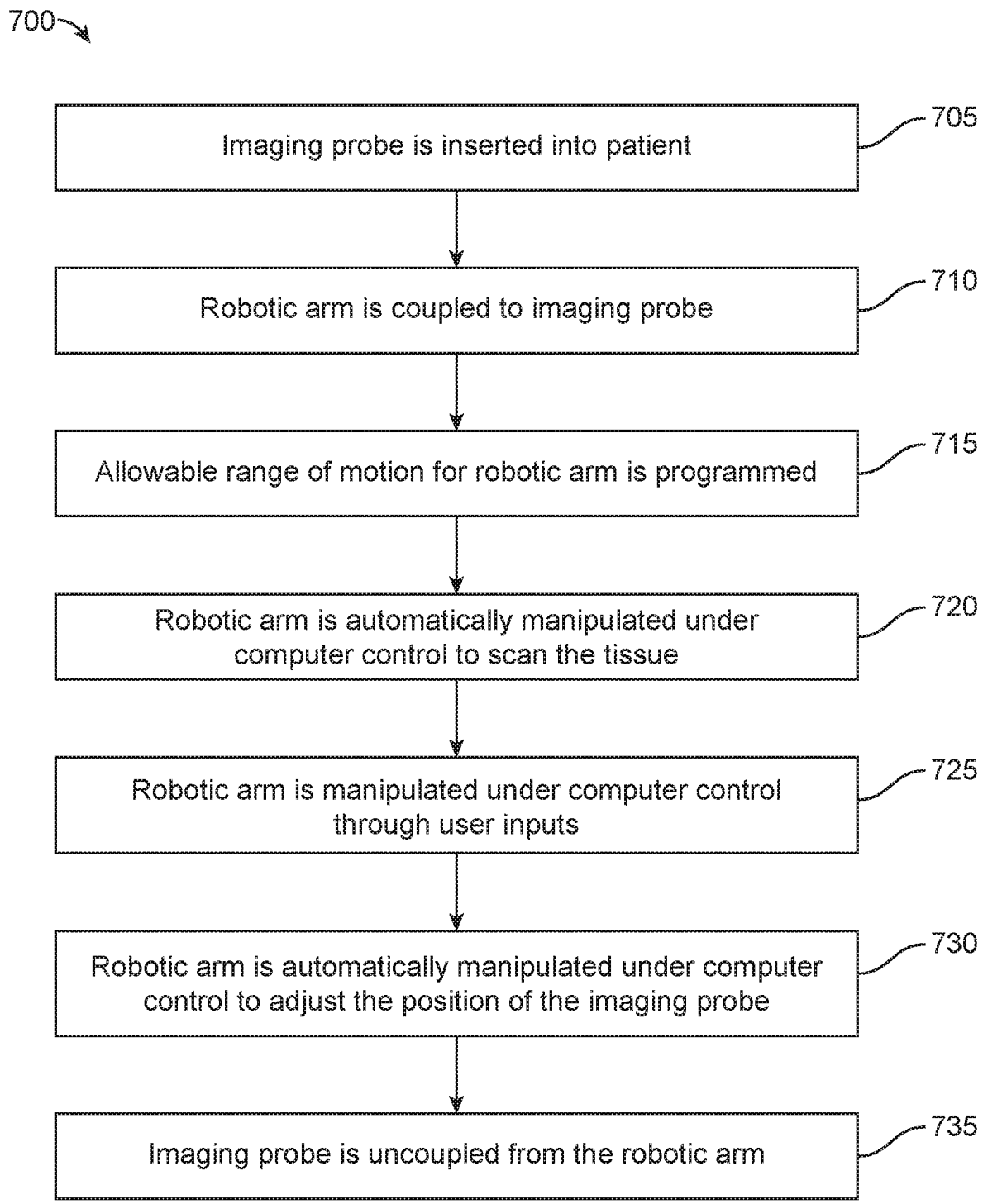
FIG. 7 shows a method for operating a robotic arm coupled to an imaging probe in accordance with some embodiments.

FIG. 7 shows a method 700 for operating a robotic arm coupled to an imaging probe in accordance with some embodiments.

With a step 705, an imaging probe is inserted into the patient, with the robotic arm on standby to one side of the patient, manually, semi-automatically, or automatically. For example, for an image-guided prostatic tissue resection system, the imaging probe may comprise a TRUS probe and may be manually inserted into the rectum of the patient. In some embodiments, the imaging probe is inserted concurrently with or before the treatment probe. The imaging probe may provide one or more images along the transverse plane. The imaging probe may provide one or more images along the sagittal plane which may be generated as the imaging probe (and/or an imaging transducer within the imaging probe) is advanced and/or retracted. The transverse and/or sagittal images may be combined to generate a three-dimensional image.

With a step 710, the robotic arm is coupled to the imaging probe. For example, the robotic arm and the imaging probe may be coupled together using a coupling mechanism substantially similar to that described herein with reference to the treatment probe.

With a step 715, the allowable range of motion for the robotic arm is programmed. For example, a user can manually move, rotate, and angulate the imaging probe to set the boundaries for the allowable range of motion of the imaging probe, while the probe is connected to the robotic arm with the robotic arm still in passive mode. The user may set the boundaries based on a combination of cystoscopic, ultrasound, and haptic feedback.

In some embodiments, a probe is manually positioned near the final location in the patient's rectal anatomy. The range of motion is manually calibrated by the medical practitioner manipulating the probe substantially parallel to an angle of initial insertion, for example. The medical practitioner moves the inserted probe within a range of allowable motion, for example an allowable range of motion with boundaries within a range from about 3 cm to about 5 cm along one or more of the lateral X plane or the vertical Y plane. In some embodiments, the medical practitioner moves the probe along the Z plane (into and out of the patient). In some embodiments the range of motion along the Z plane can be within a range from 0 cm inward toward the patient (zero to avoid inadvertent robotic caused rectal damage) to full extraction out of the patient. For example a 10 cm probe could be retracted 10+ cm to remove it from the patient. Angularly, as measured from the physician's full insertion position, the range of safe motion within the patient depends on anatomic structures such as tissue elasticity and bony structure. An example of angular positioning of the probe with the fulcrum at the tissue surface (or alternatively at planes defined by bone structure), the allowable range of motion can be set from 0 to about +/−15 degrees, for example from about 0 to about +/−30 degrees in one or more of the X or Y planes. In some embodiments, the angular boundary may comprise a combination of motions corresponding to tracing a cone within these boundaries.

The processor operably coupled with the robotic arm can detect and store the boundaries for the allowable range of motion, such that the robotic arm, when switched to active mode, can use these boundaries to avoid moving outside of the allowable range of motion. Alternatively or in addition, the boundaries for the allowable range of motion of the imaging probe may be automatically or semi-automatically determined with one or more system processors in response to an automated analysis of image data of the target site such as from the imaging probe or other imaging source (e.g., a cystoscope, an external ultrasound source, a CT scanner, an MRI system, a fluoroscopic imaging system, etc.). The image data may be generated in real-time. For example, the one or more system processors may be instructed to recognize anatomy (e.g., the prostate, the external sphincter, the verumontanum, the bladder neck, etc.), and in some cases the treatment and/or imaging probes, in the image data and determine the boundaries for the allowable range of motion in response. Alternatively or in addition, the boundaries for the allowable range of motion of the imaging probe may be automatically or semi-automatically determined with one or more system processors in response to position and/or force feedback data of the imaging probe from one or mom position and/or force sensors on the imaging probe and/or treatment probe robotic arm. For example, the one or more force sensors on the imaging probe and/or imaging probe robotic arm can provide tissue pressure data which may indicate areas to where probe advancement is more resisted and can present risks of tissue damage.

With a step 720, the robotic arm is automatically manipulated under computer control to scan the tissue. For example, during the planning of the treatment procedure, the robotic arm can be pre-programmed to automatically scan the target site to render a 3-dimensional image of the target site. While in active mode, the robotic arm may be configured to move only within the boundaries of allowable range of motion as set in step 715. The robotic arm, while in active mode, may be configured to retract the treatment probe from the patient, but not advance the treatment probe into the patient, to ensure safety of the patient; any advancement of the probe into the patient can be performed manually by the user. During retraction of the probe, the robotic arm may be programmed to maintain the probe on a linear track so that the z-axis position of the probe remains substantially constant.

With a step 725, the robotic arm is manipulated under computer control through user inputs. The user may manipulate the robotic arm motion via inputs provided to the graphic user interface of the image-guided treatment system (e.g., user interface software provided through the treatment or imaging console as described herein). For example, the user may affect rotation, translation, and/or adjustment of pitch angle of the imaging probe. While in active mode, the robotic arm may be configured to move only within the boundaries of allowable range of motion as set in step 715. The robotic arm, while in active mode, may be configured to retract the treatment probe from the patient, but not advance the treatment probe into the patient, to ensure safety of the patient; any advancement of the probe into the patient can be performed manually by the user.

With a step 730, the robotic arm is automatically manipulated under computer control to adjust the position of the imaging probe. The position of the imaging probe may be adjusted according to pre-programmed parameters, user instructions, real-time feedback (from imaging, position, and/or force feedback data, for example), or combinations thereof. For example, the imaging system may be configured to detect the location of the treatment probe during treatment, for example using smart image recognition based on ultrasound images of the target site obtained with an ultrasound imaging probe. Based on the detected location of the treatment probe, the robotic arm may be manipulated automatically to adjust the position and/or orientation of the imaging probe, in order to align the imaging probe to the treatment probe and/or in order to compensate for patient movement.

With a step 735, the imaging probe is uncoupled from the robotic arm. When the treatment procedure is completed, the user can disconnect the imaging probe from the robotic arm, manually move the robotic arm to the side, and then remove the imaging probe from the patient.

One or more steps of the method 700 may be performed with circuitry as described herein, for example, one or more of a processor or a logic circuitry of the systems described herein. The circuitry may be programmed to provide one or more steps of the method 700, and the program may comprise program instructions stored on a computer readable memory or programmed steps of the logic circuitry such as with programmable array logic or a field programmable gate array.

Although the above steps show a method 700 of operating a robotic arm coupled to an imaging probe in accordance with some embodiments, a person of ordinary skill in the art will recognize many variations based on the teachings described herein. For example, the steps may be completed in a different order. One or more steps may be added- or omitted. Some of the steps may comprise sub-steps. Many of the steps may be repeated as often as necessary or desired.

FIG. 8A illustrates a configuration of a treatment probe 450 and an imaging probe 460 during treatment of a patient with the treatment system as described herein. In some embodiments, it is desirable to ensure that the treatment probe and the imaging probe outside of the patient body do not collide or otherwise interfere with one another during use of the system, thereby maintaining the precision of movement of the probes and sterility of the system. The robotic arms as described herein, coupled to the treatment probe and the imaging probe and configured to control their movement, may be configured to maintain boundaries to prevent collision or interference between the two probes. For example, one or both of the first robotic arm coupled to the treatment probe and the second robotic arm 444 coupled the imaging probe may be configured to sense a distance 520 between the two probes, and maintain the distance substantially constant or greater than a minimum threshold value to prevent collision. Alternatively or additionally, as described with reference to the methods shown in FIGS. 6 and 7, the user may program an allowable range of motion for one or both of the treatment probe and the imaging probe so as to set boundaries for the range of motion that would prevent collision or interference between the probes.

For example, before the robotic arms are switched to active mode, the user may rotate one or both of the probes over a range of allowable pitch angles 525 of the probes to program the allowable range of motion for the probes within which the two probes do not contact one another.

With additional reference to FIG. 8B, the robotic arm 442 is coupled to a motor pack 802, as described herein. The motor pack 802 may be coupled to a hand piece 804 of a probe 450. In some embodiments, one or both of the robotic arms coupled to the treatment probe and the imaging probe may comprise one or more feedback sensing mechanisms.

For example, the first robotic arm 442 and/or the second robotic arm 444 may be operably coupled with a force sensor configured to detect a compression of the tissue anterior to the treatment probe and/or imaging probe. In some embodiments, the force exerted by the imaging probe is within a range from 0 to 4 kg exerted upward compressing the tissue to achieve visualization of the treatment probe and target tissue region. In some embodiments, the force exerted by the treatment probe is related to the position of the probe within the lumen such as the urethra. In some embodiments the force is related to a fulcrum at the urethral notch and a pivoting to lift the target anatomy. These forces can be, respectively, within a range from 0 to 10 kg against the bony structure and within a range from 0 to 2 kg force on the target anatomy such as the prostate.

According to some embodiments, one or more X-direction force sensors 810, one or more Y-direction force sensors 812, and/or one or more Z-direction force sensors 814 may be provided on the robotic arm 442, the hand piece 804, and/or the probe 450. The one or more force sensors may comprise a strain gauge, a pressure sensor, or a piezo electric transducer, for example. In some embodiments the strain gauge comprises any of a number of configurations of a Wheatstone bridge. A Wheatstone bridge circuit converts a small change in resistance into a measurable voltage differential, which can be equated to an applied force. The force sensor may be coupled to the handpiece, such as any hand piece embodiment described herein. In some instances, one or more force sensors are operatively coupled to the imaging probe, treatment probe, or both.

In some embodiments, the circuitry for operating the force sensor is insulated and isolated from the imaging probe and treatment probe. This allows the probe to satisfy any patient leakage current requirements, and reduces any noise that would be picked up by the probe, thus enhancing the signal to noise (S/N) of the force sensor. In some embodiments, the signal wires from the force sensor may be twisted together and optionally may be shielded to maintain signal integrity, improve immunity, and maintain an adequate S/N ratio. The force sensor may be formed of any suitable material, and in some cases, is formed of a biocompatible material for portions of the sensor that may come into contact with a patient before, during, or after treatment.

In some embodiments, one or more force sensors are sized to fit on or within the probe shaft, such as the imaging probe or treatment probe shaft. The force sensor may be configured with any suitable strain sensitivity "k," which is a proportional factor between the relative change of the resistance. The strain sensitivity is a figure that is dimensionless and is called the Gage Factor ("GF"). A linear pattern strain gauge may be used to measure strain in a single direction on the handpiece. Conductive signal wires may be bonded to the pads of the sensor which carry the signal to an input amplifier. One or more sensors may be bonded to one or more probes on a carrier substrate that may insulate the sensor from any metal of the probe, such as a metal probe shaft.

Displacement in the Z-direction of the handpiece can be detected by a spring and sensor 814. Utilizing this configuration, the entire probe assembly can be able to slide a suitable distance to provide protection from a probe being driven into a tissue wall. The probe assembly may be arranged on a sliding trolley 820 which can be sprung against a simple spring to provide a constant and known force "K" spring constant. Accurate distance measurement of the handpiece, such as my displacement of the trolley, is possible over a short distance with a suitable arrangement such as less than 2 inches. Other positional encoder linear sensors may be used in combination, or in the alternative. For example, a linear variable differential transformer (LVDT), is an electromechanical sensor used to convert mechanical motion into a variable electrical current, and can be used to measure resistance to the insertion force of the probe. An optical encoder, or any of a number of suitable inductive linear encoders. A sensor can measure a force based upon an inductive linear encoder 824, and may be arranged for non-contact to ensure high reliability. A high-resolution encoder 824 may be provided for a linear resolution of between about 15 micrometers for a digital encoder, to about 54 micrometers, such as for an analogue encoder.

One or more sensors may be provided on one or more robotic arms to measure position, orientation, force, or some other parameter. In some instances, two sensors may be part of the robotic arm assembly and can be utilized to determine unintended movements. These sensors can be internal encoders which may be located one or more joints of the robotic arm and may be an inertial measurement unit (IMU) 822. An IMU is an electronic sensor device that measures and reports one or more parameters, such as a force, an angular rate, and/or the orientation of the sensor, and may use a combination of accelerometers, gyroscopes, and/or magnetometers. Some IMUs that are suitable for incorporation into one or more robotic arms may have a full-scale acceleration ranges of $\pm 2/\pm 4/\pm 8/\pm 16$ g ("g" values in relation to acceleration due to gravity) and a wide angular rate ranges of $\pm 125/\pm 250/\pm 500/\pm 1000/\pm 2000/\pm 4000$ degrees per second ("dps"). The IMUs can detect forces on the robotic arm and communicate the magnitude and/or direction of an external force to the computing devices, such as a robotic control system. The one or more IMUs 822 can provide feedback which can be used to control the one or more robotic arms to compensate for vibration, positional awareness, and stabilization compensation.

As described herein, the robotic arm 442 can be docked with the probe 450 by the use of sensors to aid in one or more of coarse positional alignment, intermediate positional alignment and fine positional alignment. For example, the probe may be associated with a beacon 830, such as an IR beacon, and the robotic arm 442 may carry an IR receiver 832 that is able to detect an emission from the IR beacon 830 for coarse alignment. One or more alignment fiducials 834 may be associated with the probe 450 and one or more alignment sensors 836 may be associated with the robotic arm 442. The alignment sensors 836 are able to detect the position of the alignment fiducials, and thus determine the position of the robotic arm 442 relative to the probe 450, as described herein. In some embodiments, proximity sensors such as Hall effect sensors or proximity switches are used to detect the alignment between the probe and the arm in order to engage the probe with the arm, for example to latch the probe onto the arm when the arm has been suitably manipulated into position.

In some embodiments, when the treatment has been completed, the arm can be decoupled from the probe while the user holds the probe, and the arm drawn away from the probe, for example automatically drawn away from the probe.

The one or more computing devices operably coupled with the robotic arms (such as the processor of the console 420 or console 490 as described herein) may comprise instructions to control movement of the robotic arms in response to forces detected by the sensor, for example to prevent over-compression of the anterior tissue and resultant damage to the tissue and/or the probe. In the exemplary use case of the treatment system for prostatic tissue resection, the treatment probe is ideally positioned at the anterior center of the prostate cavity of the patient, but without over compressing the anterior prostate to prevent inadvertent injury to the urethra/prostate (e.g., excessive bleeding, necrosis, perforation of tissue) and/or damage to one or both of the imaging probe and the treatment probe. Similarly, the imaging probe, which can be a TRUS probe, is ideally positioned within the rectum of the patient with adequate anterior compression to view the prostate and the treatment probe, but without over compressing the tissue, so as to avoid inadvertent injury to the rectum (e.g., bleeding or perforation of the tissue) and/or damage to one or both of the imaging probe and the treatment probe. The treatment probe, the first robotic arm coupled thereto, the imaging probe, and/or the second robotic arm 444 coupled thereto may be provided with the force sensor configured to detect anterior compression of the tissue with the probe. The detected force level may be communicated to the processor operably coupled with the robotic arm, and compared to a threshold value of force pre-programmed or stored in the memory of the computing system. If the detected force exceeds the threshold, the movement of the robotic arm may be adjusted to move the probe away from the anterior tissue, thereby at least partially relieving compression of the anterior tissue.

Another exemplary feedback sensing mechanism may comprise position and/or motion sensors operably coupled with the first and/or second robotic arm 444. The one or more computing devices operably coupled with the robotic arms may comprise instructions to control movement of the robotic arms in response to the position and/or motion detected by the sensors, for example to adjust the position of the treatment and/or imaging probe in response to patient movement during a treatment and/or scanning procedure. Patient movement while a rigid element such as the treatment probe or the imaging probe is positioned inside the patient's body could potentially cause injury to the patient, and could necessitate the removal of the probe during the movement and subsequent re-positioning of the probe. A robotic arm that automatically adjusts the position of the probe in response to sensed movement of the patient can improve the safety as well as the efficiency of the procedure. One or more position or motion sensors, such as coils and/or accelerometers, may be attached to the patient, and the sensor may be operably coupled with the computing devices controlling the robotic arms. The sensors may be configured to generate small, localized electromagnetic fields or other signals to help determine the location and/or movement of the patient, for example. The processor can receive the detected patient movement data, and accordingly adjust movement of the robotic arms to substantially match patient movement, such that the probe coupled to the robotic arm can remain within an acceptable range of positions with respect to the tissue or patient organ. In some embodiments, the processor is configured to interrupt the treatment if the force to the sensor exceeds a threshold amount.

Optionally, in some embodiments, the robotic arms may be configured to automatically move in a linked manner. For example, if a user of the system moves the first robotic arm, the second robotic arm 444 may be configured to automatically adjust its position accordingly. In the exemplary use case of the treatment system for prostatic tissue resection, the prostate of the patient may not be symmetrical in anatomy, and the user may need to adjust the position or orientation of the treatment probe accordingly (e.g., push the probe to a side, adjust the pitch angle of the probe, etc.). The robotic arm coupled to the imaging probe may be configured to automatically detect adjustments made to the robotic arm coupled to the treatment probe, and make corresponding adjustments to the imaging probe position and/or orientation. Such linked movement of the two robotic arms may be useful for maintaining the treatment and imaging probes at a desired positional relationship with respect to one another, for example with the elongate axis of the treatment probe substantially aligned with the elongate axis of the imaging probe.

Figure 9A:
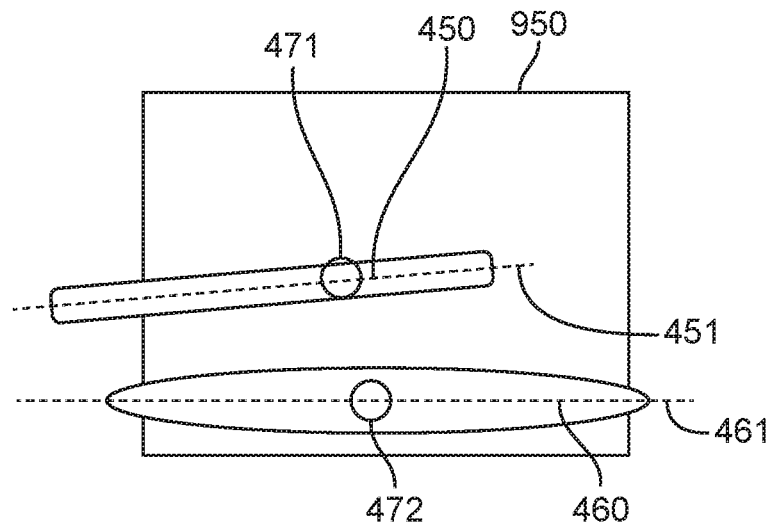
FIGS. 9A, 9B, and 9C schematically illustrate an alignment of a treatment probe axis with a sagittal plane of an imaging probe, in accordance with some embodiments.
Figure 9B:
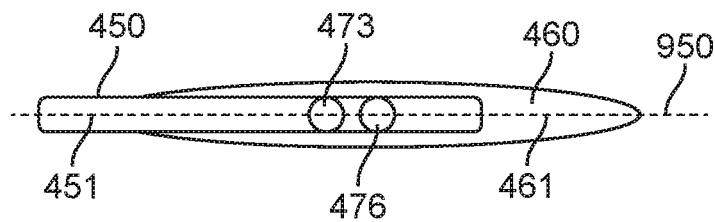
Figure 9C:
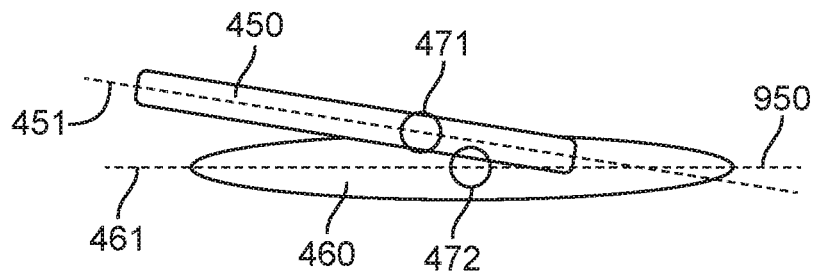

FIGS. 9A-9C schematically illustrate an alignment of a treatment probe axis 451 with a sagittal plane 950 of an imaging probe 460. FIG. 9A is a side view of a treatment probe 450 that is inclined relative to an imaging probe 460. The treatment probe 450 comprises an elongate axis 451, and the imaging probe 460 comprises an elongate axis 461 that provides a reference for the images generated by the imaging probe. The elongate axis 461 may at least partially define a sagittal image plane 950. FIG. 9B is a top view of the treatment probe 450 substantially aligned with the sagittal image plane 950. When the treatment probe axis 451 is substantially aligned with the sagittal image plane 950, a substantial portion of the treatment probe is within the field of view of the ultrasound probe and visible in the sagittal image. In some embodiments, the two probes are substantially aligned when the elongate axes are aligned to within about 5 degrees of each other with respect to a plane perpendicular to the sagittal image plane. For with greater angles of inclination between the probes, the treatment probe will extend transverse to the field of view of the ultrasound probe, and only the portion of the probe within the field of view of the ultrasound probe will be visible in the ultrasound image.

When the probes are substantially aligned within the sagittal image plane but inclined at an angle as shown in FIG. 9A the treatment probe and tissue can appear rotated in the sagittal image and the acceptable amount of rotation can be greater than 5 degrees, for example. FIG. 9C is a top view of the treatment probe 450 traversing a sagittal image plane 950. When the imaging probe is not sufficiently aligned with the treatment probe, the treatment probe can appear distorted in the sagittal plane image, with only a portion of the treatment probe extending through the sagittal field appearing in the image. In some embodiments, the treatment and imaging probes may comprise one or more sensors to confirm the desired alignment (parallel and/or coplanar) of the probes to one another. For example, the system may comprise a first orientation sensor 473, and a second orientation sensor 476 on the treatment probe 450 and the imaging probe 460, respectively. In some embodiments, the first orientation sensor, and a second orientation sensor 476 comprise magnetic elements, Hall effect sensors, dials, variable resistors, potentiometers, accelerometers, or any combination thereof that may indicate the relative position and orientation of the probes to one another. In some embodiments, the angle of the sagittal plane of the ultrasound imaging probe can be rotated by rotating the ultrasound imaging probe about the elongate axis of the ultrasound imaging probe. For example, in some patients, the prostate is not symmetrical, or the urethral notch is deformed, and imaging probe and the treatment probe can be located on opposite sides of the patient or at least offset relative to each other with respect to a midline of the patient, and rotation of the imaging probe about its elongate axis can rotate the sagittal plane of the ultrasound probe and bring the treatment probe and tissue treatment region within the field of view of the ultrasound imaging probe. The alignment, orientation, and relative positioning of the treatment and imaging probes may continue to be monitored during a treatment procedure.

When the treatment probe and the imaging probe are insufficiently aligned, the user can use images of the treatment probe obtained with the imaging probe to align the treatment probe with the imaging probe, for example by providing user inputs into the GUI for controlling the robotic arm coupled to the treatment probe or the imaging probe. Alternatively or additionally, the robotic arms may be programmed to automatically adjust movements to maintain the probes in sufficient alignment, as described herein. For example, when a user adjusts the position or orientation of the treatment probe by controlling the first robotic arm coupled to the treatment probe, the second robotic arm 444 coupled to the imaging probe may automatically detect the adjustments made to the first robotic arm and make corresponding adjustments to substantially match the pitch, roll, yaw, and or linear position of the treatment probe along the treatment probe axis.

To provide automatically linked movement of the two robotic arms, a calibration step may be added to the treatment procedure wherein each arm identifies its position with respect to the other arm. For example, each robotic arm may comprise a "target" on the arm of a known location; during the calibration procedure, the user may manipulate the first arm to touch the target located on the second arm with the first arm coupling structure, and manipulate the second arm to touch the target located on the first arm with the second arm coupling structure. Automatically linking movement of the two robotic arms can thus facilitate the treatment procedure by eliminating the need for the user to separately adjust the movement of a second arm after moving a first arm. In addition, the linked movement of the two arms can aid in improving safety and efficiency of the treatment procedure in case the patient moves while the probes are inserted into the patient's body, as described herein.

Optionally, in some embodiments, the robotic arm coupled with the treatment probe may be configured to move the treatment probe along a pre-programmed treatment profile for performing treatment of the target site. For example, the treatment profile may comprise a tissue resection profile of the target site, which may be programmed by the user of the treatment system and stored in a memory of the one or more computing devices operably coupled with the robotic arm. Further details regarding automated treatment using programmed treatment profiles may be found in PCT Publication No. WO2013/130895, previously incorporated herein by reference.

Optionally, in some embodiments, the robotic arm coupled with the imaging probe may be configured to move the imaging probe along a pre-programmed imaging profile for generating a 3-dimensional rendering of the target site, before and/or during treatment with the treatment probe. A 3-dimensional image of the target site may be derived from a biplanar imaging probe by: 1) rotating the imaging probe in place with the imaging probe capturing sagittal view images of the target site, then interpolating the sagittal view images, or 2) translating the imaging probe across the target site (along the z-axis of the probe) with the imaging probe capturing transverse view images of the target site, then interpolating the transverse view images. To improve the efficiency of 3D image rendering and the resolution of the resultant 3D images, the robotic arm may be configured to rapidly scan the target site along a pre-programmed imaging profile, and the 3D image may be generated using software to render a 3D image of the treatment site in substantially real-time. The pre-programmed imaging profile may be stored on a memory of the one or more computing devices, and may comprise a plurality of sagittal view scans taken at predetermined time intervals while the imaging probe rotates in place, and/or a plurality of transverse view scans taken at predetermined time intervals while the imaging probe translates across the target site (along the z-axis or elongate axis of the imaging probe).

The automatic, computer-controlled scanning of the target site with the imaging probe using the robotic arm can also be used to generate useful information regarding the target site for additional treatment. For example, the imaging probe may be configured to perform a color/Doppler scan of the target site after a resection procedure, in order to locate bleeding sites within the target site that require hemostasis. In some embodiments, the Doppler ultrasound image shows blood moving away from the ultrasound probe as blue and blood moving toward the ultrasound probe as red. In some embodiments, the tissue resection profile can be adjusted prior to tissue resection so as to decrease and in some instances avoid resection of blood vessels present in the Doppler ultrasound image. For example, the ultrasound image may comprise a 3D ultrasound image and a 3D resection profile adjusted to decrease or avoid blood vessels.

Figure 10:
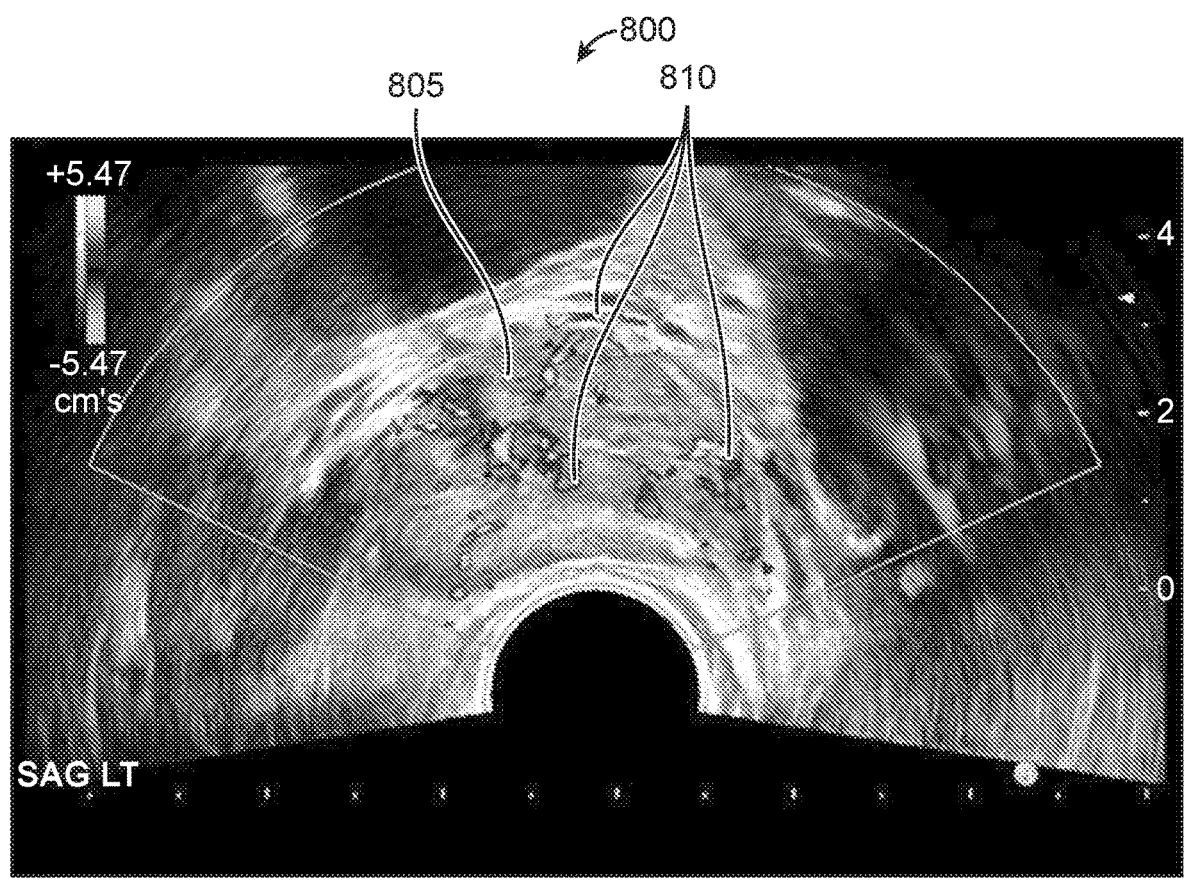
FIG. 10 shows an intra-operative image of a surgical field including the identification of bleeding sites, in accordance with some embodiments.

FIG. 10 illustrates the identification of high blood perfusion sites 810 from an ultrasound image 800 of a tissue 805 of a patient. As described herein, the robotic arm coupled to the imaging probe may be automatically moved to obtain scans from the imaging probe while the imaging probe operates in Doppler imaging mode. The high blood perfusion sites 810 can be identified from the resultant Doppler scan images, based on the detection of blood flowing closer to or farther away from an imaging plane of the imaging probe. In some cases, the high blood perfusion sites 810 comprise bleeding sites, and based on the Doppler information, the user can efficiently locate and treat the bleeding, for example by using focal cautery or hemostatic agents such as gels and matrices, thereby reducing bleeding, cautery time and heat or other effect on the tissue. The high blood perfusion sites 810 may also, in some cases, comprise abnormal or even cancerous tissue growths. These areas may be flagged or identified for subsequent treatment. For example, normal tissue may be resected around abnormal tissue to leave islands of abnormal tissue that are later treated such as with local drug delivery.

The 3-dimensional scan of the target site using the imaging probe may also be used to identify tissue anomalies at the target site, such as tumors. For example, tumors may be identified from the images of the target site obtained with the automated scanning of the target site with the imaging probe, based on differences between hyperechoic and hypoechoic areas of the imaged tissue. Robotically scanning of the target site can improve the speed of image analysis and therefore the accurate detection of tissue anomalies. In addition, the imaging probe may be operated in Doppler imaging mode during the automated scanning to identify regions of higher blood flow, which can correspond to locations of potential cancer. Biopsies may be performed at the identified regions of tissue to improve the detection of cancer.

Figure 11A:
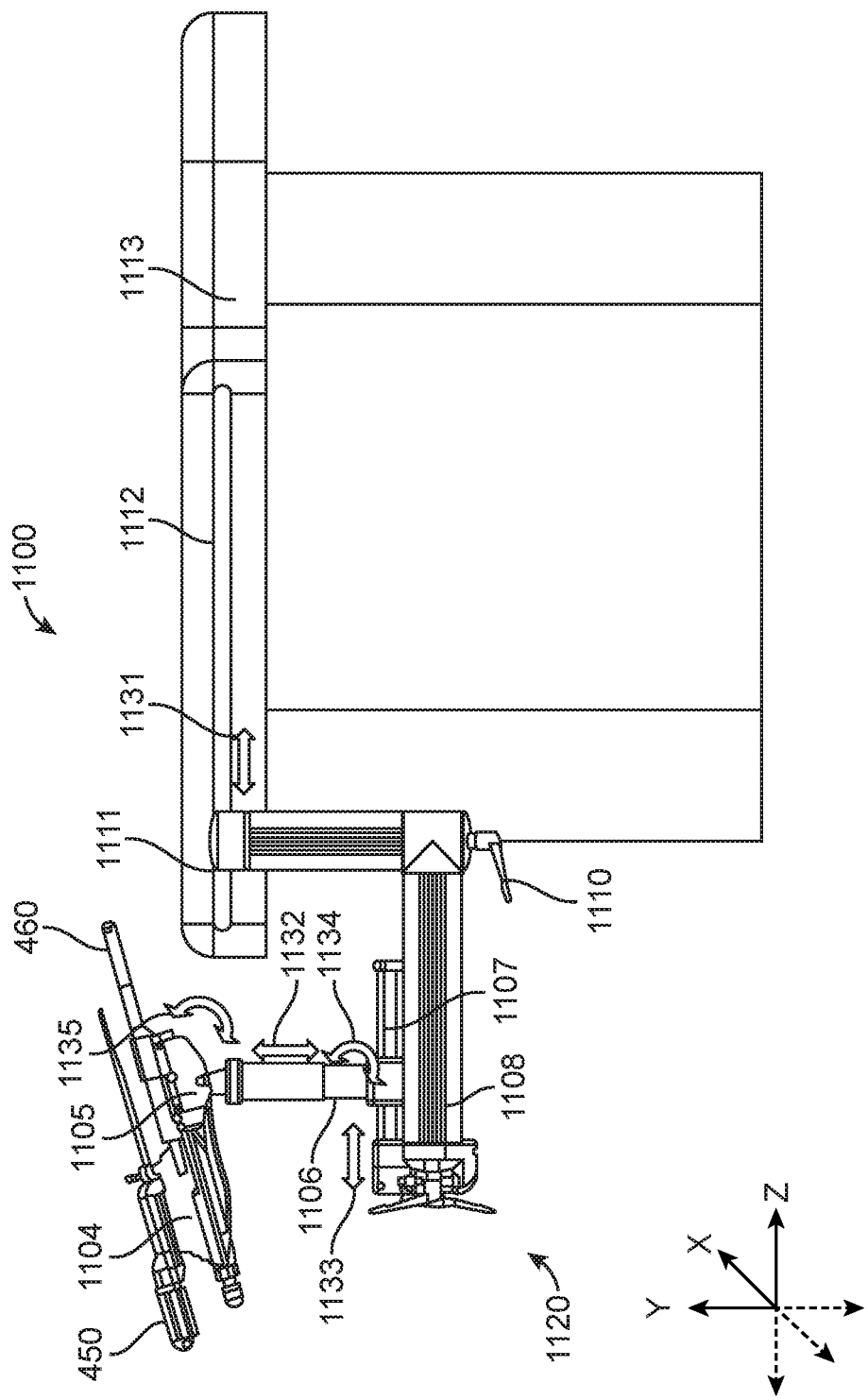
FIGS. 11A, 11B, and 11C show side, front, and perspective views, respectively, of a system for performing tissue resection in a patient, in accordance with some embodiments, the system comprising a treatment table coupled to a system of sliders and mounts for positioning imaging and treatment probes.
Figure 11B:
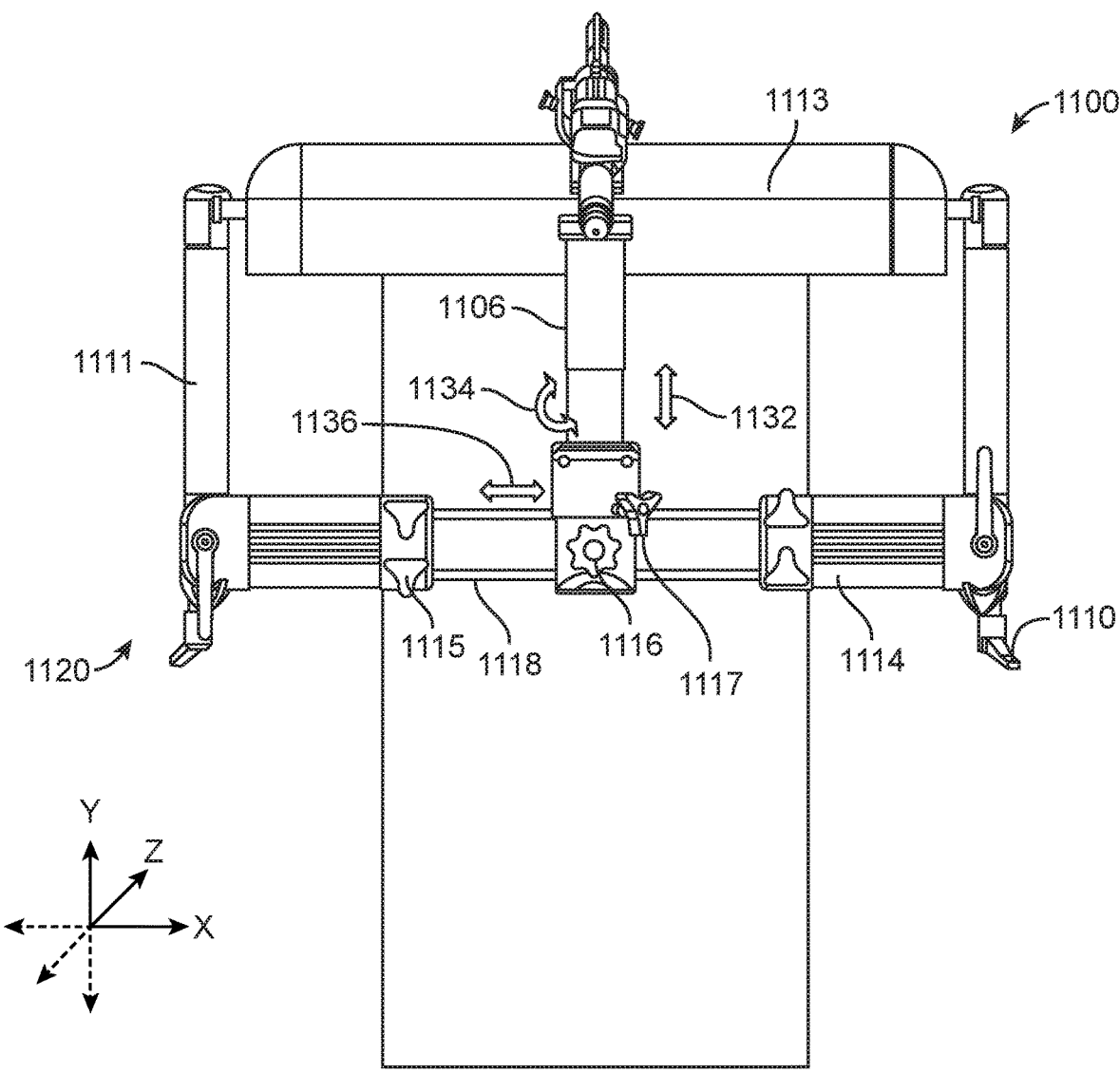
Figure 11C:
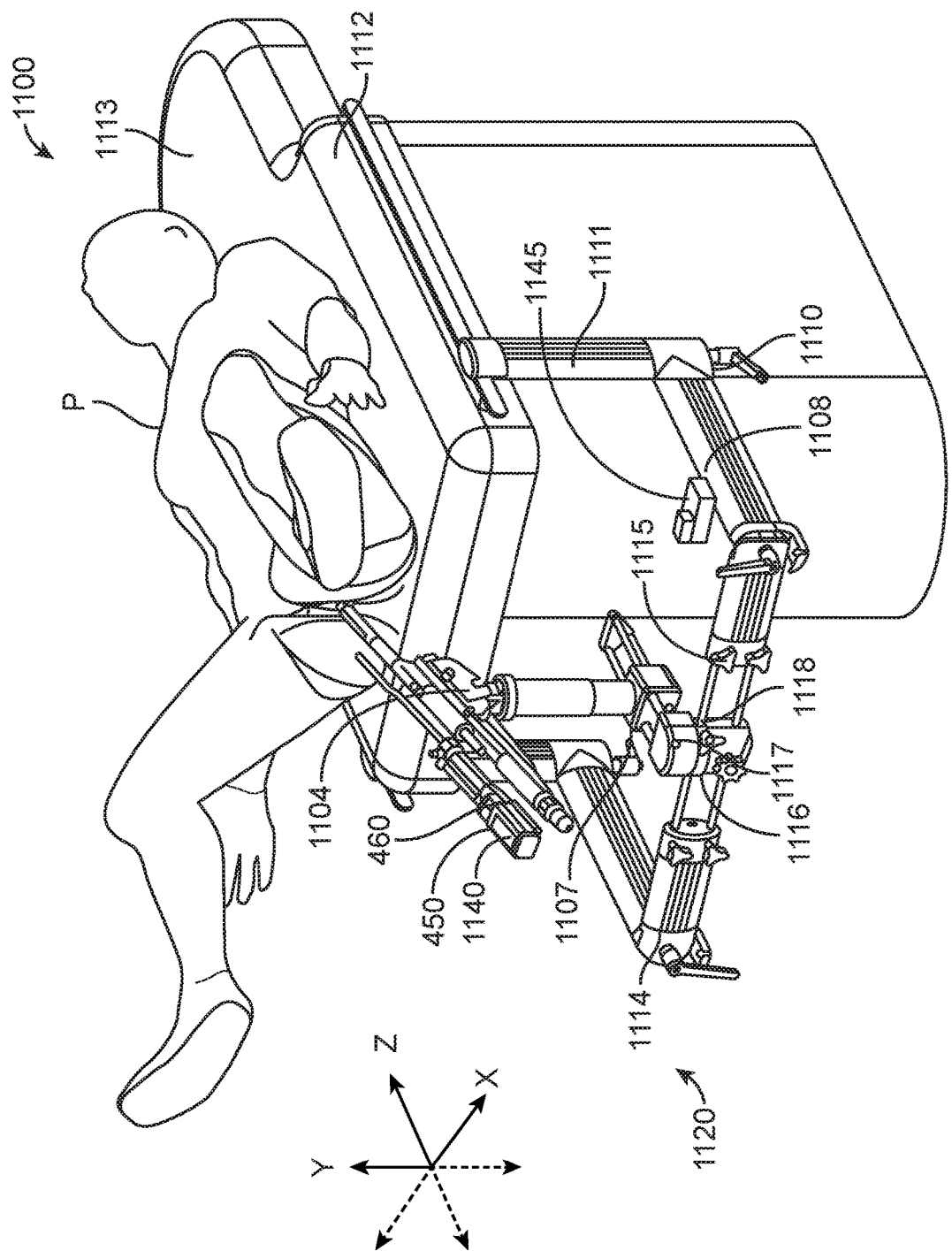

FIGS. 11A, 11B, and 11C illustrate an exemplary embodiment of a treatment system 1100 comprising a treatment table. The system 1100 may comprise one or more components of system 400, and may comprise coupling structures on the probe mount and pivot to couple the arm to one or more of the imaging probe 460 and the treatment probe 450 to the patient after one or more of the probes has been inserted into the patient. FIG. 11A is a side view, FIG. 11B is a front view of the treatment system 1100, and FIG. 11C is a perspective view of the treatment system which shows the positioning of the patient P. FIGS. 11A-11C also show a three-dimensional coordinate system legend comprising an X-axis, a Y-axis, and a Z-axis, wherein each of the X-axis, a Y-axis and the Z-axis are perpendicular to each other, the X and Z axes are orthogonal horizontal axes, and the Y axis is a vertical axis, to aid in the viewing and description of the system 1100. The treatment system 1100 may comprise a treatment probe 450, an imaging probe 460, a platform 1113, and a probe mounting and adjustment assembly 1120. The probe mounting and adjustment assembly 1120 may comprise a probe mount 1104, a pivot 1105, a vertical turret 1106, a first horizontal slider 1107 for translating the vertical turret 1106 along a first Z-translational direction 1133 (i.e., along the Z-axis or an axis parallel thereto), a pair of first horizontal arms 1108 oriented along the Z-direction, a pair of vertical arms 1111 oriented along the Y-direction (i.e., along the Y-axis or an axis parallel thereto), a pair of first locking mechanisms 1110 for the pair of the vertical arms 1111, a pair of second horizontal sliders 1112 for translating the pair of vertical arms 1111 along a second Z-translational direction 1131 (i.e., along the Z-axis or an axis parallel thereto), a patient support such as a platform 1113 having the pair of second horizontal sliders 1112 coupled thereto, a pair of second horizontal arms 1114 oriented along the X-direction with each second horizontal arm 1114 coupled to a respective first horizontal arm 1108, a pair of second locking mechanisms 1115 for the pair of first horizontal arms 1108, a horizontal adjuster 1116 for the vertical turret 1106, a third locking mechanism 1117 for the vertical turret 1106, and a third horizontal slider 1118 for translating the first horizontal slider 1107 in a first X-translational direction 1136 (i.e., along the X-axis or an axis parallel thereto). These arms, sliders, and locking mechanisms may be one or more of robotically or manually actuated or repositioned relative to one another. The treatment probe 450 and the imaging probe 460 may be aligned to be one or more of parallel or co-planar with one another as described herein. One or more of the treatment probe 450, the imaging probe 460, the various arms, the various sliders, or the various mechanisms may be covered with one or more protective drapes to one or more of facilitate providing a sterile operating environment or minimize subsequent clean-up for the various components of the system 1100.

The treatment probe 450 and the imaging probe 460 may be substantially vertically aligned and stiffly (e.g. rigidly) and adjustably connected to one or more probe coupling mounts 1104, wherein a probe coupling mount 1104 can rotate about an axis defined by the pivot 1105, in a first rotational direction 1135 (i.e., about the X-axis or an axis parallel thereto), with respect to the vertical turret 1106 such as in the YZ-plane (or a plane parallel thereto) as shown in FIGS. 11A-11C. In some embodiments, the position of the elongate axis 451 of the treatment probe 450 relative to the elongate axis 461 of the imaging probe 460 may be set by adjusting the position of the treatment probe 450 relative to the probe mount 1104, and by adjusting the position of the imaging probe 460 relative to the probe mount 1104. In some embodiments, the treatment probe 450 and the imaging probe 460 are each detachably mounted to a probe coupling mount 1104 by a fastener comprising a screw, a nut, a washer, a bolt, a pin, a pivot, a hinge, a bearing, a clamp, a strap, a thumb screw, a latch, a collet, a dovetail, a channel, a spring, a magnet, a threading, a key, a slot, a gear, a pulley, a rack, a pinion or any combination thereof. In some embodiments, the treatment probe 450 is detachably mounted to a first probe coupling mount 1104 and the imaging probe 460 is detachably mounted to a second probe coupling mount 1104. In some embodiments, the probe coupling mount 1104 comprises an electrical connector to transmit power and/or data to or from the treatment probe 450 and/or the imaging probe 460 to a computer or processor. In some embodiments, the probe coupling mount 1104 comprises a hose connector to transmit a liquid and/or a gas to the treatment probe 450. In some embodiments, the fastener, the electrical connector, and the hose connector comprise a singular component. In some embodiments, the fastener and the electrical connector comprise a plurality of components. In some embodiments, the position of the treatment probe 450 relative to the probe coupling mount 1104 and the position of the imaging probe 460 relative to the probe coupling mount 1104 are adjusted manually or by a driven actuator, or both. In some embodiments, the position of the treatment probe 450 relative to the probe mount 1104 and the position of the imaging probe 460 relative to the probe mount 1104 are adjusted by a thumb screw, a pivot, a hinge, a pin, a slot, a bearing, a pulley, a rack, a pinion, a linear actuator, a motor, a solenoid, or any combination thereof.

In some embodiments, the probe coupling mount 1104 further comprises a manual actuation feature which allows a user to manually manipulate its position. In some embodiments, the manual actuation feature comprises a handle, a knob, a hilt, a bar, a grip, or any combination thereof.

In some embodiments, the probe coupling mount 1104 can rotate about a first rotational direction 1135 by at least about 315 degrees, by at least about 300 degrees, by at least about 280 degrees, by at least about 260 degrees, by at least about 240 degrees, by at least about 220 degrees, by at least about 200 degrees, by at least about 180 degrees, by at least about 160 degrees, by at least about 140 degrees, by at least about 120 degrees, by at least about 100 degrees, or by at least about 80 degrees.

In some embodiments, the probe coupling mount 1104 further comprises a cable guide, a cable relief member, a slip ring, or any combination thereof to constrain and protect any cables exiting form the treatment probe 450 or the imaging probe 460.

In some embodiments, the substantially vertical turret 1106 additionally extends and retracts in a first Y-translational direction 1132 (i.e., along the Y-axis or an axis parallel thereto) to set the height of the probe mount 1104 relative to the first horizontal slider 1107. The turret may comprise an extension joint to allow extension and retraction, such as telescopic sliding tubes, or a threaded assembly and combinations thereof. In some embodiments, the position of the vertical turret 1106 is adjusted manually or by a driven actuator, or both. The rotation of the probe mount 1104 relative to the vertical turret 1106 may be robotically controlled or manually set. In some embodiments, the rotation of the vertical turret 1106 about its vertical axis of symmetry in a second rotational direction 1134 (i.e., about the Y-axis or an axis parallel thereto) can be set and locked by the third locking mechanism 1117. In some embodiments, the pair of first horizontal sliders 1107 is capable of translating the treatment probe 450 and the imaging probe 460 towards or away from the patient P. In some embodiments, the first horizontal sliders 1107 comprise a manual actuator, a driven actuator or both. In some embodiments, the position of the vertical turret 1106 towards or away from the patient is modified by the horizontal slider 1107. A horizontal adjuster 1116 can translate the robotic arms in the X direction transverse to the patient support. The horizontal adjuster 1116 can be operated by a manual actuator, a driven actuator, or both.

In some embodiments, the third horizontal sliders 1118 allows for translation of the first horizontal slider 1107, and thus the treatment probe 450 and the imaging probe 460, in a horizontal direction (i.e., along the X-axis) towards the left or right side of the patient, wherein one or more third locking mechanisms 1117 may engage and disengage the ability of the vertical turret 1106 to translate horizontally along the third horizontal slider 1118. In some embodiments, each end of the third horizontal slider 1118 is attached to a second horizontal arm 1114, wherein each second horizontal arm 1114 may be perpendicularly attached to a first horizontal arm 1108, and wherein each first horizontal arm 1108 may be perpendicularly attached to a vertical arm 1111. In some embodiments, each vertical arm 1111 is attached to a second horizontal slider 1112 on a platform 1113, wherein the second horizontal slider 1112 is capable of translating the one or more vertical arms 1111, in a horizontal direction (i.e., along the Z-axis) towards or away from the patient, wherein one or more first locking mechanisms 1110, sets the position of the one or more vertical arms 1111 relative to the platform 1113.

In some embodiments, one or more of the exemplary embodiment of a treatment system's 1100 components are comprised of metal, plastic, fabric, cloth, foam, wood, carbon fiber, fiberglass, glass or any combination thereof.

In some embodiments, the vertical turret 1106, the first horizontal slider 1107, the second horizontal slider 1112, and the third horizontal slider 1118 comprise an actuator, a bearing, a shaft, a worm drive, a rack, a pinion, a gear, a belt, a chain, a pulley, a slide, a collar, a shaft, or any combination thereof. In some embodiments, at least one of the vertical turret 1106, the first horizontal slider 1107, the second horizontal slider 1112, and the third horizontal slider 1118 further comprises an encoder, wherein the encoder measures a translational or rotational displacement.

In some embodiments the first locking mechanism 1110, the second locking mechanism 1115, and the third locking mechanism 1117 comprise a cam, a screw, a handle, a knob, a shaft, a clamp, or any combination thereof.

In some embodiments, the sliders, turret and vertical extension joint each comprise an actuator coupled to a processor to control the position and angles of the coupling structure. In some embodiments, the coupling between the horizontal arms 1108 and the second horizontal arm 1114 comprises a powered joint. In some cases, the powered joint is under robotic control of the processor and can be actuated, such as to move the hardware out of the way to assist in patient extraction from the patient support.

In some embodiments, the system comprises a linkage coupled to the processor, and the linkage comprises one or more of the sliders, the turret and the vertical extension joint. Each of these one or more components may comprise an actuator coupled to the processor to control the position and angles of the coupling structure on the arm in response to control signals from the processor.

The arm may comprise a plurality of arms and sliders, for example.

In some embodiments the one or more of the exemplary embodiments of a treatment system 1100 components can be disassembled, portable or both. In some embodiments the treatment system 1100 further comprises, a cable management member, a wheel, a step stool, a power source, a mounting member, or any combination thereof.

One or more imaging sensors 1145 may be provided in one or more locations about the treatment system 1100, and may be provided on the first and/or second horizontal arms. The one more ore imaging sensors may be used to acquire image of the fiducial markers on the imaging probe 460 or the treatment probe 450 or both to aid in alignment and/or docking of the robotic arms with the probes or for detecting position, orientation, or alignment of the probes. A user interface 1140 may be provided on the robotic arms, the probes, or both, to indicate the docked status of the robotic arms with the probes. In some instances, the user interface is one or more visual indicators, such as LED indicators. The one or more visual indicators may convey additional operational or status information of the robotic arms or the probes.

Figure 12:
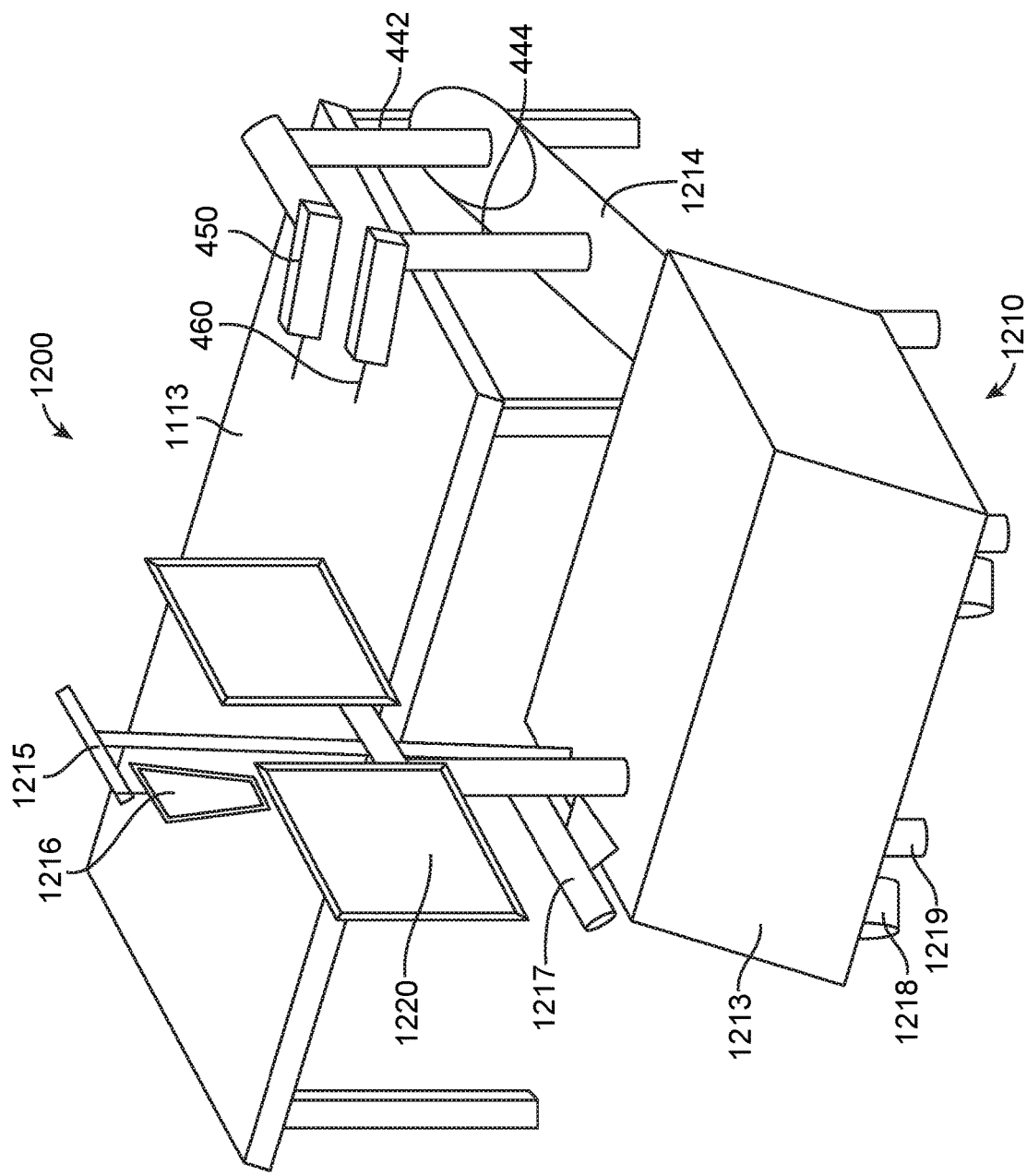
FIG. 12 illustrates a perspective view of a treatment system for performing tissue resection in a patient, in accordance with some embodiments, the system comprising a mobile cart with displays and a common robotic arm base for the robotic arms to actuate the imaging and treatment probes.

FIG. 12 illustrates an exemplary embodiment of a treatment system 1200 comprising a treatment platform. The system 1200 may comprise one or mom components of system 400 or system 1100 as described herein. FIG. 12 is a perspective view of the treatment system 1200. The treatment system 1200 may comprise a treatment cart 1210. The cart 1210 may comprise a housing 1213, a common robotic arm 1214 which may one or more of rotate or translate relative to the housing 1213, a fluid container hanger 1215, a fluid container 1216 such as for saline, a push handle 1217, one or more wheels 1218, a support 1219, one or more display screens 1220, a treatment probe robotic arm 442 which may one or more of rotate or translate relative to the common robotic arm 1214, the treatment probe 450 coupled to the treatment probe robotic arm 442, an imaging probe robotic arm 444 which may one or more of rotate or translate relative to the common robotic arm 1214, and the imaging probe 460 coupled to the imaging probe arm 444.

In some embodiments, the treatment probe robotic arm 442 and the imaging probe robotic arm 444, in coordination with the common robotic arm 1214, position the treatment probe 450 and the imaging probe 460, respectively, in alignment with one another (i.e., parallel and/or co-planar alignment). In some embodiments, the housing 1213 contains a power source, a pressure source, a communication member, a power cable, a medicine, or any combination thereof. In some embodiments, the common robotic arm 1214 can pivot or translate about one or more degrees of freedom with respect to the housing 1213. In one example, the common robotic arm 1214 can pivot about a vertical axis perpendicular to the floor about an angle of about 220 degrees. In some embodiments, the common robotic arm 1214 is capable of extending and contracting. In some embodiments, the cart 1210 is transportable, wherein the cart 1210 may comprise the push handle 1217, and one or more wheels 1218, as well as the support 1219 to maintain stability of the cart 1210 during patient treatment. In some embodiments, the cart 1210 further comprises a fluid container hanger 1215 capable of supporting a saline or fluid container 1216 which stores a quantity of fluid or saline for use with the treatment probe 450 which may provide a pressurized fluid jet for tissue resection. In some embodiments, the cart 1210 further comprises one or mom screens 1220 which are capable of displaying information from the imaging probe 1202 or other sources to a medical practitioner or patient. In some embodiments, the treatment system 1200 further comprises a container for storing removed tissue and expended saline fluid.

Figure 13:
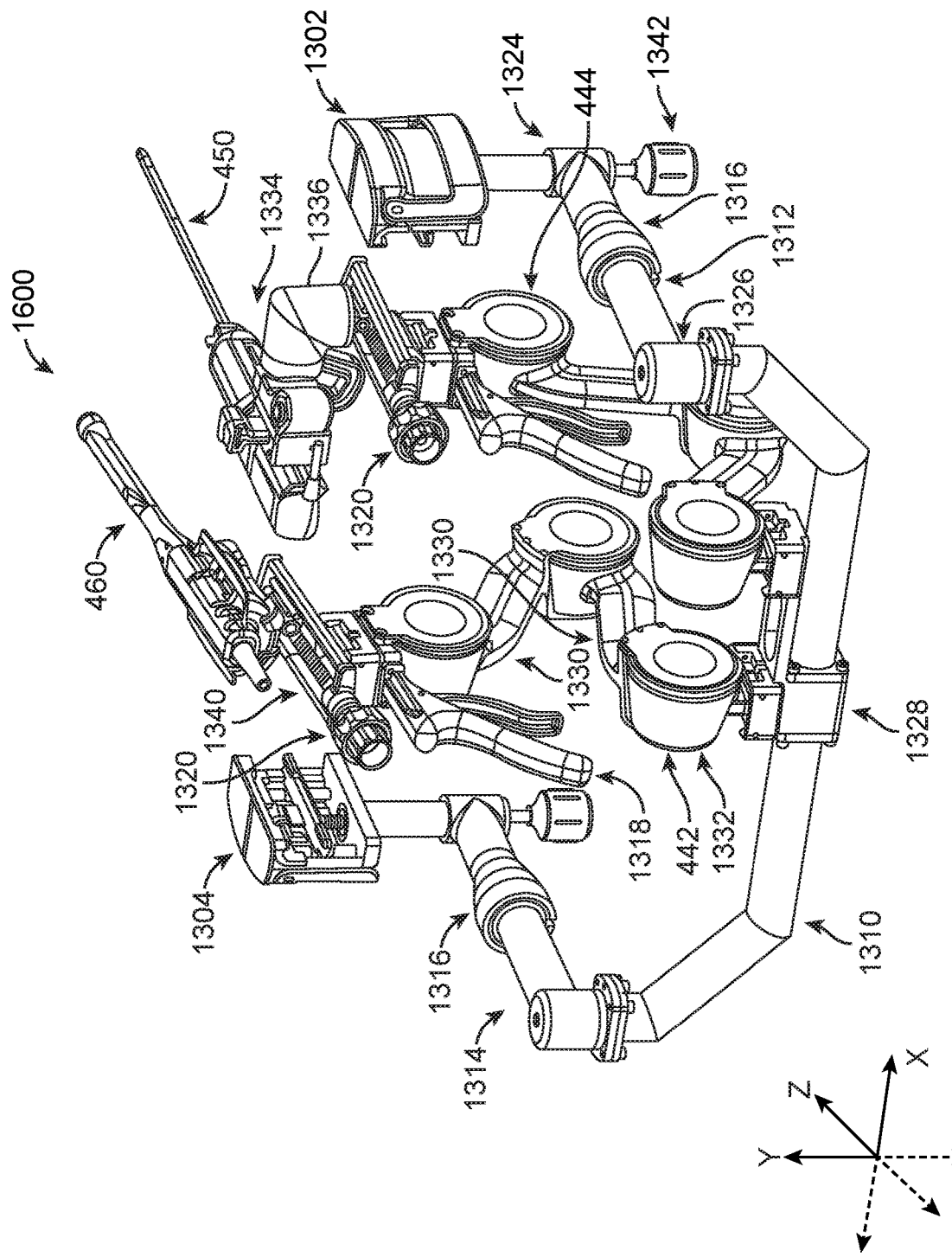
FIG. 13 illustrates a perspective view of a treatment system for performing tissue resection, in accordance with some embodiments.

FIG. 13 illustrates an exemplary embodiment of a probe mounting and adjustment assembly 1600. The probe mounting and adjustment assembly 1600 attaches to a patient support by a plurality of clamps 1302. According to some embodiments, the patient support is a bed, table, or platform, and the clamps attach to the patient support, such as by mechanical clamping onto rails of the patient support. The probe mounting and adjustment assembly 1600 may include 2, 3, 4, 6, or more clamps 1302 for attaching to a patient support. In some embodiments, the mounting assembly 1600 supports the first robotic arm 442 with a first probe 460 mounted thereon and the second robotic arm 444 with a second probe 450 mounted thereon in a substantially "bump proof" configuration, such that a medical professional bumping into one or more of the mounting assembly 1600, the first robotic arm 442, the first probe 460, the second robotic arm 444, or the second probe 450 results in a clinically acceptable amount of movement to the probes inserted into patient, for example movement of no more than about 5 mm.

While the mounting assembly 1600 can be configured in many ways, in some embodiments the mounting assembly is configured to limit movement of the elongate support 1310 relative to the first rail and the second rail to no more than 5 mm in response to a 150 kg load to the elongate support 1310, e.g. to the crossbar 1310. As used herein, the terms elongate support and crossbar are used interchangeably. In some embodiments, the movement is no more than 3 mm in response to a 100 kg load to the elongate support 1310. In some embodiments, the elongate support 1310, the first clamp 1302, the first arm 442, the second clamp 1304 and second arm 444 may be configured in order to limit movement of the elongate support 1310 to no more than 5 mm in response to a 150 kg load to the elongate support 1310, and the movement may be no more than 3 mm in response to a 100 kg load to the elongate support 1310. In some embodiments, the probe to be inserted into the patient comprises a distance within a range from about 20 cm to about 60 cm, and the mounting assembly 1600 is configured to move a distal end of the probe no more than 6 mm in response to the load to the elongate support 1310.

The probe mounting and adjustment assembly 1600 can be a modular system that consists of a collapsible universal operating table mounting system and a pair of lockable positioning arms that install onto the universal mount. The universal mount is easy and intuitive to adjust and fits the majority of commonly used operating tables, including different size mounting rails, varying table widths, and tables with removable and fold-down leg supports. It provides a rigid platform that enables the mounting arms 1312, 1314 to be optimized for weight, stiffness, fluid movement, and range-of-motion to provide superior surgical planning capabilities.

The two mechanical arms 442, 444 allow smooth, fluid motion within a defined surgical planning field. They provide tactile feedback of patient anatomy to minimize risk of injury, while aiding with probe alignment to streamline the surgical planning process. When locked, the mechanical arms 442, 444 provide a rigid interface that holds both imaging and treatment probes where the operator wants them positioned. During procedure setup and takedown, the probe mounting and adjustment assembly 1600 can be split into compact, easily manageable components that can be deployed by one person and mounted in/on the console for storage.

According to some embodiments, the probe mounting and adjustment assembly 1600 comprises two similar, e.g. substantially identical rail clamps 1302, 1304, and a crossbar 1310. The rail clamps 1302, 1304 can be adjusted and set to fit all commonly used table rail sizes and install/remove with a simple throw of a lever 1406. The lever 1406 is the primary touch point of the rail clamps and allows them to be installed with one hand in a single motion. The crossbar 1310 docks into the two receptacles 1316 of the rail clamps 1302, 1304 to complete the table mounting system, and folds flat for storage. It is deployed by squeezing two control triggers, one in each hand. The control triggers unlock the corner pivots that enable folding for storage as well as fine width adjustment for mounting to the patient support. The control triggers also unlock the mechanism that secures the crossbar 1310 to the rail clamps. According to some embodiments, the mechanisms on the crossbar 1310 are auto-engaging when pushed into position and self-locking to minimize the possibility of improper assembly. The crossbar 1310 might also have a width adjustment mechanism for coarse adjustment to different operating table widths. The components can be positioned in a symmetrical form to create an isosceles trapezoid geometry relative to the OR table. In some embodiments, the rail clamps 1302, 1304 may be placed in differing Z positions, the patient may be placed in differing X positions and angled on the table at a Z' angle creating multiple non-symmetries. The design of the mounting assembly 1600 including rail clamps 1302, 1304, rail clamp receptacles 1316, and lockable crossbar mounting arms 1312, 1314, and crossbar 1310 (with included arm rotation about Y axis) provide for adjustment of the arm structure allowing precise location of the imaging probe 460 and the treatment probe 450 which accommodate all variables of equipment set-up, patient anatomy, and patient position.

According to some embodiments, the mechanical arms 442, 444 comprise two similar arms (e.g. substantially identical arms) and a lateral adjustment mechanism. Each arm may comprise three rotating/lockable joints linked together by arm segments, an interface on the bottom to securely mount to the crossbar 1310, and a control handle 1318 and stepper mount 1320 at the top. The joints may be configured to rotate about the X axis. The control handle 1318 is the main touchpoint for manipulation and enables one-handed positioning and adjustment of each probe 450, 460. The stepper mount 1320 provides a drape-safe interface for mounting the steppers used for fine control of the imaging probe 460 and treatment probe 450. Each mechanical arm 442, 444 may be draped with surgical draping to minimize contamination and simplify cleaning after the procedure. The control handle 1318 may have a two-stage actuation mechanism, the first for unlocking all the joints in unison and keeping them unlocked, and the second for re-locking the system when in the desired position. This may reduce the need to hold each arm with a tight grip during manipulation for improved tactile feel and more precise control. In some embodiments, the control handle 1318 comprises a handle for manipulating the robotic arms, and a button or switch engages or disengages locking mechanisms within the joints to allow or disallow manual manipulation of the robotic arms.

The clamps 1302, 1304 are connected to a receptable 1316 by a clamp coupling 1324. The clamp coupling 1324 may allow a degree of freedom between the clamp 1302 and the receptacle 1316, thereby allowing adjustment of the orientation or position of the clamp 1302 to facilitate clamping to the patient support. The receptacle 1316 is connected to a mounting arm 1312. In some embodiments, the receptacle 1316 defines a recess and the mounting arm 1312 couples with the receptacle 1316 by fitting inside the recess and may be secured through any suitable mechanical interaction, such as a ball detent, friction fit, set screw, thumb screw, a keyway, a boss and pocket, a pin, an interference structure, or some other suitable connection structure. In some embodiments, the mounting arm 1312 comprises a lever that pivots a locking pin to allow a secure connection between the mounting arm 1312 and the receptacle 1316. In an exemplary use, according to some embodiments, the mounting arm 1312 may be inserted into the recess of the receptacle 1316 and a locking pin may retract as the mounting arm 1312 engages the inside surface of the receptacle 1316. Upon full insertion, a locking pin or other protruding structure which may be biased to extend away from the mounting arm 1312, may snap outwardly from the mounting arm into a recess, cavity, hole, or pocket formed in the receptacle 1316 to securely connect the mounting arm 1312 to the receptacle 1316. A lever on the mounting arm 1312 may be coupled to the protruding structure such that when the lever is depressed, the protruding structure is withdrawn into the mounting arm 1312 to facilitate the mounting arm 1312 being withdrawn from the receptacle 1316.

The mounting arm 1312 is connected to a crossbar 1310, such as by a crossbar coupling 1326. The crossbar coupling 1326 may allow pivotal movement between the mounting arm 1312 and the crossbar 1310. As illustrated, a pair of mounting arms 1312, 1314 may be connected to the crossbar 1310 at either end of the crossbar 1310. The pair of mounting arms 1312, 1314 may be rotated or pivoted about the crossbar coupling 1326 to vary the distance between the clamps 1302, 1304. In this way, the distance between the clamps 1302, 1304 can be adjusted to fit on a variety of differently sized patient supports.

The crossbar 1310 carries a mechanical arm base 1328. The mechanical arm base 1328 may be slidably connected to the crossbar 1310 which allows the mechanical arm base 1328 to slide along the X axis and move horizontally left and right relative to a patient. The mechanical arm base 1328 may be secured to the crossbar 1310 in any suitable way, such as by a screw, thumb screw, cam, lever, lock, twist lock, or any suitable structure for securing the mechanical arm base 1328 to the crossbar 1310.

The mechanical arm base 1328 provides an attachment point for one, two, or more mechanical arms 442, 444. As shown, in some embodiments, two mechanical arms are connected to the mechanical arm base 1328. The mechanical arms 442, 444 may be connected by any type of secure connection, such as screws, sliding lock, clips, or other suitable connector. The components of the probe mounting and adjustment assembly 1600 can be formed of any suitable material, and in some embodiments, one or more components are formed of metal, such as stainless steel, titanium, tantalum, platinum, palladium, or any suitable alloy. The components of the probe mounting and adjustment assembly 1600 can alternatively or additionally be formed of any suitable polymers, such as one or more of polyvinyl chloride (PVC), polypropylene (PP), polyethylene (PE), polystyrene (PS) as well as nylon, polyethylene terephthalate (PET), polyimide (PA), polycarbonate (PC), acrylonitrile butadiene (ABS), polyetheretherketone (PEEK) or polyurethane (PU), for example.

In some embodiments, the clamp 1302, clamp coupling 1324, receptacle 1316, mounting arm 1312, crossbar coupling 1326, crossbar 1310, mechanical arm base 1328, or mechanical arm 444 comprise an actuator, a bearing, a shaft, a worm drive, a rack, a pinion, a gear, a belt, a chain, a pulley, a slide, a collar, a shaft, or any combination thereof. In some embodiments, at least one of the clamp 1302, clamp coupling 1324, receptacle 1316, mounting arm 1312, crossbar coupling 1326, crossbar 1310, mechanical arm base 1328, or mechanical arm 444 comprise an encoder, wherein the encoder measures a translational or rotational displacement or position.

The mechanical arms 442, 442 may be provided with one or more segments separated by joints that provide degrees of freedom between the segments. For example, a mechanical arm may have two, three, four or more segments 1330 that are each coupled to one another by joints 1332 that allow relative pivotal or rotational movement between adjacent segments 1330. The mechanical arm itself may be coupled to the mechanical arm base 1328 by a joint that allows rotation of the mechanical arm about one or more axes.

The mechanical arm 442 carries a probe mount 1334 to which a probe 450 may be mounted. As illustrated, a first mechanical arm 442 carries an imaging probe 460 and a second mechanical arm 444 carries a treatment probe 450. In some embodiments the probe mount 1334 comprises a riser 1336 configured to elevate the probe, such as a treatment probe 450, in the Y direction so that the treatment probe 450 is higher than the imaging probe 460. Thus, in the case where the treatment probe 450 and the imaging probe 460 are brought into a vertical alignment with one another, the riser 1336 facilitates the treatment probe 450 avoiding contact with the imaging probe 460 as they are vertically spaced from one another.

The treatment probe 450 has an elongate axis along the shaft of the treatment probe 450, and similarly, the imaging probe 460 has an elongate axis along the shaft of the imaging probe 460. In some configurations, the treatment probe axis and the imaging probe axis are aligned in a plane. That is, the axes are parallel to one another thus making them co-planar. In some embodiments, the configuration of the mechanical arms 442, 444 and the probe mounts 1334 can position the treatment probe axis and the imaging probe axis co-planar with one another in a vertical plane. Put another way, the two axes can be aligned vertically with one probe directly above the other probe.

According to some embodiments, the probes are moveable within a surgical planning field in the X, Y, and Z directions as well as rotational motion about any of these axes. In some cases, the imaging probe 460 and the treatment probe 450 are independently positionable in the YZ plane, and in some cases, there is limited relative movement along the X axis. According to some embodiments, the imaging probe 460 has a limited range of translational motion, and in some cases, is about ±2 inches from the center position in the X direction; −3 inches to +4 inches in the Y direction; −9" to +2 inches in the Z direction (and an additional 100 mm in the Z direction with fine control of the stepper motor). The imaging probe 460 may have a limited range of rotational motion, and in some embodiments, can be rotated anywhere between 0° and about 45° about the X axis, ±15° about the Y axis, and ±32° about the Z axis.

According to some embodiments, the treatment probe 450 may have a limited range of motion, which may be on the order of about ±2 inches from center along the X axis, 3 inches to 12 inches from the top of the patient support, −9 inches to 2 inches in the Z direction (plus an additional about 100 mm under stepper motor control). In some embodiments, the treatment probe 450 may be rotated, such as about ±30° about the X axis, ±15° about the Y axis, and only very minor adjustment about the Z axis.

The mechanical arms may also comprise a control handle 1318. According to some embodiments, a control handle 1318 is coupled to one or more of the mechanical arms and allows an operator to manually position the mechanical arms 442, 444 and concomitantly, the probes carried by the mechanical arms. The control handle 1318 may be any suitable configuration that provides a way of manually adjusting or moving the mechanical arm. In some embodiments, the control handle 1318 comprises a lever that disengages a clutch in one or more of the joints separating the segments of the mechanical arm. In some instances, the lever of the control handle 1318, when depressed, disengages one, two, three, or more joints to allow the joints to pivot, rotate, or some combination that allows an operator to manually position the mechanical arms. The control handles 1318 may be connected to, or may be formed integrally with, a probe slider 1340. The probe slider 1340 allows the imaging probe 460 or the treatment probe 450, or both, to translate substantially in the Z direction into and out of a patient. The probe slider 1340 may be manually operated, robotically operated, or a combination of both.

In use, clamps 1302, 1304 are coupled to a patient support. There may be two clamps, four clamps, six clamps, or more that are coupled to the patient support, which in some instances, is a bed. The clamps may include a clamp adjuster 1342 that allows spacing of the jaws within the clamp. A handle 1408 on each clamp is manipulated by an operator and the jaws of the clamp securely grasp the patient support. The receptacle 1316 may be manipulated to position the receptacle 1316 in an orientation configured to couple with the mounting arm 1312 of the probe mounting and adjustment assembly 1600. The mounting arms 1312, 1314 are then coupled to the receptacles 1316 and secured to the mounting arms in any suitable manner.

The crossbar 1310 may be connected to the mounting arm 1312; however, in some embodiments, the crossbar 1310 and mounting arms 1312, 1314 are not removeable from one another and coupling of the mounting arms to the receptacles 1316 places the crossbar 1310 in an appropriate position for treatment of the patient. Once the crossbar 1310 is in place, the mechanical arms 442, 444 may be secured to the mechanical arm base 1328 of the crossbar 1310. The imaging probe 460, the treatment probe 450, or both are then coupled to the probe mounts 1334. The operator may then manually manipulate the mechanical arms 442, 444, such as by using the control handles 1318, to position the imaging probe 460 and the treatment probe 450.

The mechanical arms 442, 444 may then be robotically controlled or may be manually controlled during part, or all, of a procedure. In some embodiments, the mechanical arms 442, 444 are put into a starting position. The modular nature of the probe mounting and adjustment assembly 1600 allows the components to be separated, easily managed, and setup individually. The illustrated configuration further allows treatment planning by automatically aligning the imaging probe 460 and the treatment probe 450 in the same plane and enables smooth, tactile positioning and adjustments of the probes. Further, in some embodiments, the mechanical arms enable positioning and compression adjustments to the probes, while steppers motors in the joints allow for computer-controlled Z-direction positioning and angular adjustment of the probes. While in some embodiments, the description references the components of a singular mechanical arm 442, mounting arm 1312, and accompanying hardware, it should be appreciated that additional mechanical arms may have identical or similar hardware.

FIGS. 14A, 14B, and 14C illustrate an exemplary embodiment of a clamp 1302 that can be used with a probe mounting and adjustment assembly 1600. The clamp 1302 has a fixed jaw 1402, a moveable jaw 1404, and a lever 1406 that varies the distance between the fixed jaw 1402 and the moveable jaw 1404. The lever 1406 includes a handle 1408 configured for gripping and manipulating the clamp. The lever 1406 is mechanically coupled to the moveable jaw 1404 and when the handle 1408 is in an upward position relative to the clamp 1302, the jaws are spaced apart and as the lever 1406 is moved downwardly with respect to the clamp 1302, the moveable jaw 1404 is brought in closer proximity to the fixed jaw 1402 from a first position 1410 to a second position 1412. In some instances, both an upper jaw 1402 and a lower jaw 1404 are moveable with respect to each other, but in the illustrated embodiment, the upper jaw 1402 is illustrated as fixed and the lower jaw 1404 is moveable.

The clamp 1302 includes a clamp coupling 1324 the affixes the clamp to the receptacle 1316. In some embodiments, the receptacle 1316 has a recess 1420 that is configured to accept a portion of the mounting arm 1312 therein to facilitate a secure attachment between the receptacle 1316 and the mounting arm 1312. The clamp coupling 1324 provides for rotational motion of the receptacle 1316 relative to the clamp 1302. This allows for the clamp 1302 to be coupled to a patient support in any angle or configuration and allow the receptacle 1316 to aim in a suitable direction to receive the mounting arm 1312. While the illustrated embodiment shows a rotational coupling between the receptacle 1316 and the clamp 1302, other forms of attachment are contemplated, such as for example, a ball and socket joint, a hinge, a pivot, or other structure to allow the receptable to move with respect to the clamp 1302.

A clamp adjuster 1342 is provided to provide for initial adjustment of the clamp 1302. For example, the clamp adjuster 1342 can be used to move the moveable jaw 1404 into the first position 1410. The handle 1408 can then be used to move the moveable jaw 1404 to the second position 1412, in which the patient support is gripped between the fixed jaw 1402 and the moveable jaw 1404. Where the grip on the patient support is not tight enough, the clamp 1302 can be disengaged from the patient support and the clamp adjuster 1342 can be used to reposition the moveable jaw 1404 in the first position 1410. The lever 1406 can then be used to move the moveable jaw 1404 to the second position 1412 to tightly engage the fixed jaw 1402 and the moveable jaw 1404 onto the patient support. As used herein, the first position 1410 of the moveable jaw 1404 is associated with the clamp in a disengaged configuration and the second position 1412 of the moveable jaw 1404 is associated with the clamp in an engaged configuration. The clamp adjuster 1342 can be used to vary the first position 1410, which has the effect of varying the clamping force when the moveable jaw 1404 is moved to the second position 1412.

FIGS. 15A, 15B, 15C, and 15D illustrate the inner working of an exemplary clamp 1302 that is usable with embodiments of the probe mounting and adjustment assembly 1600 described herein. FIGS. 15A and 15B illustrate the clamp in a disengaged configuration and FIGS. 15C and 15D illustrate the clamp in an engaged configuration. The clamp 1302 comprises a lever 1406 with a handle 1408 formed therein. The lever 1406 is pivotally coupled to the fixed jaw 1402 by a lever shaft 1502 and is configured to pivot between an upper, disengaged orientation, and a lower engaged orientation. The lever shaft 1302 is coupled to a lever arm 1504, which is in turn coupled to an adjuster block 1506. The adjuster block 1506 is connected to the adjuster post 1508, such as by forming internal threads in the adjuster block 1506 that cooperate with threads formed on the adjuster post 1508.

In some embodiments, the lever shaft 1502 is pivotally connected to the lever arm 1504 at a lever arm upper coupling 1510 and pivotally connected to the adjuster block 1506 at a lever arm lower coupling 1518 and movement of the lever 1406 about the lever shaft 1502 causes movement of the lever arm upper coupling 1510 about the lever shaft 1502. The lever arm 1504 is pivotally coupled to the adjuster block 1506 and pivotal movement of the lever arm 1504 about the lever shaft 1502 cause translational movement of the adjuster block 1506, and consequently, translational motion of the adjuster post 1508.

The moveable jaw 1404 comprises through holes that capture a pair of jaw posts 1512 allowing slidable movement of the moveable jaw 1404 over the jaw posts 1512. The jaw posts 1512 extend between the clamp base 1514 and the fixed jaw 1402. The adjuster block 1506 includes a jaw mover 1516 protrusion that is configured to contact the moveable jaw 1404 and as the adjuster block 1506 moves upwardly, the jaw mover 1516 contacts the moveable jaw 1404 and moves the moveable jaw 1404 between the first position and the second position. The adjuster post 1508 can be rotated, such as by a thumb screw or knob on the clamp adjuster 1342 to vary the first position of the adjuster block 1506 depending on the size of the patient support to which the clamp is to be attached to. In some embodiments, the clamp 1302 may have indicia corresponding with the first position of the moveable jaw 1404, such that the adjustment of the adjuster post 1508 and adjuster block 1506 can be repeated for subsequent clamps or subsequent procedures. For example, once a first clamp 1302 is dialed in to apply a proper amount of clamping force onto a patient support, the indicia may visually indicate a position or setting of the clamp adjuster 1342 that can be used to adjust a subsequent clamp, such as a second clamp 1304, a third clamp, a fourth clamp, and so on so that all the clamps have a similar clamping force onto the patient support. This clamping method relies on an over-center highly stressed linkage to achieve the high clamping force and anti-release (although a latch locking feature [not shown] could be used to prevent release). In some embodiments, when clamping onto the bedrail, as the lever 1406 is lowered, closing the jaw gap (the distance between the fixed jaw 1402 and the moveable jaw 1404), the jaws contact the rail before the lever 1406 is in its' home position. At this point the linkage and jaws (both fixed and moveable) are subjected to forces which cause them to move within elastic deformation of the materials. This elastic deformation increases the 'feeling' of force on the closing lever 1406 but at a point where the design of the linkage provides significant lever arm mechanical advantage. All the metal becomes stressed as the clamp is closed and the linkage crosses a maximum distance of deformation and moves to a lesser (but still significant) position of deformation. This lesser distance requires a force to move it back over the maximum distance in order to release the clamp 1302. Relevant to the performance of this clamping is consideration of material characteristics of the fixed and movable jaws (linear springs), lever arm 1504 (c or s shaped spring), lever shaft 1502, including spring constant (k), material modulus, and design consideration preventing reaching the elastic yield of the materials which would cause permanent deformation of the components. Additionally, if the above components were a totally rigid system, this could require a spring element designed into the adjuster block 1506.

FIGS. 16A, 16B, 16C, and 16D illustrate side views of a clamp that can be used with the probe mounting and adjustment assembly 1600 according to some embodiments, shown in sequence as the handle 1408 is moved through its range of motion from a disengage position, to halfway, to three-quarter of the way, and to a fully engaged position, respectively. In use, the clamp adjuster 1342 is used to establish the initial first position of the lower jaw 1404, by turning the clamp adjuster 1342 to advance the adjuster block 1506 along a threaded portion of the adjuster post 1508. This allows an initial first position of the moveable jaw 1404 to be established while the lever 1406 remains in a disengaged position.

Figure 16A:
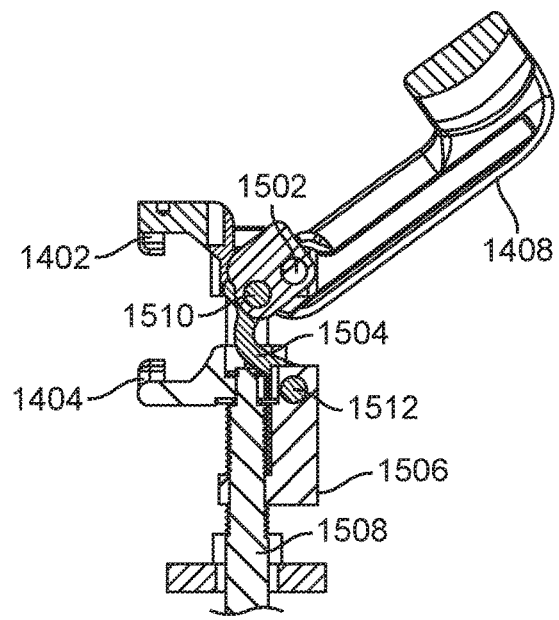
FIGS. 16A, 16B, 16C, and 16D illustrate side internal views of a clamp for use with a treatment system, in accordance with some embodiments.
Figure 16B:
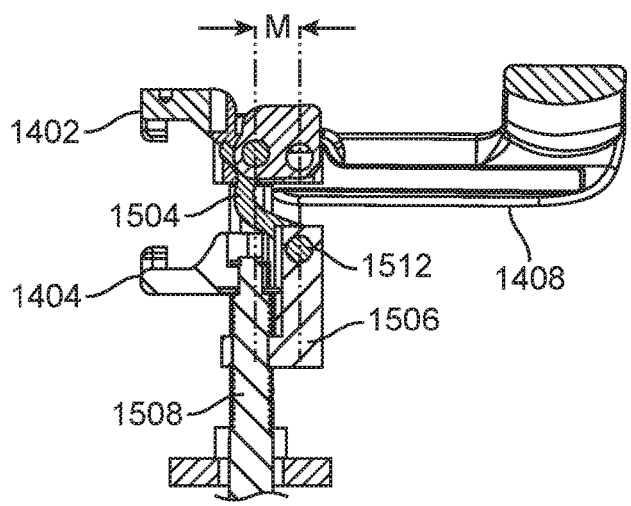
Figure 16C:
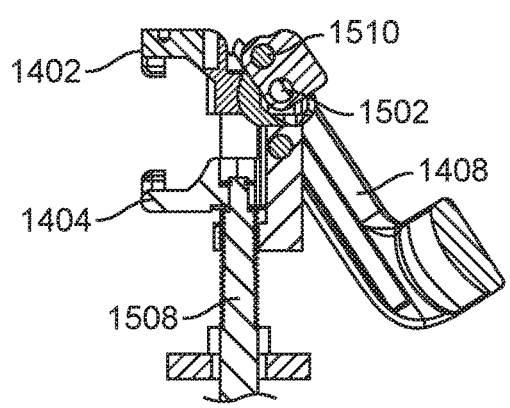
Figure 16D:
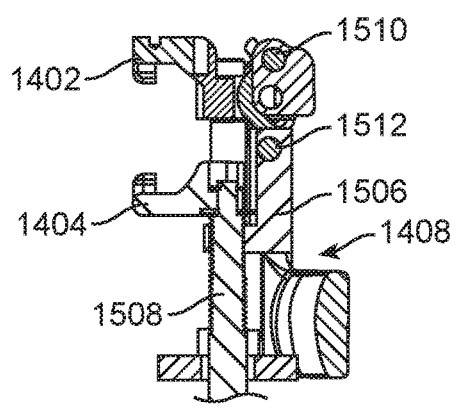

The lever arm upper coupling 1510 is offset from the lever shaft 1502 by a distance M, and the lever arm upper coupling 1510 rotates about the lever shaft 1502. It should be noted that as illustrated in FIG. 16A, the moveable jaw 1404 is free to move downwardly away from the fixed jaw 1402 until it contacts the adjuster block 1506, which limits the movement of the moveable jaw 1404 in a direction away from the fixed jaw 1402. As the lever 1406 is moved from the position shown in in FIG. 16A to the position illustrated in FIG. 16D, the lever arm upper coupling 1510 rotates about the lever shaft 1502 and moves from a position approximately below the lever shaft 1502, to a position approximately directly above the lever shaft 1502. This motion results in a linear translation of the adjuster block 1506 a distance of 2M. Correspondingly, the adjuster block 1506 and the moveable jaw 1404 also move a linear distance equal to 2M. For example, in FIG. 16D the top pin is A (lever arm upper coupling 1510), middle pin is B (lever shaft 1502), bottom pin is C (lever arm lower coupling 1518). B is located in space, and is non-movable relative to the fixed jaw 1402. A rotates about B causing the lever arm 1504 to rotate about C. The movement of the lever arm 1504 causes C to translate in the Y axis (causing the movable jaw movement). It can be imagined that the points B and C remain colinear and along the Y axis (axis called BCY) with A traversing arcs of different radius about B and C. Each of A, B, and C have imaginary parallel X lines Ax, Bx, Cx through them which distance between them changes when the handle 1408 is moved. Further the distance between Ax and Cx is Drotate (many positions), Dmax (A is highest) (this is the maximum force attained), and Dlocked (A crosses BC Y axis) (this is the persistent clamping force). The locking mechanism of this design relies on the locking position of A being reached when during the handle 1408 closing the distance between Ax and Cx reach a maximum distance Dmax and upon further closing of the lever 1406 the distance between Ax and Cx is less than Dmax reaching Dlocked. This position relies on A crossing the axis BCY.

The components of the clamp 1302 can be formed of any suitable material and in some embodiments, the fixed jaw 1402 and the moveable jaw 1404 are formed of a suitable metal, such as any of a variety of steels or steel alloys, aluminum, or other type of metal or metal alloy. The lever 1406 and handle 1408 may be formed of any suitable material and may be a polymeric material and in some cases is a reinforced polymer. The fixed jaw 1402 and moveable jaw 1404 can be any suitable shape, and in some embodiments, one or more of the fixed jaw 1402 and the moveable jaw 1404 are wedge-shaped, U-shaped, L-shaped, or some other suitable cross-sectional shape to clamp onto various patient supports. In some cases, the fixed jaw 1402 and the moveable jaw 1404 are configured to clamp onto a rail shaped as a tube, a flat bar, an ovoid tube, or a rail having some other geometry. In use, the clamps can be affixed to a patient support as a first step in preparation for a procedure. The crossbar 1310 can then be mounted to the clamps by the mounting arms and the receptacle 1316.

Figure 18A:
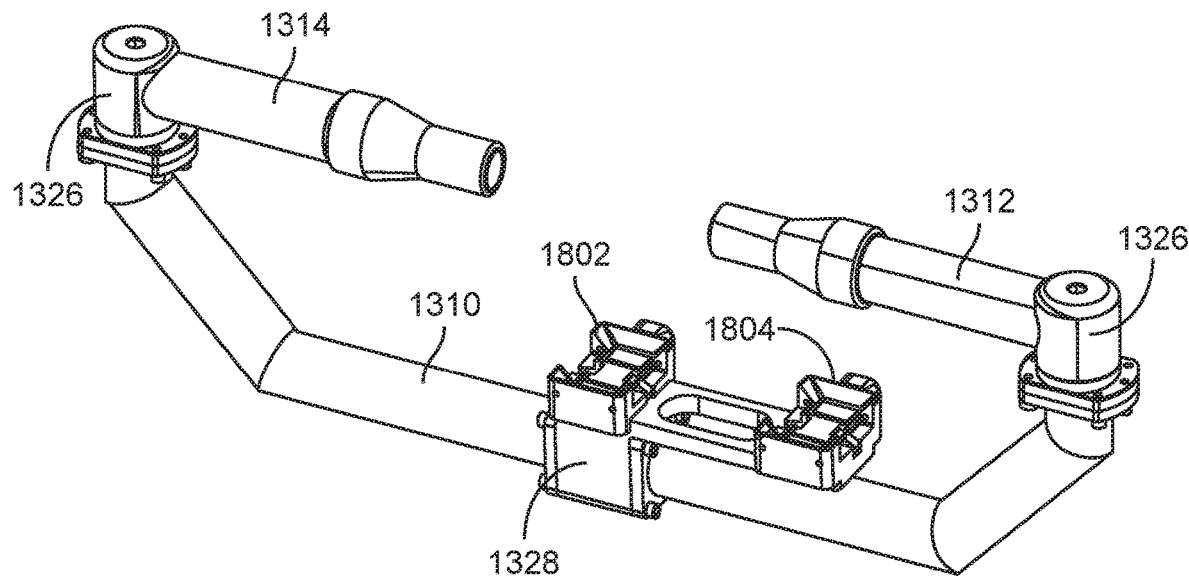
FIGS. 18A and 18B illustrate perspective views of a crossbar with mounts for use with a treatment system, in accordance with some embodiments.
Figure 18B:
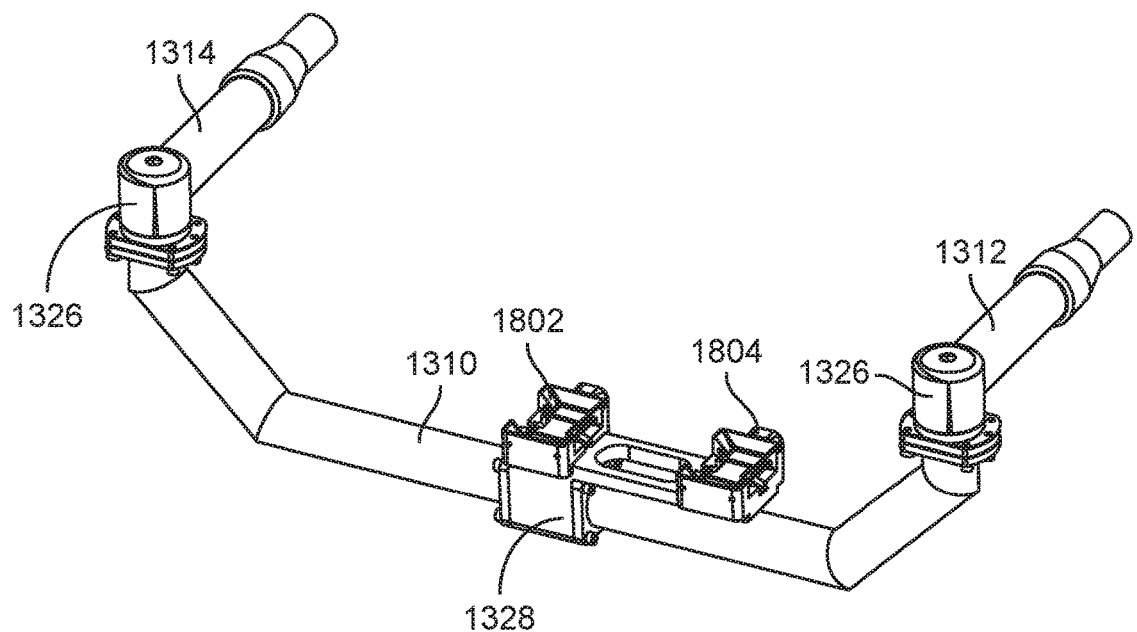

FIGS. 17A, 18B, and 17C illustrate a clamp 1302 affixed to a rail 1702 in rear perspective view, a side view, and a front perspective view, respectively. The illustrated clamp 1302 is substantially as described elsewhere herein, such as with respect to FIGS. 16A-16D. A patient support 1113 comprises a rail 1702 along a side thereof. The rail 1702 may be spaced apart from the patient support 1113 a distance to allow people and objects to grasp the rail 1702 and/or be mounted thereto. The clamp 1302 can be mounted to the rail with a sufficient clamping force to create a secure engagement with the rail 1702 and the patient support 1113. In some embodiments, the clamps 1302 have a low profile and do not extend above the upper surface of the patient support 1113. As used herein, the term "low profile" is used to describe the clamps 1302 that do not extend upwardly above the top surface of the patient support 1113. This facilitates attaching the clamps 1302 to a patient support 1113 before a patient is placed upon the patient support 1113. The low profile clamps do not interfere with a patient being placed onto the patient support.

In some embodiments, a sensor 1399 is coupled to one or more clamps as described herein, such as a clamp configured to couple to a rail. In some embodiments, the sensor 1399 comprises a plurality of sensors coupled to a clamp on each side of the rail. The sensor can be configured to measure loading of one or more of the clamp, the rail, or support coupled to a robotic arm as described herein.

FIGS. 18A and 18B illustrate a perspective view of an exemplary embodiment of a crossbar 1310 with attached mounting arms 1312, 1314 that can be used in conjunction with a probe mounting and adjustment assembly 1600 as described herein. The crossbar 1310 has a first end and a second end, both of which can be connected to a mounting arm 1312. A crossbar coupling 1326 connects the mounting arm 1312 to the crossbar 1310 and provides for pivotal movement of the mounting arm 1312 relative to the crossbar 1310. The crossbar coupling 1326 allows pivotal movement of the mounting arm 1312 during setup of the probe mounting and adjustment assembly 1600 to allow the clamp 1302 to be properly positioned on the patient support 1113 for clamping, and in some embodiments, can be tightened to resist pivotal movement of the mounting arm 1312 relative to the crossbar 1310. The crossbar coupling 1326 can be any suitable coupling that allows adjustability of the mounting arm 1312, and may comprise an actuator, a bearing, a shaft, a worm drive, a rack, a pinion, a gear, a belt, a chain, a pulley, a slide, a collar, a shaft, or any combination thereof. The crossbar coupling 1326 may further include a locking mechanism to selectively fix the relative position of the mounting arm 1312 and the crossbar coupling 1326. In some embodiments the locking mechanism comprises a cam, a screw, a handle, a knob, a shaft, a clamp, or any combination thereof.

A mechanical arm base 1328 may be slidably disposed on the crossbar 1310 and is configured to selectively slide along the length of the crossbar 1310. The mechanical arm base 1328 can be selectively secured to the crossbar 1310 at a desired location by any mounting mechanism, such as a screw, a cam, a handle, a knob, a clamp, or any combination thereof. In some embodiments, the mechanical arm base 1328 is rigidly fixed to the crossbar 1310 and is not movable along the crossbar 1310. The mechanical arm base 1328 includes one, two, three, or more arm mounts 1802 configured to receive and hold a mechanical arm 442, which may be a robotic arm, a manually actuated arm, or a combination of mechanical and robotically actuated.

In some embodiments, the mechanical arm base 1328 includes a first arm 1802 mount and a second arm mount 1804, the first and second arm mounts configured for coupling with a first mechanical arm and a second mechanical arm. The first and second mechanical arms may carry a treatment probe 450 and an imaging probe 460, respectively. The first and second arm mounts may be spaced a fixed distance apart from one another along the crossbar 1310. In some instances, the fixed and known spacing between the arm mounts, and therefore the mechanical arms, can be used by a controller to align the treatment probe 450 and imaging probe 460 with respect to each other. For example, with a fixed position of the arm mounts 1802, 1804, the controller can determine a home position of the probes relative to each other, which can also facilitate proper alignment of the treatment probe axis relative to the imaging probe axis.

The mechanical arms are secured to the arm mount by any suitable mechanism, such as a screw, knob, cam, clip, detent, clamp, or any combination. In some embodiments, the mechanical arm base 1328 provides mounts for two mechanical arms to be affixed, and the arm mounts 1802, 1804 may be a fixed distance apart. This facilitates orientation and alignment of the probes mounted on the mechanical arms and further aids with calibration of the position of the probes.

Figure 19A:
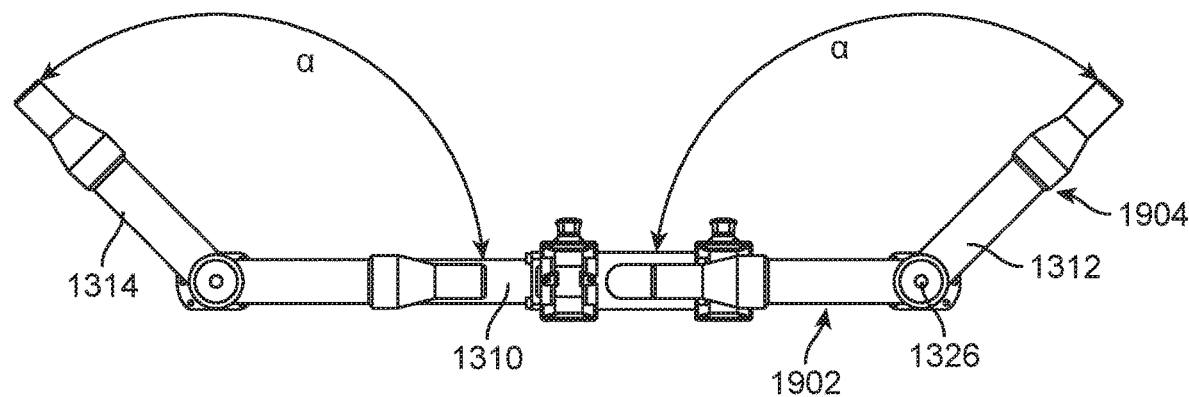
FIGS. 19A and 19B illustrate perspective views of a crossbar with mounts for use with a treatment system, in accordance with some embodiments.

With additional reference to FIGS. 19A and 199, an exemplary embodiment of a crossbar 1310 is shown and the range of motion of the mounting arms is shown along with a mounting configuration on various size patient supports. The mounting arms are attached to the crossbar 1310 by a crossbar coupling 1326 which allows pivotal movement of the mounting arms relative to the crossbar 1310. The mounting arms are selectively moveable between a first position 1902 which may be used for storage or during transport of the probe mounting and adjustment assembly 1600, and between a second position 1904 in which the mounting arms are rotated away from the crossbar 1310 and are spread apart from one another to facilitate mounting on a patient support. The mounting arms 1312, 1314 are selectively moveable through an angle α and can be secured in any orientation. In some embodiments, the range of motion a is at least 90°, and in some embodiments, the range of motion of the mounting arm is 100°, 110°, 120°, 130°, 140°, 150°, 160°, 170°, or 180°. In some embodiments the mounting arms 1312, 1314 are not positioned symmetrically, and therefore, the angle α is not consistent between the mounting arms. For example, a first mounting arm 1312 may be positioned at an angle α of 100° and a second mounting arm 1314 may be positioned at an angle α of 125°.

Figure 19B:
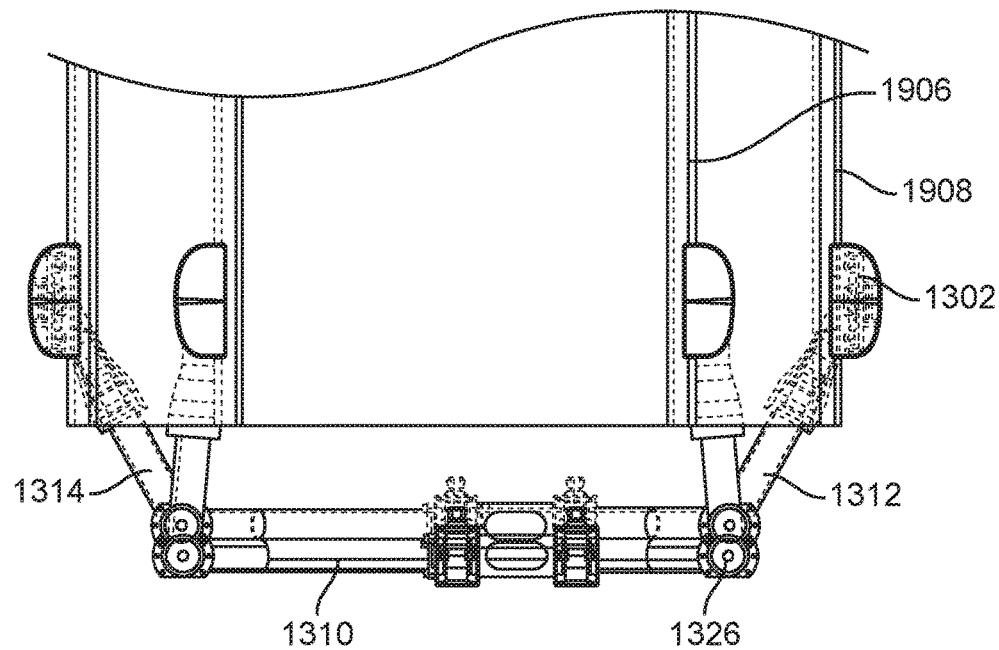

As shown in FIG. 19B, the mounting arms 1312, 1314 are illustrated with clamps 1302 attached thereto, and the mounting arms can be spread to accommodate patient supports having varying widths. For example, a first patient support 1906 has a first width and the mounting arms can be spread a first distance apart to position the clamps coupled to the mounting arms to mount onto the patient support. As the mounting arms are rotated through a range of motion to accommodate the patient support width, the clamps can be rotate so that the jaws of the clamp line up with the patient support. When mounting to a second patient support 1908 having a greater width than the first patient support, the mounting arms can be spread further apart to accommodate this larger sized patient support. As shown, the further the mounting arms are spread apart, the closer the crossbar 1310 is to the patient support. By providing the mounting arms with a range of pivotal motion relative to the crossbar 1310 and allowing the clamps 1302 to pivot relative to the mounting arms, the probe mounting and adjustment assembly 1600 can fit on many different sized patient supports. In some embodiments, a clamp 1302 may be secured to a longer mounting arm, which can be used with a crossbar 1310 for even more adjustability to fit a wider size of patient support.

Figure 20:
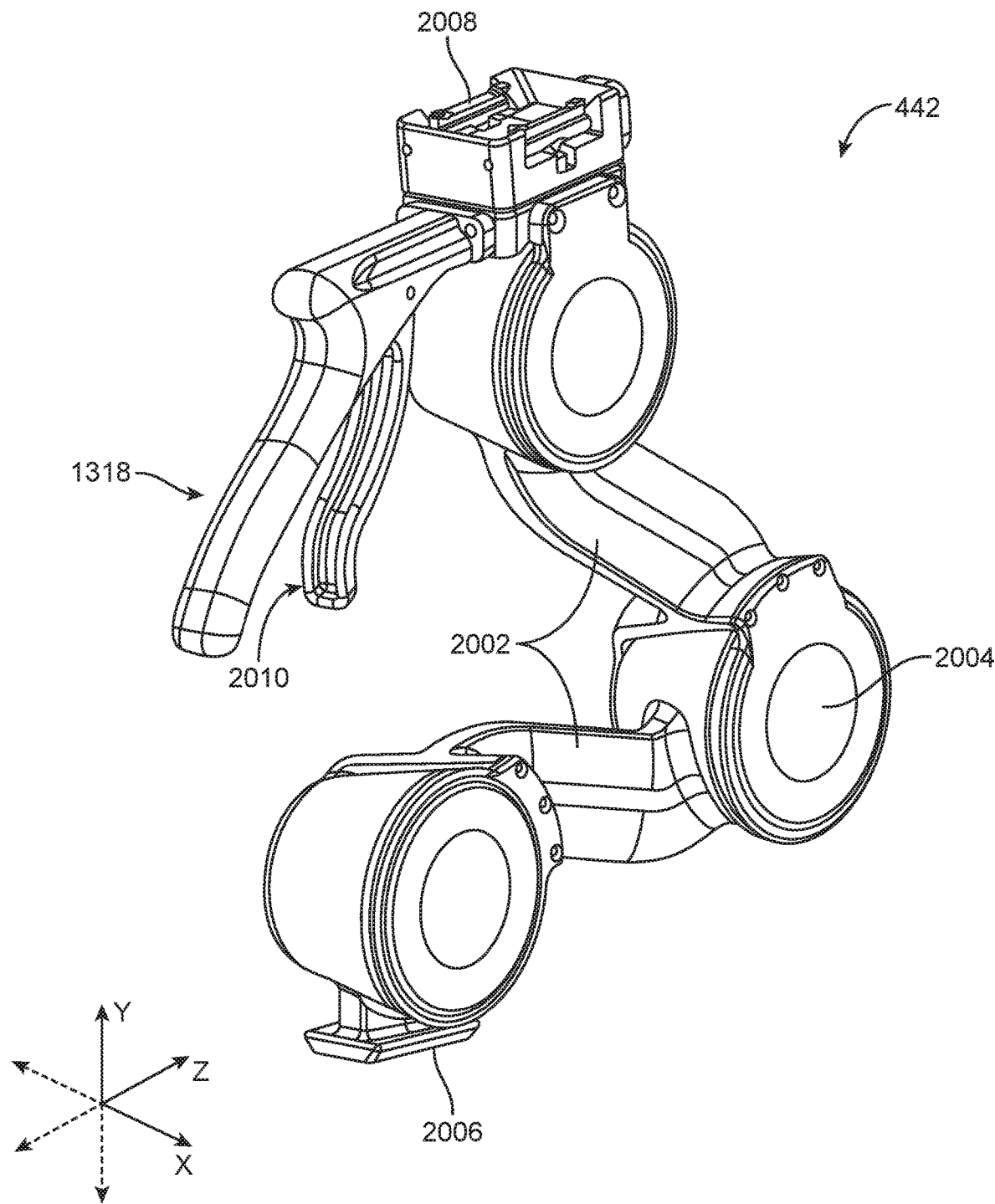
FIG. 20 illustrates a perspective view of a control handle, in accordance with some embodiments.

FIG. 20 illustrates an exemplary embodiment of a mechanical arm 442 with control handle 1318. The mechanical arm 442 may be a robotic arm and under control of one or more computing devices to allow precise movements of the robotic arm and a probe attached thereto. The robotic arm may be articulated with two, three, or more segments 2002 that are coupled by a joint 2004. The segments 2002 may be coupled by a joint 2004 that allows rotation between the adjacent segments 2002. The joint 2004 may be any suitable joint and may comprise a locking mechanism to allow selective movement of the mechanical arms 442 and locking of the mechanical arms. The joints 2004 may comprise a conical clutch locking joint and may include hydraulics for facilitating movement of the mechanical arm. Other suitable joints comprise a single-plate clutch, multi-plate clutch, locking cam interface, interlocking gear teeth, hydraulic actuation, pushrod actuation, motorized actuation, and cable actuation. Each joint 2004 may comprise one of a variety of kinematic joints including but not limited to a prismatic, revolute, parallel cylindrical, cylindrical, spherical, planar, edge slider, cylindrical slider, point slider, spherical slider, or crossed cylindrical joint, or any combination thereof. Moreover, each joint 2004 may comprise a linear, orthogonal, rotational, twisting, or revolving joint, or any combination thereof. In some embodiments, the joints 2004 have a limited range of motion to reduce the chance of pinch hazards.

The mechanical arm 442 comprises a mounting cleat 2006 to facilitate attachment of the mechanical arm 442 to the mechanical arm base 1328 coupled to the crossbar 1310 (FIG. 13). The mechanical arm 442 further includes a mount 2008 configured to accept a probe slider 1340. The probe slider 1340 may comprise a motor that allows a probe attached thereto to be advanced or retracted in the Z direction under computer control. The probe slider 1340, which in some embodiments may include a stepper motor, may be configured to provide fine control of the probe attached thereto. In some embodiments, the probe mounting and adjustment assembly 1600 comprises two mechanical arms, each with a probe mounted thereto, and each probe can be advanced in a controlled Z direction by a computing device and instructions to actuate the stepper motor of the probe slider 1340.

A control handle 1318 is attached to the mechanical arm 442 and can be used to manually manipulate the mechanical arm 442. A control lever 2010 is coupled to each joint 2004 within the mechanical arm. The control lever 2010 may be mechanically coupled to the joints, such as by a pull wire, belt, chain, or the like. Alternatively, the control lever 2010 may be electronically coupled to the joints 2004. As described herein, the joints 2004 may include actuators to allow robotic actuation of the mechanical arms 442. In some embodiments, the control lever 2010 is operable to disengage the actuator and allow manual manipulation of the mechanical arms 442. For example, the joints 2004 may comprise a clutch mechanism that selectively disengages the actuators within the joints 2004. Thus, when an operator pulls the control lever 2010, the clutches in the joints disengage the actuators and allow the operator to move the mechanical arm 442 by applying a force on the handle 1318. The mechanical arm 442 may provide for movement about the axes of each joint 2004, and may further allow for rotational movement about the mechanical arm base 1328. Manual actuation of the mechanical arm 442 allows an operator to position the mechanical arm 442 and an attached probe in the Y direction (e.g., vertical) and the Z direction (e.g., closer to or away from a patient). The operator can manually position a probe attached to the mechanical arm, calibrate the position of the probe tip, and instruct the one or more computing devices to operate the mechanical arms according to a treatment plan.

In some embodiments, the geometry of the mechanical arms 442 includes three rotating joints 2004 and enables fluid motion within a constrained surgical planning field area. In some embodiments, the mechanical arm 442 includes three rotating joints 2004 that all allow motion of the segments 2002 of the mechanical arm about the X axis. Consequently, the mechanical arm 442 can be freely moved in the YZ plane, and is limited in its ability to be manipulated in the XY plane. In some cases, the joints 2004 can be unlocked to allow fluid movement with low resistance, which allows precise positioning and tactile feedback of patient anatomy.

Figure 21:
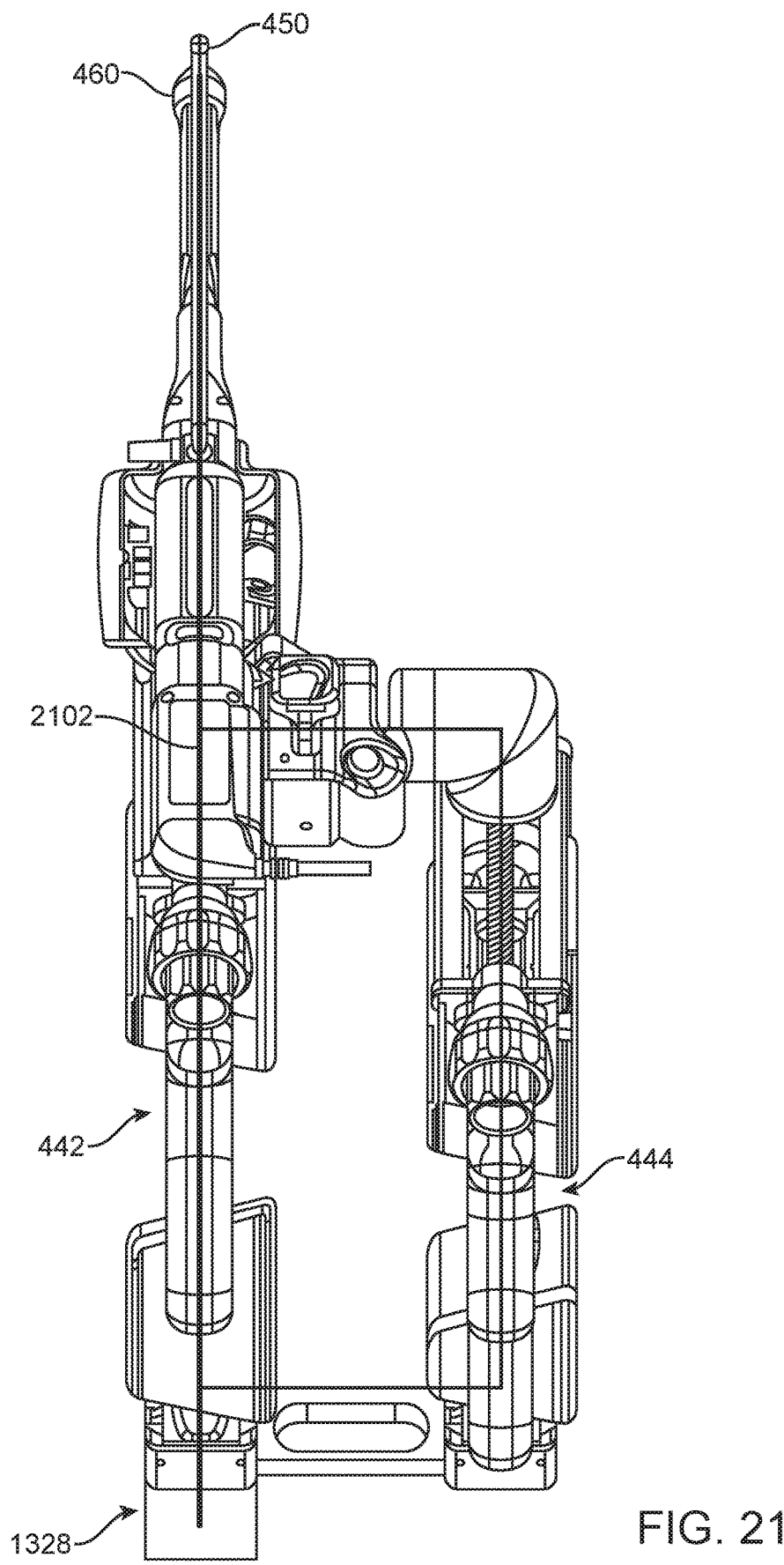
FIG. 21 illustrates a plan view of an imaging probe and a treatment probe coupled to respective control handles and showing co-planarity, in accordance with some embodiments.

FIG. 21 illustrates two mechanical arms with attached probes where the two probes are aligned in a vertical plane. A first arm 442 and a second arm 444 are coupled to a common base, such as a mechanical arm base 1328 carried on a crossbar 1310 of a probe mounting and adjustment assembly 1600. The first and second arms are mounted and spaced apart by a distance, which may be a fixed distance dictated by the mechanical arm base 1328. The first arm carries an imaging probe 460, the imaging probe 460 having an imaging probe axis 2102. The second arm 444 carries a treatment probe 450, the treatment probe 450 having a treatment probe axis. The mechanical arms are adjusted, if necessary, to orient the imaging probe axis 2102 to be parallel with the treatment probe axis. In some embodiments, the imaging probe axis 2102 and the treatment probe axis are coplanar in a vertical plane, which can facilitate proper positioning of the imaging probe 460 and the treatment probe 450 with respect to the anatomy of a patient undergoing a procedure. As described in reference to FIG. 13, the second arm 444 may incorporate a riser 1336 in the probe mount to elevate the treatment probe 450 above the imaging probe 460 so that the first arm and second arm 444 do not interfere with one another when the imaging probe axis 2102 and the treatment probe axis are aligned in a vertical plane. The imaging probe axis 2102 and the treatment probe axis can be coplanar in a plane that is not vertical, and may be substantially vertical, and they may be aligned under computer control of the first arm and second arm 444.

Figure 22:
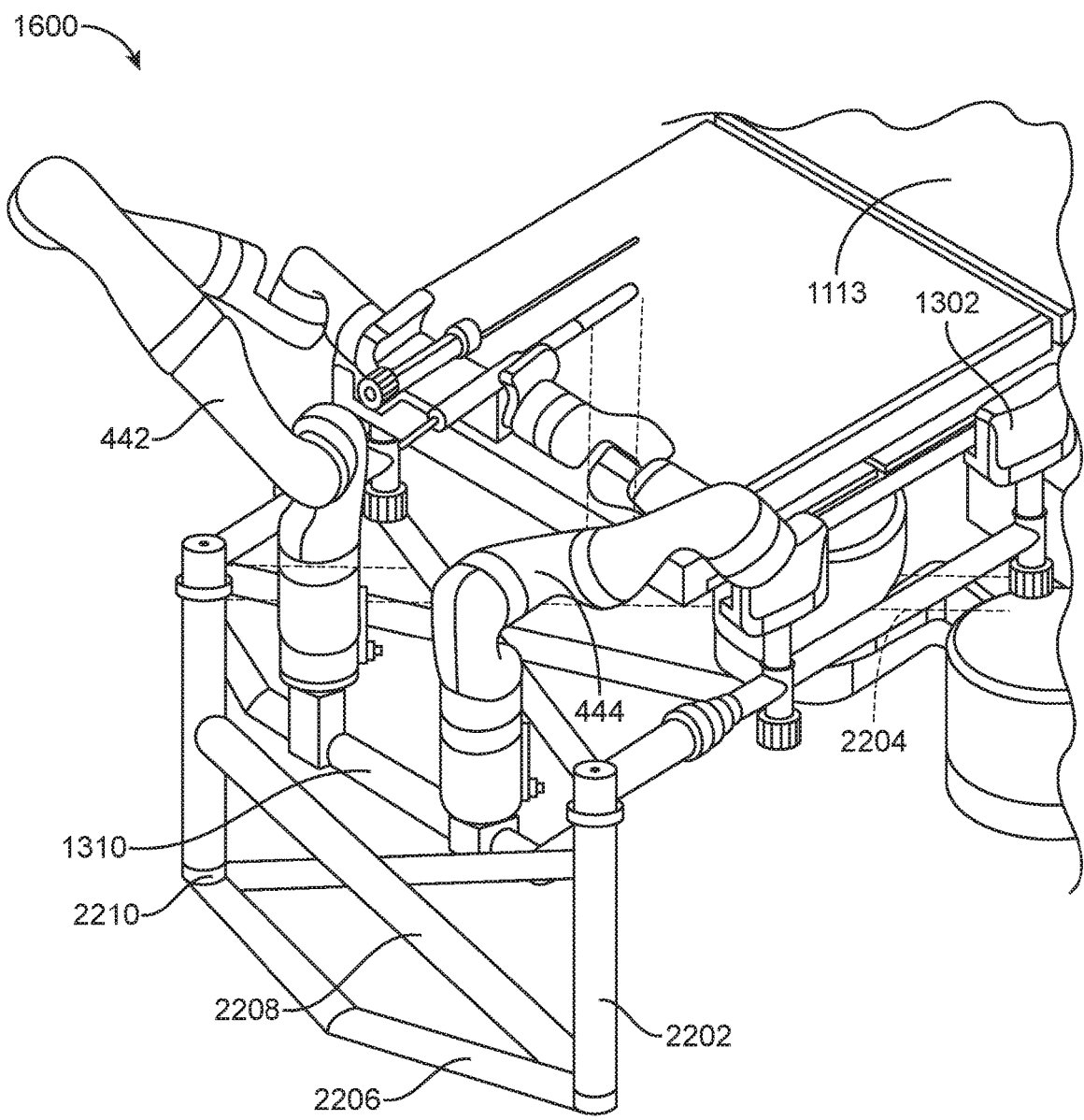
FIG. 22 illustrates a perspective view of a system for positioning imaging and treatment probes, in accordance with some embodiments, the system comprising clamps, braces, and robotic arms.

FIG. 22 illustrates an exemplary embodiment of a probe mounting and adjustment assembly 1600 attached to a patient support 1113. The crossbar 1310 carries two mechanical arms 442, 444, which are attached to the crossbar 1310 independently and can thus move independently along the crossbar 1310. The crossbar 1310 may also include additional support structure, such as legs 2202, bracing 2204, stretchers 2206, cross bracing 2208, and feet 2210. In some embodiments, the crossbar 1310 is coupled to one or more legs 2202 that extend from the crossbar 1310 to the floor. The legs 2202 may be adjustable and are configured to carry a large percentage of the weight of the probe mounting and adjustment assembly 1600. The one or more legs 2202 may include feet 2210 to spread the load out onto the ground and may include an anti-skid material to reduce the tendency of the legs 2202 to slide on the floor. One or more stretchers 2206 may be provided between two or more legs 2202 to reduce the tendency of the legs to splay in response to oblique forces.

One or more cross braces 2208 may be attached between the legs 2202 to provide rigidity of the support structure. One or more braces 2204 may be provided to increase the stiffness of the clamp coupling 1324, such as by connecting one or more braces from the top of the legs to a position near where the clamp connects to the mounting arm. The use of the legs, cross bracing, stretchers, braces, and any combination thereof can be selected to increase the rigidity and stiffness of the probe mounting and adjustment assembly 1600, in comparison to the probe mounting and adjustment assembly without the extra support structures. In some embodiments, the support structure reduces relative motion between the probe mounting and adjustment assembly and the patient support.

In addition or alternatively, one or more additional clamps 1302 can be connected to the legs, stretcher, crossbar 1310, or cross bracing at suitable locations. The additional clamps can be used in addition to the clamps already shown and described as being connected to the ends of the crossbar 1310, and can provide additional attachment points between the probe mounting and adjustment assembly 1600 and the patient support.

Figure 23:
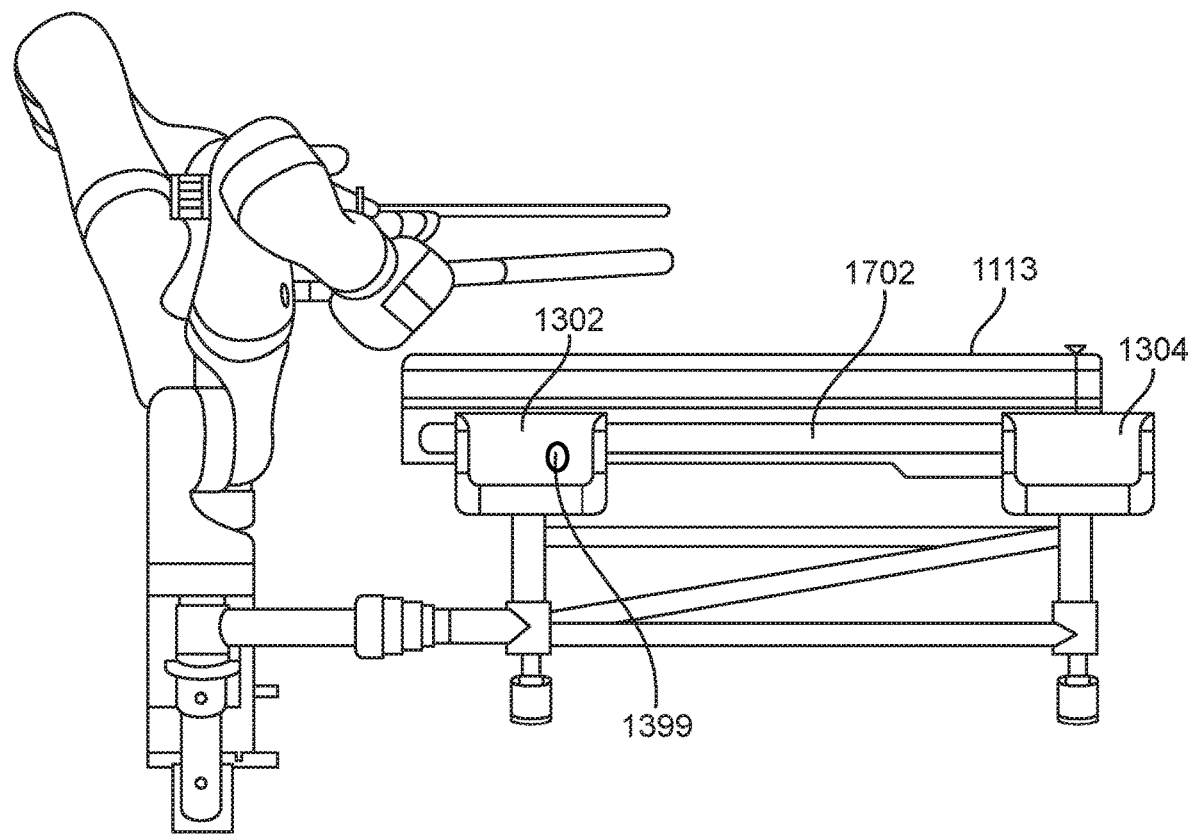
FIG. 23 illustrates a side view of a system for positioning imaging and treatment probes, in accordance with some embodiments.

FIG. 23 illustrates a probe mounting and adjustment assembly 1600 utilizing a second clamp on one side of the patient support. A clamp assembly may comprise a first clamp 1302 and a second clamp 1304 coupled together with bracing and spaced a fixed distance apart. The clamp assembly is configured to allow the first clamp 1302 and the second clamp 1304 to clamp to rail 1702 on the same side of a patient support 1113, such as by clamping on the same rail of the patient support. The first clamp 1302 and the second clamp 1304 may be rigidly spaced apart, or may have adjustability in their relative spacing to accommodate clamping to different patient support structures. In those embodiments in which the spacing between the first and second clamps is adjustable, the spacing between the clamps may be fixed rigidly once the relative spacing is selected. For instance, the spacing may be fixed rigidly by a screw, cam, lock, knob, or some other fixing structure.

A similar clamp assembly may be provided for the opposing side of the patient support and coupled to the crossbar 1310. In this configuration, there may be four clamps that couple the probe mounting and adjustment assembly 1600 to the patient support. The multiple attachment points to the patient support may reduce relative movement between the patient support and the probe mounting and adjustment assembly 1600 compared to using fewer clamps. It should be appreciated that the clamp assemblies illustrated in FIG. 23 can be used in conjunction with any of the other structures shown or described, such as the structure shown in FIG. 22 comprising one or more of legs, stretchers, braces, cross braces, and the like.

In some embodiments, a sensor 1399 is coupled to one or more clamps configured to couple to a rail. In some embodiments, the sensor 1399 comprises a plurality of sensors coupled to a clamp on each side of the rail. The sensor can be configured to measure loading of one or more of the clamp, the rail, or support coupled to a robotic arm. The one or more sensors can be located at any suitable location to measure loading, such as on the clamp, an extension coupled to the clamp or the support to which one or more robotic arms is coupled such as a crossbar. In some embodiments, the clamp is operatively coupled to one or more computing devices as described herein. In some embodiments, the processor is configured to generate an alert to the user when the loading exceeds a threshold amount. In some embodiments, the sensor is located on a jaw of the clamp, or another locking structure of the clamp, for example. In some embodiments, the pressure sensor, a piezo electric sensor, or a strain gauge, as described herein, for example.

Figure 24:
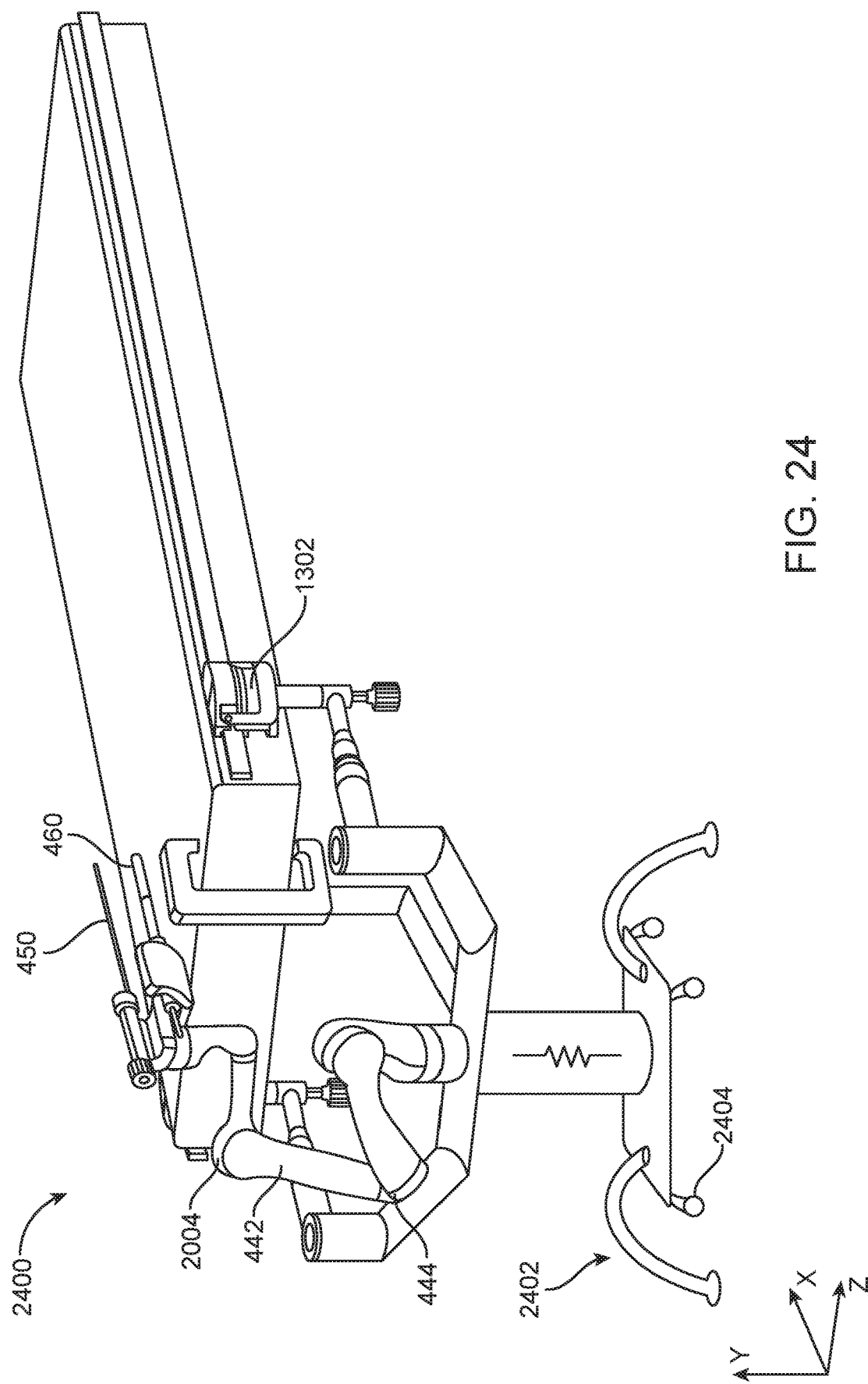
FIG. 24 illustrates a perspective view of a treatment system in accordance with some embodiments, the treatment system comprising a wheeled probe mounting and adjustment assembly.

FIG. 24 illustrates an exemplary embodiment of a treatment system 2400 as described herein comprising a mobile base 2402. The treatment system comprises a treatment probe 450 coupled to a first robotic arm 442, and an imaging probe 460 coupled to a second robotic arm 444. In some instances, the treatment probe 450 and the imaging probe 460 may be coupled to the same robotic arm and may have a probe mount that offer relative movement and alignment between the two probes.

The first robotic arm 442 and the second robotic arm 444 each comprises a proximal end and a distal end, the distal end is coupled to the treatment probe 450 and the imaging probe 460, respectively, and the proximal end is coupled to a common base comprising a mobile base 2402. The first robotic arm 442 may comprise a first arm coupling structure to couple to the treatment probe 450, and the second robotic arm 444 may comprise a second arm coupling structure to couple to the imaging probe 460. The treatment probe 450 may be coupled to the distal end of the first robotic arm 442 by a probe mount, which may comprise a linkage configured to allow movement of the treatment probe 450 as described herein (e.g., rotation, translation, pitch, etc.). Coupling of the treatment probe 450 to the first robotic arm 442 may be fixed, releasable, or user-adjustable. Similarly, coupling of the imaging probe 460 to the second robotic arm 444 may be fixed, releasable, or user-adjustable.

The first robotic arm 442 may articulate at one or more arm joints 2004. The imaging arm may articulate at one or more second arm joints. Each arm joint may be operably coupled with a computer-controllable actuator, such as a stepper motor, for example, to affect movement at the joint. Each arm joint may comprise one of a variety of kinematic joints including, but not limited to, a prismatic, revolute, parallel cylindrical, cylindrical, spherical, planar, edge slider, cylindrical slider, point slider, spherical slider, or crossed cylindrical joint, or any combination thereof. Moreover, each arm joint may comprise a linear, orthogonal, rotational, twisting, or revolving joint, or any combination thereof. In some examples, the first robotic arm 442 and the second robotic arm 444 provide arm joints 2004 that allow the treatment probe 450 and the imaging probe 460 to move with six degrees of freedom, and in some cases, with more degrees of freedom. The movement of the imaging probe 460 and the treatment probe 450 may be done manually, robotically under computer control, or a combination of both.

The treatment system may further comprise a console (not shown) as described herein. The console may be operably coupled with the mobile base 2402 via a power and communication cable, to allow control of the treatment probe 450 coupled to the mobile base via the first robotic arm 442. The treatment console comprises a processor and a memory having stored thereon computer-executable instructions for execution by the processor, to control various modules or functionalities of the treatment console, such as an energy source, infusion/flushing control, aspiration control, and other components as described elsewhere herein. The treatment console may further comprise a display in communication with the processor. The display may be configured to display, for example, one or more of subject vital signs such as heart rate, respiratory rate, temperature, blood pressure, oxygen saturation, or any physiological parameter or any combination thereof; status of a procedure; one or more previously taken images or sequence of images of a treatment site from one or more views; one or more real-time images or sequence of images of the treatment site from one or more views acquired by the imaging probe 460; a set of treatment parameters including but not limited to a treatment mode such as cutting or coagulating, an intensity of treatment, time elapsed during treatment, time remaining during treatment, a depth of treatment, an area or volume of the treatment site that his been treated, an area of the treatment site that will be treated, an area or volume of the treatment site that will not be treated, location information of the treatment probe 450 or the imaging probe 460 or both; treatment adjustment controls such as means to adjust the depth of treatment, the intensity of treatment, the location and/or orientation of the treatment probe 450, the depth of imaging, or the location and/or orientation of the imaging probe 460, or any combination thereof; or system configuration parameters.

The mobile base 2402 may further comprise one or more computing devices to control operation of the one or more robotic arms. For example, the mobile base may comprise processors and a memory having stored thereon computer executable instructions for execution by the one or more processors. The memory may have stored thereon instructions for operating the one or more robotic arms coupled to the mobile base. The processor may be operably coupled with the robotic arms via suitable electromechanical components to affect movement of the robotic arms. For example, each of the one or more joints of a robotic arm may comprise a step motor, and the processor may be operably coupled with the step motor at each joint to actuate the motor by a specified increment in a specified direction. Alternatively, the one or more robotic arms may be operably coupled with one or more processors of the console or a separate imaging console, wherein the one or mom console processors may be configured to execute instructions for controlling movement of the one or more robotic arms, and may communicate the instructions to the robotic arms via communication circuitry. The computer executable instructions for controlling movement of the robotic arms may be pre-programmed and stored on a memory, or may be provided by a user via one or more user inputs before or during treatment of the patient using the treatment system.

The one or more computing devices operably coupled with the first and/or second robotic arms may be configured to control movement of the arms to adjust the pitch, yaw, roll, and/or linear position of the treatment probe 450, the imaging probe 460, or both along the target site.

The treatment system may comprise one or mom user input devices to enable a user to control movement of the robotic arms, the mobile base, the imaging probe 460, the treatment probe 450, or any of the operable components associated with the treatment system under computer instructions. For example, the mobile base may comprise a keyboard, a mouse, a touchscreen, a digital pen, a touch pad, voice control input, and/or a footswitch. The user input devices may be configured to control operation of the first robotic arm 442 and/or the second robotic arm 444, for example via articulation of one or both robotic arms at one or more joints. The user input devices may be in communication with the one or more processors configured to control movement of the robotic arms. The user input devices can be located in any suitable place, for example, on a console, on a robotic arm, on a mobile base, and there may be one, two, three, four, or more user input devices used in conjunction with the treatment system to either provide redundant avenues of input, unique input commands, control discrete portions of the treatment system, or a combination.

In use, when a user inputs instructions by the user input devices, the user instructions can be received by the one or more processors, converted into electrical signals, and the electrical signals may be transmitted to the one or more computer-controllable actuators operably coupled with the one or mom robotic arms. The user input devices may control movement of one or both arms towards or away from a treatment position, a position of interest, a predetermined location, or a user-specified location, or any combination thereof.

Optionally, the user input devices may be configured to control operation of the treatment probe 450 and/or the imaging probe 460. For example, the user input devices may be configured to start, stop, pause, or resume treatment with the treatment probe 450 or start, stop, freeze, save, or display images with the imaging probe 460.

The mobile base may further have one or more deployable supports 2404 to stabilize the treatment system by creating contact with the floor. For example, one, two, three, or more deployable supports may extend from the mobile base and make contact with the ground once the mobile base is wheeled into position. The deployable supports 2404 may extend downward from the mobile base such that the wheels of the mobile base 2402 are lifted off the floor to reduce the likelihood that the treatment system may move during a procedure. The deployable supports 2404 may be manually actuated, or motor deployed when the treatment system in is position. In some instances, the deployable supports 2404 are manually actuated by a foot pedal that a user depresses to deploy and lock the deployable supports in place.

The treatment system may comprise a mobile power system, such as battery power that is electrically coupled to the treatment probe 450, imaging probe 460, display, one or more computing devices, the first and second robotic arms, and other equipment associated with the treatment system to allow the treatment system to be mobile and wheeled from room to room in a self-contained treatment system.

The treatment system may include one or more sensors configured to detect movement due to bumping the treatment system or the patient support, increase pressure on the treatment system or table support, movement of the patient support, or movement of the patient. The sensors can be configured to adjust the position of the imaging probe 460 and/or the treatment probe 450 in response to the sensed motion of the treatment system, patient support, or patient. In addition, an alarm may be configured to alert an operator if there is movement of the patient support, and may be configured to provide an audible, visual, or a combination alert in the event that movement of the patient support or the patient exceeds a threshold movement magnitude.

In some embodiments, the mobile base is provided with casters and may include three, four, five, or more casters. The casters may include brakes, which may be manual or powered, for limiting movement of the mobile base. One or more of the casters may have motors therein to allow movement of the mobile base, such as under control of the one or more computing devices. The casters allow the mobile base to transport the treatment system throughout a hospital and within a treatment room (e.g., operating room) for positioning the treatment system for a procedure.

The mobile base carries the crossbar 1310 to mount the robotic arms and two, three, four, or more clamps to the patient support. In some embodiments, two clamps are held by opposing adjustable mounting arms to allow the clamps to be positioned on lateral sides of the patent support. According to some embodiments, additional clamps are provided to increase the number of engaging supports between the treatment system and the patient support to increase the rigidity of the coupling between the treatment system and the patient support. For instance, one or more clamps 1302 can be coupled to the crossbar 1310 and clamped onto a proximal portion of the patient support. Additional clamps can be coupled to the crossbar 1310 and clamped onto other portions of the patient support, such as a base, leg, support, frame, rail, or other structure of the patient support.

The embodiments shown and described offer numerous advantages not seen before. Deployment of the probe mounting and adjustment assembly 1600 is efficient, can be handled easily by a single person and the flexible design works with a wide range of patient supports, patient presentations, and offers the ability to be installed offset from the end of a patient support to facilitate mounting stirrups on the end of the patient support.

According to some embodiments, the individual components of the probe mounting and adjustment assembly 1600, once disassembled, have a weight of less than about 8 lbs, or less than about 10 lbs, or less than about 12 lbs.

Figure 25:
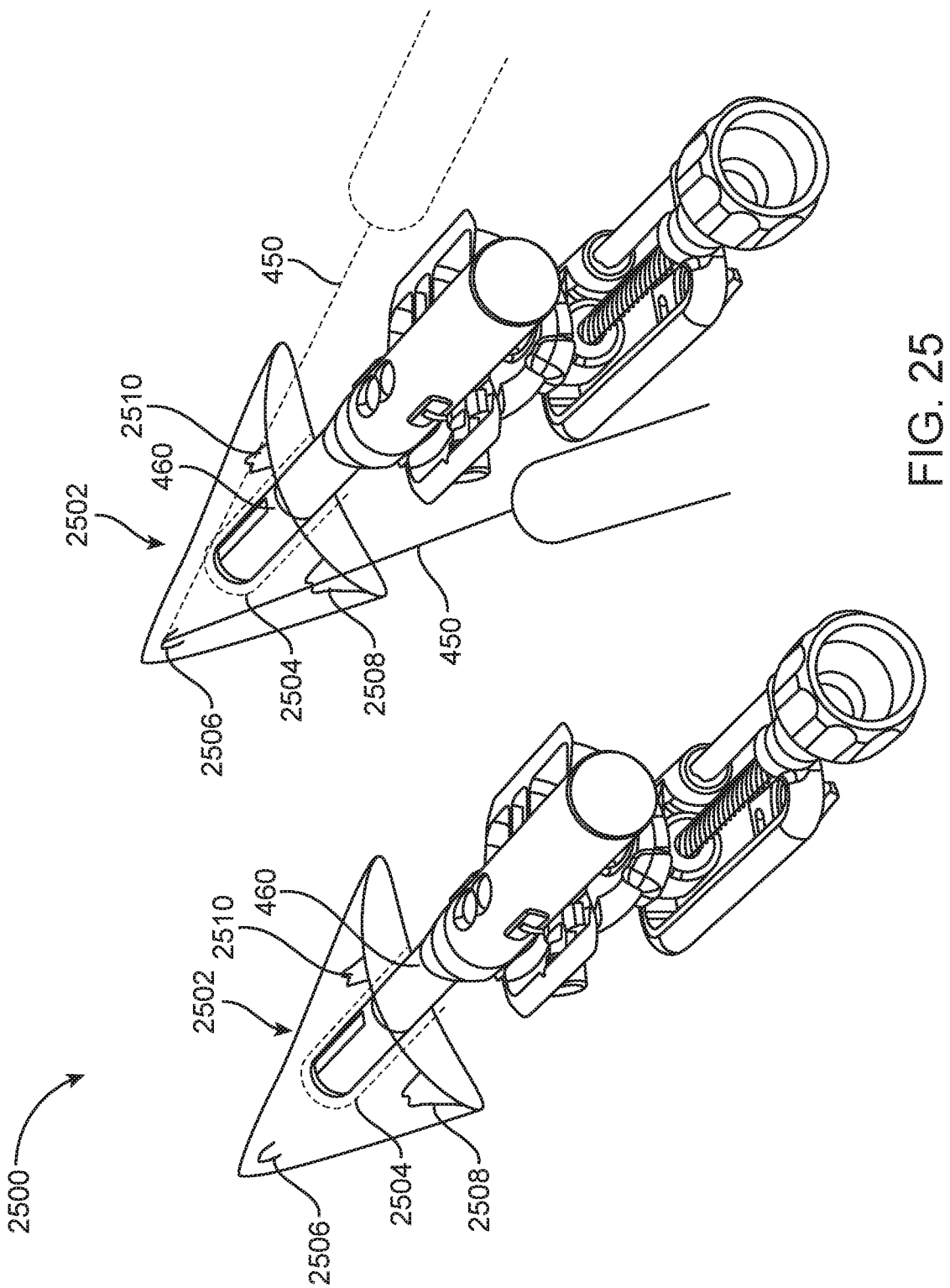
FIG. 25 illustrates a system for locating and calibrating one or more probes, in accordance with some embodiments.

FIG. 25 illustrates a system 2500 for one or more of locating a probe, calibrating a probe, or training a system with calibrated probe movements. In some embodiments, a calibration device 2502 comprises receptacles to receive the treatment probe 450 and the imaging probe 460. The receptacles are sized and shaped to receive the probes and to allow the probes to move into positions that may be used during surgery. The positions of the arms and probes can be monitored during the calibrated movement prior to placement of the probes in the patient.

In some embodiments, the processor is configured with instructions to receive mechanical movements of the probe to establish one or more boundaries, for example for collision avoidance with another probe or another robotic arm. In some embodiments, the processor is configured to implement a "teaching session" to establish the boundaries, for example, prior to placing one or more of the probes within the patient. During this teaching session a sterile protective calibrated guide 2502, also referred to as a calibration device, can be provided and the imaging probe 460 can be inserted therein and be used to measure geometric position data for incorporation into a positional database of the robotic arm. In some embodiments, this guide comprises one or more of a capture lumen 2504 for receiving the imaging probe 460, a touch point 2506 for identifying the tip of the treatment probe 450, one or more dual notch structures 2508, 2510 for identifying the linear shaft location relative to the imaging probe 460, or a planar surface identifying 'do not cross' anatomical planes. Alternatively or in combination, a plurality of cameras and machine vision software instructions can be used to measure the probe positions in 3D space relative to their respective origins and create a database of allowable relative positions between the two probes.

A calibration device 2502 may be provided sterile with features that enable positioning onto a first probe 460 and placement for calibration of second probe 450 relative to the first probe 460. A capture lumen 2504 or open structure allows one way to position first probe 460 into a known position and orientation. The first probe 460 may be moved within the capture lumen 2504 with controlled depth of placement into the calibration device 2502 and an envelope of spatial boundary, e.g. a bounding volume, may be created and saved to a database.

In some embodiments, the calibration device 2502 includes a tip location pocket 2506 to detect contact with the tip of the second probe 450. A first notch structure 2508 provides a guide for the shaft of the second probe 450 as the second probe 450 is advanced to the touch point 2506. The combination of the first notch structure 2508 and the touch point 2506 thus provides an instructional path for placement of the second probe 450, the positions of which can be stored in the positional database, which also stores the relative locations of the first probe 460 and the second probe 450.

With the tip of a second probe in the tip location pocket of the calibration device 2502 the shaft of the second probe can be positioned relative to the shaft of the first probe and a signal can be sent to a processor to note the positions of both arms holding the first probe and second probe.

Similarly, the shafts of the first probe 460 and the second probe 450 can be moved to another spatial orientation relative to each other, such as by advancing the second probe 450 along the second notch structure 2510 and a calibration signal can be sent to the processor to store the relative position of the first probe and second probe.

Additionally, the calibration device 2502 can be configured to accept a second probe feature to detect and determine a rotational assurance of the second probe 450 and, similarly, the rotational position of the first probe 460 which may be used to align the treatment probe nozzle relative to both transverse and sagittal plane of ultrasound, for example.

The calibration device 2502 thus may provide a secure physical capture region to assure simple placement and docking of tip against the calibration device 2502, the position and orientation of which can be stored in a spatial database to teach the robotic arm controller system an acceptable spatial envelope of relative position and orientation of the first probe 460 with respect to the second probe 450.

The methods and apparatus disclosed herein can be configured in many ways, and may comprise fiducials and a processor configured with instructions to provide navigation and surgical guidance to a user such as a surgeon. For example, one or more of the imaging probe 460, e.g. TRUS probe, the treatment probe 450, the proximal end of the treatment probe 450, the proximal end of the imaging probe 460, or the robotic arm may comprise navigation fiducials. These navigational fiducials can be detected with sensors to provide position and orientation information of the treatment probe 450 and imaging probe 460 relative to the patient and a fixed reference frame such as a base as described herein. The fiducials may comprise reflective structures, energy emitting structures, coils, magnets or visual references, for example. These fiducials can provide positional information to the computing navigation system to inform a user of errant motion. The positional information can be used to measure and control the location of the treatment and imaging probes and movement. The positional information can also be shown on a display visible to a user. The processor may comprise instructions to show treatment fiducials on a display in relation to target locations on a patient and register real time images of the patient with the target treatment profile in real time, for example.

In some embodiments, the positional information is used to monitor relative motion and as a feedback loop for controlling intentional motion or responding to unintentional motion.

Figure 26:
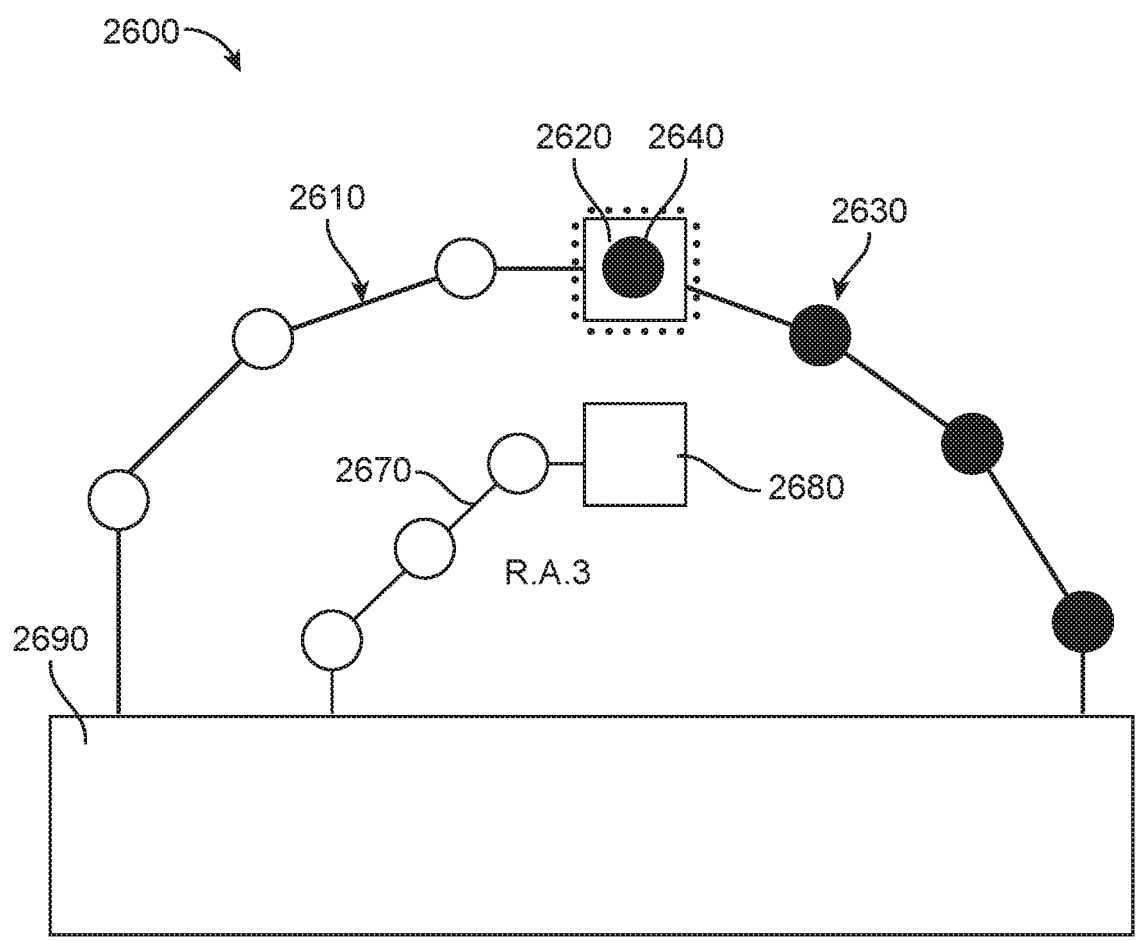
FIG. 26 illustrates an arm coupled to a sheath, a robotic arm coupled to a treatment probe, and an arm coupled to an ultrasound probe, in accordance with some embodiments.

FIG. 26 illustrates a system 2600 comprising an arm 2610 coupled to a sheath 2620, a robotic arm 2630 coupled to a treatment probe 2640, and an arm 2670 coupled to an ultrasound probe 2680. The arms are coupled to a base 2690, which may comprise any suitable base as described herein, such as a crossbar coupled to rails of a patient support, for example. The arm 2610 may comprise any arm as described herein, and may comprise a robotic arm, or a manually adjustable arm configured to lock into position, for example. The sheath 2610 is configured for insertion into a lumen of the patient such as a urethra, and may comprise a stiff sheath or a flexible sheath, for example. The robotic arm 2630 may comprise any suitable robotic arm as described herein. The treatment probe 2640 may comprise any suitable treatment probe as described herein. The arm 2670 may comprise any suitable arm as described herein, an may comprise a manual lockable arm or a robotic arm as described herein. The ultrasound probe 2680 may comprise any suitable ultrasound probe as described herein, for example a TRUS probe. The robotic arms, treatment probe and ultrasound probe are operatively coupled to a processor as described herein.

Figure 27:
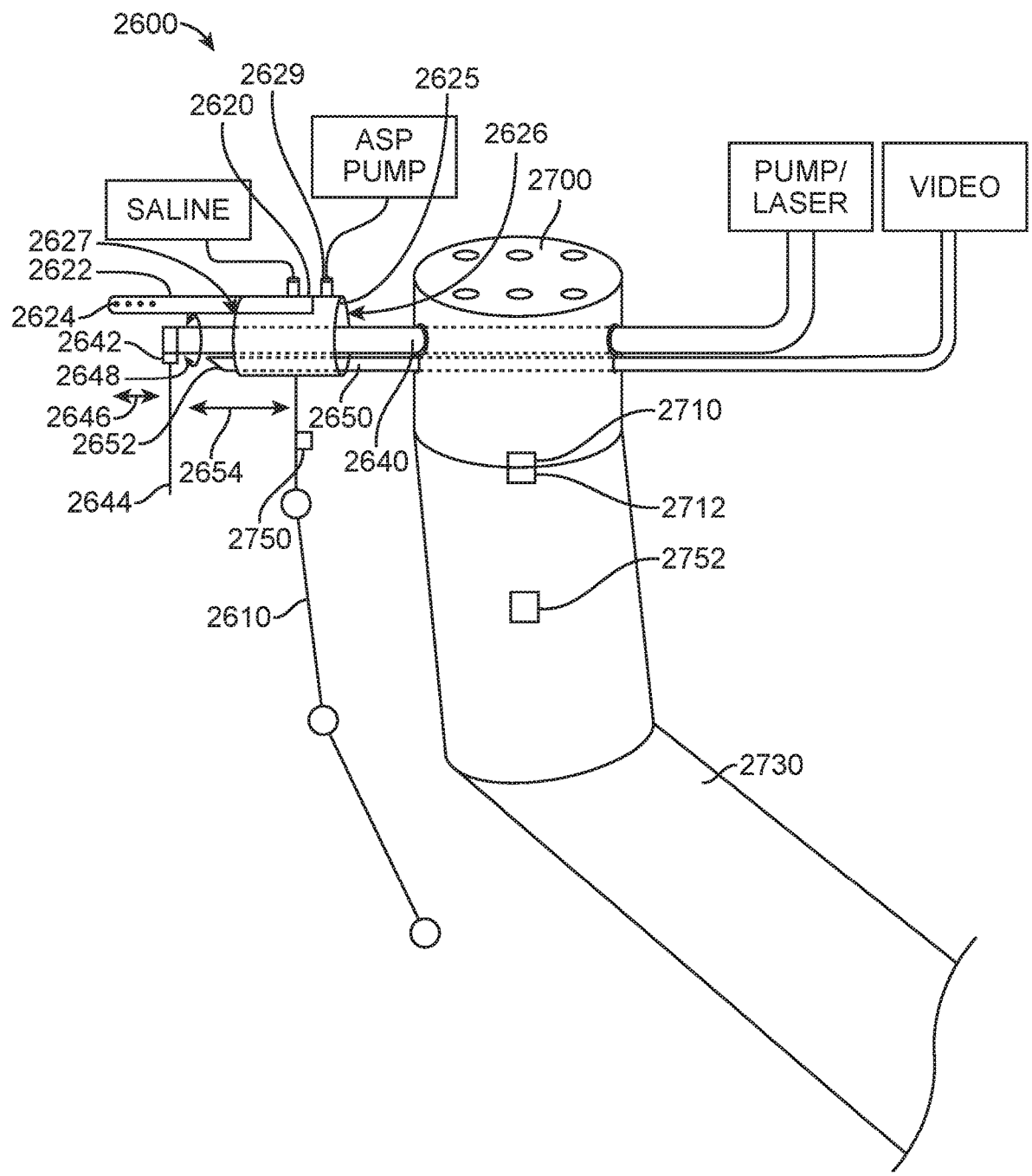
FIG. 27 illustrates a system comprising a robotic arm coupled to a treatment probe and an arm coupled to a sheath as in FIG. 26.

FIG. 27 illustrates a robotic arm 2630 coupled to a treatment probe 2640 and an arm 2610 coupled to a sheath 2620 as in FIG. 26. The sheath 2620 is coupled to arm 2610. In some embodiments, the sheath 2620 comprises an irrigation lumen 2622 extending to one or more openings 2624 to irrigate the surgical site. The irrigation lumen can be connected to a source of irrigation fluid such as saline. The sheath may comprise a lumen 2626 sized to receive the treatment probe. The lumen 2626 comprises a proximal opening 2625 and extends to a distal opening 2627. In some embodiments, the sheath 2620 comprises an aspiration channel 2629 extending to an opening into lumen 2620 to fluidically couple the lumen 2626 to an aspiration pump to remove resection products. The treatment probe 2640 is coupled to a source of energy as described herein such as a laser, water pump, or electrical source, and comprises an energy release structure such as nozzle, optical fiber end, aperture, or electrode to direct energy toward the tissue. The treatment probe is configured to translate 2646 and rotate 2648 energy 2644 from the treatment probe. An endoscope 2650 extends into the sheath. The endoscope comprises a viewing port such as a viewing port of an endoscopic camera 2652, which is configured to translate 2654. The endoscope is coupled to a video display to view the treatment probe and treatment site with the endoscope.

A coupling 2700 is coupled to an end portion of the robotic arm 2630. The coupling 2700 comprises one or more engagement structures 2710 to couple to the end portion of the robotic arm. The robotic arm 2630 comprise one or more corresponding engagement structures 2712 to connect to the coupling 2700 to the robotic arm. In some embodiments, the coupling 2700 comprises internal structures such as linkages and actuators as described herein to translate one or more of the treatment probe, the endoscope, the irrigation lumen or the aspiration lumen relative to the robotic arm. In some embodiments the coupling 2700 is configured to rotate the treatment probe independently of the endoscope, the irrigation lumen and the aspiration lumen. In some embodiments, the coupling 2700 comprises a structure to receive a treatment probe and define an orientation of the treatment probe with respect to the coupling. The structure to receive the treatment probe may comprise one or more of an aperture or a channel coupled to the linkage, for example. In some embodiments, the coupling 2700 comprises an engagement structure to couple to an end portion of a robotic arm to establish an orientation of the treatment probe with respect to the end portion of the robotic arm.

In some embodiments, one or more of the arm or the sheath comprises a sensor 2750 to determine the orientation of the sheath when placed in the patient. In some embodiments, the robotic arm 2752 comprises an orientation sensor 2752 to determine the orientation of the treatment probe 2640 coupled to the robotic arm. Alternatively or in combination with the sensors, the joint states of the robotic arm 2630 can be used to determine the orientation of the treatment probe, and the joint states of the arm 2610 can be used to determine the orientation of the sheath.

In some embodiments, the treatment probe comprises an elongate axis and the sheath comprises an elongate axis to receive the treatment probe.

The system can be configured in many ways to treat the patient in many ways. In some embodiments, the sheath is sized and shaped for insertion into the patient. The sheath comprises an elongate axis, and an arm is coupled to the sheath. The treatment probe comprising an energy source and an elongate axis. The treatment probe sized and shaped for insertion into a lumen of the sheath. The robotic arm is coupled to the treatment probe, and configured to align the elongate axis of the treatment probe with the elongate axis of the sheath and to advance the treatment probe into the sheath. The robotic arm coupled to the treatment probe is configured to align the axis of the treatment probe with the axis of the sheath prior to advancing the treatment probe into the sheath.

In some embodiments, the robotic arm comprises a sensor to determine an orientation of the treatment probe and the sensor comprises one or more of an accelerometer, a gyroscope, or an inertial measurement unit (IMU). Alternatively or in combination, the arm coupled to sheath comprises a sensor to determine an orientation of the sheath. The sensor may comprise one or more of an accelerometer, a gyroscope, or an IMU.

In some embodiments, sheath comprises a proximal opening to receive the treatment probe and a distal opening and the treatment probe comprises a length sufficient to extend to at least the distal opening. In some embodiments, the treatment probe is dimensioned for the energy source to extend to at least the distal opening when the treatment probe has been advanced into the sheath.

In some embodiments, the energy source extends to at least the distal opening with a gap between an end portion of the robotic arm and the sheath.

Although reference is made to the coupling structure rotating the treatment probe, in some embodiments robotic arm 2630 is configured to rotate the treatment probe.

The processor can be coupled to one or more of the arm 2610, the arm 2630, or the arm 2720. In some embodiments, processor configured with instructions to advance the treatment probe into the sheath, which can facilitate the alignment of the treatment probe with the sheath. In some embodiments, the processor is configured to align the elongate axis of the treatment probe with the elongate axis of the sheath. In some embodiments, the processor is configured with instructions to receive an input indicating that the elongate axis of the treatment probe has been aligned with the elongate axis of the sheath and to advance the treatment probe along the elongate axis of the treatment probe in response to the input. The input may comprise a user input, or the input may comprise an input from sensor data. In some embodiments, the arm coupled to the stiff sheath comprises a sensor operatively coupled to the processor to determine an orientation of the sheath, and the processor is configured with instructions to orient the treatment probe with the sheath in response to the orientation of the stiff sheath measured with the sensor. In some embodiments, the robotic arm comprises a sensor to determine an orientation of the treatment probe. Alternatively or in combination, the orientation of the treatment probe can be determined from the joint states of the robotic arm. In some embodiments, the orientation of the sheath is determined from joint states of the arm coupled to the stiff sheath.

Figure 28A:
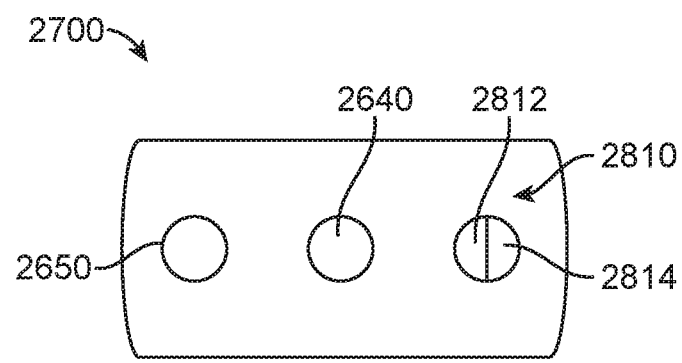
FIG. 28A illustrates a coupling to couple a robotic arm to a treatment probe.

FIG. 28A illustrates a coupling 2700 to couple a robotic arm 2630 to a treatment probe 2640. In some embodiments, the coupling 2700 is configured to couple the treatment probe 2740, the endoscope 2650, an irrigation lumen 2812 and an aspiration lumen 2814 to the robotic arm. Each of these lumens may be defined by an elongate tube defining the lumen. In some embodiments, the irrigation lumen and the aspiration lumen comprise lumens of a dual lumen tube such as a catheter. Alternatively, the irrigation lumen and the aspiration lumen may comprise separate catheters.

Figure 28B:
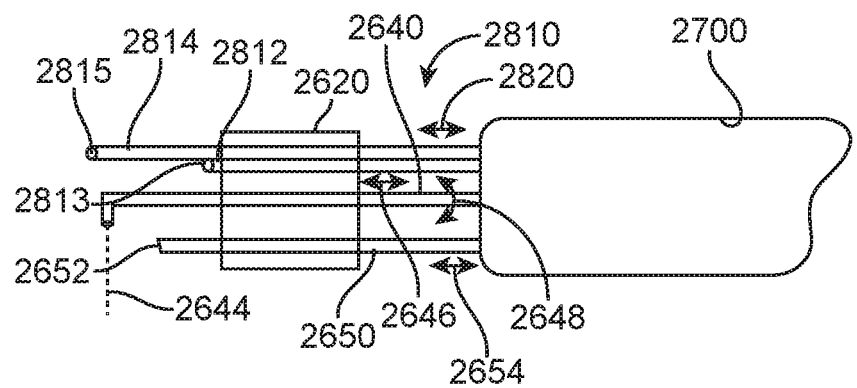
FIG. 28B illustrates movements of the treatment probe, the endoscope, the irrigation lumen and the aspiration lumen provided by the coupling as in FIG. 28A.

FIG. 28B illustrates movements of the treatment probe 2640, the endoscope 2650, the irrigation lumen 2812 and the aspiration lumen 2814 provided by the coupling as in FIG. 28A. The irrigation lumen 2812 extends to an opening 2813 to release an irrigation fluid. The aspiration lumen 2814 extends to an opening 2814 to receive resection products. The sheath 2620 is sized to receive these lumens and the corresponding structures defining the lumens, e.g. tubes. The sheath 2620 is sized to receive the treatment probe. In some embodiments, the sheath 2620 is sized to receive the endoscope 2650.

The coupling 2700 can be configured in many ways to move one or more of the treatment probe, the endoscope, the irrigation lumen or the aspiration lumen. In some embodiments, the coupling connects to the robotic arm 2630 and the robot arm provides motion to the treatment probe. For example, the robotic arm can be configured to rotate the treatment probe. Alternatively or in combination, the robotic arm can be configured to rotate and translate the treatment arm.

In some embodiments, the coupling 2700 is configured to rotate the treatment probe. For example, the coupling can be configured to rotate 2648 the treatment probe. The robotic arm can be configured to translate 2646 the treatment probe while the coupling 2700 rotates the treatment probe. In some embodiments, the endoscope 2750 is configured to translate 2654 with the treatment probe. In some embodiments, the irrigation lumen and the aspiration lumen are configured to translate with the treatment probe.

In some embodiments, the coupling 2700 is configured to provide independent translational movement to the treatment probe and one or more of the endoscope, the irrigation lumen, or the aspiration lumen. In some embodiments, the coupling is configured to provide independent translation movement to the treatment probe, the endoscope, and one or more of the irrigation probe or the aspiration probe.

Figure 29:
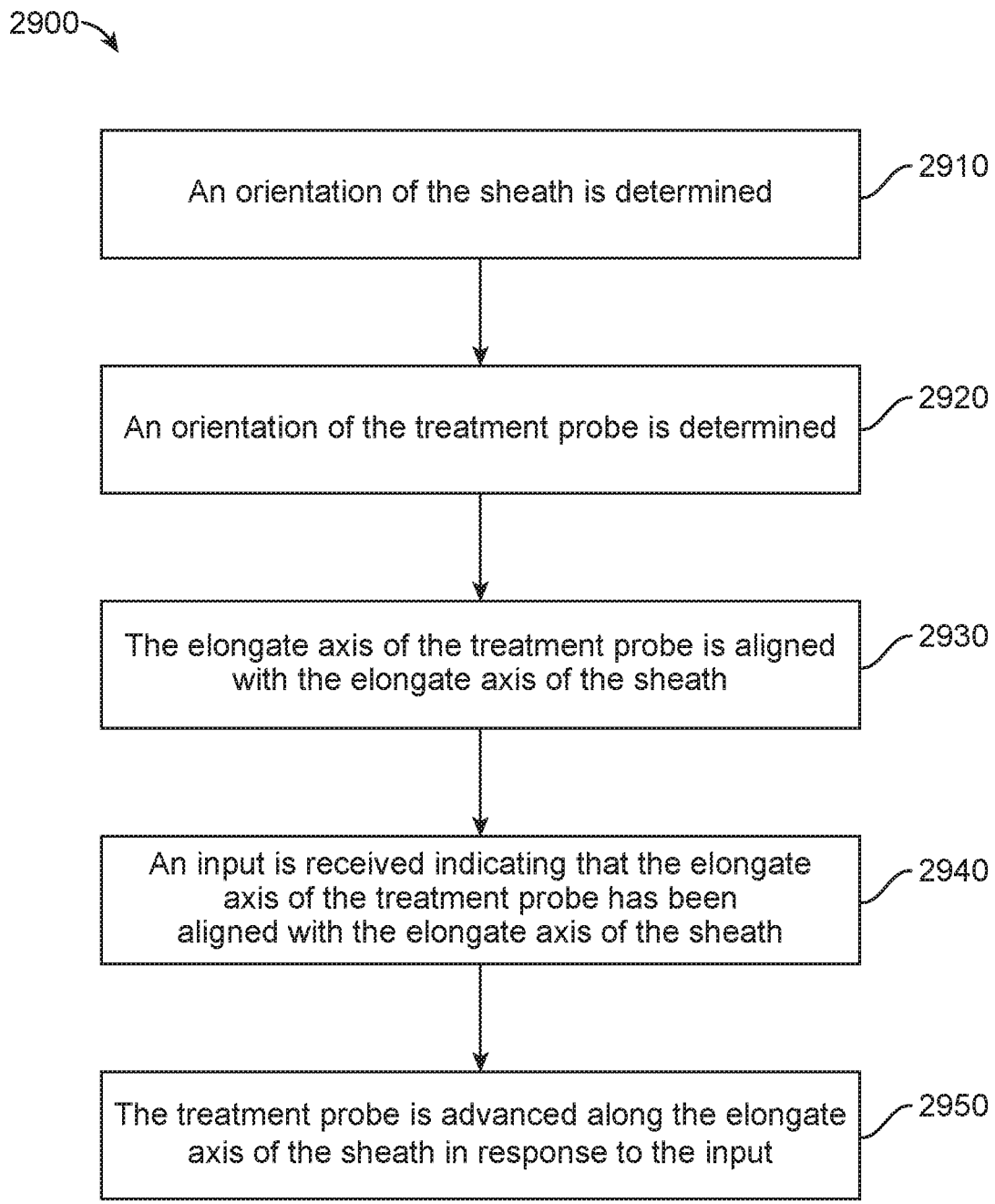
FIG. 29 illustrates a method of treatment, in accordance with some embodiments.

FIG. 29 illustrates a method 2900 of treatment, in accordance with some embodiments.

At a step 2910, an orientation of the sheath is determined. The orientation of the sheath can be determined from one or more sensors coupled to the sheath, such as an orientation sensor on the arm coupled to the sheath or from the joint states of the arm coupled to the sheath.

At a step 2920, an orientation of the treatment probe is determined. The orientation of the treatment probe can be determined from one or more sensors coupled to the treatment probe, such as an orientation sensor on the arm coupled to the treatment probe or from the joint states of the arm coupled to the treatment probe.

At a step 2930, the elongate axis of the treatment probe is aligned with the elongate axis of the sheath. This alignment can be performed manually. Alternatively, the processor can be configured with instructions to align the elongate axis of the treatment probe with the elongate axis of the sheath.

At a step 2940, an input is received indicating that the elongate axis of the treatment probe has been aligned with the elongate axis of the sheath. This input may comprise a user input based on visualization or an input from sensor data, or a combination thereof.

At a step 2950, the treatment probe is advanced along the elongate axis of the sheath in response to the input.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or mom of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

As used herein, the terms "coarse" and "gross" are used interchangeably.

As used herein, the terms "one or more computing devices" and "processor" are used interchangeably.

The present disclosure includes the following numbered clauses.

Clause 1. A system of treating or imaging tissue of a patient, said system comprising: a probe sized for insertion into the patient; a robotic arm configured to couple to the probe; one or more computing devices operatively coupled to the robotic arm and configured with instructions for: establishing an allowable range of motion for the probe, the allowable range of motion stored on a memory of the one or more computing devices; treating or imaging the target tissue of the patient with the probe; and moving the robotic arm to affect movement of the probe within the allowable range of motion for the probe.

Clause 2. The system of clause 1, wherein the probe is configured to couple to the robotic arm while the robotic arm is in a passive mode.

Clause 3. The system of clause 1, wherein the allowable range of motion for the probe is established while the robotic arm is in a passive mode.

Clause 4. The system of clause 1, wherein establishing the allowable range of motion for the probe comprises establishing the allowable range of motion for the probe in response to a user input.

Clause 5. The system of clause 1, wherein establishing the allowable range of motion for the probe comprises establishing the allowable range of motion for the probe in response to a position of the probe.

Clause 6. The system of clause 5, wherein the position of the probe relative to the target tissue is determined in response to one or more tissue landmarks in one or more images of the target tissue.

Clause 7. The system of clause 1, further comprising updating the allowable range of motion for the probe in real-time.

Clause 8. The system of clause 1, further comprising a user input device operably coupled with one or more computing devices to provide one or more user instructions for controlling movement of the robotic arm, and wherein moving the robotic arm under control of the one or more computing devices comprises moving the robotic arm in response to the one or more user instructions for controlling movement of the robotic arm.

Clause 9. The system of clause 8, wherein the user input device comprises one or more of a controller near the end of the robotic arm, a user interface on a display screen, a user interface on a console, or a controller that responds to forces on the end of the arm provided by the user to guide a probe on the robotic arm into position.

Clause 10. The system of clause 1, further comprising one or more force sensors operably coupled with the probe and one or more computing devices to detect compression of a tissue of the patient with the probe.

Clause 11. The system of clause 10, wherein the one or more computing devices comprise a processor configured with instructions to interrupt the treatment in response to a detected compression of the tissue exceeding a predetermined threshold level of compression.

Clause 12. The system of clause 10, wherein the one or more force sensors are operatively coupled to the robotic arm.

Clause 13. The system of clause 12, further comprising one or more motion sensors operably coupled with the probe and the one or more computing devices to detect movement of the patient, and wherein the one or more computing devices are configured to adjust a position of the probe in response to the detected movement of the patient.

Clause 14. The system of clause 1, wherein the robotic arm comprises a passive mode to manually adjust the probe to a manually set position.

Clause 15. The system of clause 14, wherein in the passive mode the probe is supported with the robotic arm and the probe comprises a plurality of sensors at an interface between the robotic arm and the probe to receive user input from a handle coupled to the plurality of sensors for the user to direct the probe.

Clause 16. The system of clause 15, wherein a handle coupled to the plurality of sensors is configured to receive user manipulations of the handle and the plurality of sensors at the interface is coupled to a processor of the one or more computing devices to manipulate the probe in response to the user manipulations of the handle.

Clause 17. The system of clause 16, wherein the plurality of sensors is configured to detect user manipulations of the handle with 6 degrees of freedom and wherein the processor is configured to move the probe with 6 degrees of freedom with motion corresponding to the 6 degrees in response to the user manipulations.

Clause 18. The system of clause 14, wherein to manually adjust the robotic arm in the passive mode comprises manually adjusting the probe in one or more of at least one rotational axis or at least one translational axis.

Clause 19. The system of clause 18, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 20. The system of clause 19, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 21. The system of clause 14, wherein the manually set position of the probe is maintained after the robotic arm is released from manual adjustment.

Clause 22. The system of clause 21, wherein the robotic arm is configured to maintain the manually-set position with a tolerance in one or more of a rotational axis or a translational axis and optionally wherein the tolerance is within 5° for rotation about one or more of three axes and 5 mm for translation along the one or more of three axes and optionally for each of the one or more of three axis and optionally wherein a rotational tolerance is within 3° and optionally wherein a translational tolerance is within 3 mm and optionally 2 mm.

Clause 23. The system of clause 21, wherein the probe comprises an imaging probe.

Clause 24. The system of clause 21, wherein the probe comprises a treatment probe and the robotic arm comprises a first robotic arm, the system further comprising: an imaging probe sized for insertion into the patient; a second robotic arm coupled to the imaging probe; and wherein the one or more computing devices is configured with instructions for establishing an allowable range of motion for the imaging probe.

Clause 25. The system of clause 24, wherein the imaging provide is configured to image the target site of the patient with the imaging probe and wherein the second robotic arm is configured to move under control of the one or more computing devices to affect movement of the imaging probe within the allowable range of motion for the imaging probe.

Clause 26. The system of clause 1, wherein the one or more computing devices comprises instructions for imaging and treatment of the tissue.

Clause 27. A method of treating target tissue at a target site of a patient, said method comprising: manually inserting a probe into the patient; coupling the probe to a robotic arm; establishing an allowable range of motion for the probe, the allowable range of motion stored on a memory of one or more computing devices operably coupled with the robotic arm; treating or imaging the target tissue of the patient with the probe; and moving the robotic arm under control of the one or more computing devices operably coupled with the probe, to affect movement of the probe within the allowable range of motion for the probe.

Clause 28. The method of clause 27, wherein the probe is coupled to the robotic arm while the robotic arm is in a passive mode.

Clause 29. The method of clause 27, wherein the allowable range of motion for the probe is established while the robotic arm is in a passive mode.

Clause 30. The method of clause 27, wherein establishing the allowable range of motion for the probe comprises establishing the allowable range of motion for the probe in response to a user input.

Clause 31. The method of clause 27, wherein establishing the allowable range of motion for the probe comprises establishing the allowable range of motion for the probe in response to a position of the probe.

Clause 32. The method of clause 31, wherein the position of the probe relative to the target tissue is determined in response to one or more tissue landmarks in one or more images of the target tissue.

Clause 33. The method of clause 27, further comprising updating the allowable range of motion for the probe in real-time.

Clause 34. The method of clause 27, further comprising receiving, from a user input device operably coupled with one or more computing device, one or more user instructions for controlling movement of the robotic arm, and wherein moving the robotic arm under control of the one or more computing devices comprises moving the robotic arm in response to the one or more user instructions for controlling movement of the robotic arm.

Clause 35. The method of clause 34, wherein the user input device comprises one or more of a controller on the end of the robotic arm, a user interface on a display screen, a user interface on a console, or a controller that responds to forces on the end of the arm provided by the user to guide a probe on the robotic arm into position.

Clause 36. The method of clause 27, further comprising receiving sensor data from one or more force sensors operably coupled with the one or more computing devices configured to detect compression of a tissue of the patient with the probe.

Clause 37. The method of clause 36, wherein the one or more computing devices comprise a processor configured with instructions to interrupt the treatment in response to a detected compression of the tissue exceeding a predetermined threshold level of compression.

Clause 38. The method of clause 36, wherein the one or more force sensors are operatively coupled to the robotic arm.

Clause 39. The method of clause 38, further comprising receiving sensor data from one or more motion sensors operably coupled with the one or more computing devices and configured to detect movement of the patient, and wherein moving the robotic arm under control of the one or more computing devices comprises adjusting a position of the probe in response to the detected movement of the patient.

Clause 40. The method of clause 27, further comprising manually adjusting the robotic arm in a passive mode to manually adjust the probe to a manually set position.

Clause 41. The method of clause 40, wherein in the passive mode the probe is supported with the robotic arm and the probe comprises a plurality of sensors at an interface between the robotic arm and the probe to receive user input from a handle coupled to the plurality of sensors for the user to direct the probe.

Clause 42. The method of clause 41, wherein a handle coupled to the plurality of sensors is configured to receive user manipulations of the handle and the plurality of sensors at the interface is coupled to a processor of the one or more computing devices to manipulate the probe in response to the user manipulations of the handle.

Clause 43. The method of clause 42, wherein the plurality of sensors is configured to detect user manipulations of the handle with 6 degrees of freedom and wherein the processor is configured to move the probe with 6 degrees of freedom with motion corresponding to the 6 degrees in response to the user manipulations.

Clause 44. The method of clause 40, wherein manually adjusting the robotic arm in the passive mode to manually adjust the probe comprises manually adjusting the probe in one or more of at least one rotational axis or at least one translational axis.

Clause 45. The method of clause 44, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 46. The method of clause 45, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 47. The method of clause 40, wherein the manually set position of the probe is maintained after the robotic arm is released from manual adjustment.

Clause 48. The method of clause 47, wherein the robotic arm is configured to maintain the manually-set position with a tolerance in one or more of a rotational axis or a translational axis and optionally wherein the tolerance is within 5° for rotation about one or more of three axes and 5 mm for translation along the one or more of three axes and optionally for each of the one or more of three axis and optionally wherein a rotational tolerance is within 3° and optionally wherein a translational tolerance is within 3 mm and optionally 2 mm.

Clause 49. The method of clause 27, wherein the probe comprises an imaging probe.

Clause 50. The method of clause 47, wherein the probe comprises a treatment probe and the robotic arm comprises a first robotic arm, the method further comprising: manually inserting an imaging probe into the patient; coupling the imaging probe to a second robotic arm; and establishing an allowable range of motion for the imaging probe, the allowable range of motion stored on the memory of the one or more computing devices operably coupled with the first robotic arm and the second robotic arm.

Clause 51. The method of clause 50, wherein the imaging probe is coupled to the second robotic arm while the second robotic arm is in a passive mode.

Clause 52. The method of clause 50, wherein the allowable range of motion for the imaging probe is established while the second robotic arm is in a passive mode.

Clause 53. The method of clause 50, wherein establishing the allowable range of motion for the imaging probe comprises establishing the allowable range of motion in response to a distance or alignment between the treatment probe and the imaging probe.

Clause 54. The method of clause 50, wherein establishing the allowable range of motion for the imaging probe comprises establishing the allowable range of motion for the imaging probe in response to a user input.

Clause 55. The method of clause 50, wherein establishing the allowable range of motion for the imaging probe comprises establishing the allowable range of motion in response to a position of the imaging probe relative to the target tissue.

Clause 56. The method of clause 55, wherein the position of the imaging probe relative to the target tissue is determined in response to one or more tissue landmarks in one or more images of the target tissue.

Clause 57. The method of clause 50, further comprising updating the allowable range of motion for the imaging probe in real-time.

Clause 58. The method of clause 50, further comprising receiving, from a user input device operably coupled with one or more computing device, one or more user instructions for controlling movement of the second robotic arm, and wherein moving the second robotic arm under control of the one or more computing devices comprises moving the second robotic arm in response to the one or more user instructions for controlling movement of the second robotic arm.

Clause 59. The method of clause 58, further comprising establishing an allowable range of motion of the second robotic arm in response to the one or more user instructions for controlling movement of the second robotic arm.

Clause 60. The method of clause 50, further comprising receiving sensor data from one or more force sensors operably coupled with the one or more computing devices and configured to detect compression of a tissue of the patient with the imaging probe, and wherein moving the second robotic arm under control of the one or more computing devices comprises moving the imaging probe away from the tissue in response to a determination that the detected compression of the tissue exceeds a predetermined threshold level of compression.

Clause 61. The method of clause 60, wherein the one or more force sensors are operatively coupled to the second robotic arm.

Clause 62. The method of clause 50, further comprising receiving sensor data from one or more positions sensors operably coupled with the one or more computing devices and configured to detect one or more positions of the first robotic arm, the treatment probe, the second robotic arm, or the imaging probe.

Clause 63. The method of clause 50, further comprising receiving sensor data from one or more motion sensors operably coupled with the one or more computing devices and configured to detect movement of the patient, and wherein moving the second robotic arm under control of the one or more computing devices comprises adjusting a position of the imaging probe in response to the detected movement of the patient.

Clause 64. The method of clause 50, further comprising calibrating the first robotic arm to identify its position with respect to the second robotic arm, and calibrating the second robotic arm to identify its position with respect to the first robotic arm.

Clause 65. The method of clause 50, wherein moving the first robotic arm or the second robotic arm under control of the one or more computing devices comprises automatically adjusting movement of the first robotic arm in response to movement of the second robotic arm, or automatically adjusting movement of the second robotic arm in response to movement of the first robotic arm.

Clause 66. The method of clause 50, wherein moving the first robotic arm or the second robotic arm under control of the one or more computing devices comprises moving the first robotic arm or the second robotic arm to prevent contact between portions of the treatment probe and the imaging probe disposed outside the patient.

Clause 67. The method of clause 66, wherein moving the first robotic arm or the second robotic arm under control of the one or more computing devices comprises moving the first robotic arm or the second robotic arm to maintain an alignment between the treatment probe and the imaging probe.

Clause 68. The method of clause 67, wherein the alignment maintained between the treatment probe and the imaging probe comprises a parallel alignment between the treatment probe and the imaging probe, wherein longitudinal axes of the treatment probe and the imaging probe are parallel with one another.

Clause 69. The method of clause 67, wherein the alignment maintained between the treatment probe and the imaging probe comprises a coplanar alignment between the treatment probe and the imaging probe, wherein longitudinal axes of the treatment probe and the imaging probe are coplanar with one another.

Clause 70. The method of clause 67, wherein the alignment maintained between the treatment probe and the imaging probe comprises a non-parallel alignment between the treatment probe and the imaging probe, wherein longitudinal axes of the treatment probe and the imaging probe are transverse with one another.

Clause 71. The method of clause 50, further comprising detecting one or more of a distance or an alignment between the treatment probe and the imaging probe.

Clause 72. The method of clause 50, wherein moving the first robotic arm or the second robotic arm under control of the one or more computing devices comprises moving the first robotic arm or the second robotic arm to automatically move the treatment probe or the imaging probe along a scanning profile stored on the one or more computing devices.

Clause 73. The method of clause 72, wherein moving the first robotic arm under control of the one or more computing devices comprises moving the first robotic arm to automatically move the treatment probe over the scanning profile comprising a treatment profile.

Clause 74. The method of clause 72, wherein moving the second robotic arm under control of the one or more computing devices comprises moving the second robotic arm to automatically move the imaging probe over the scanning profile comprising an imaging profile.

Clause 75. The method of clause 74, wherein the imaging profile comprises a plurality of transverse view scans or a plurality of sagittal view scans of the target site, and wherein method further comprises generating a 3-dimensional image of the target site.

Clause 76. The method of clause 74, wherein the second robotic arm is moved to automatically move the imaging probe over the scanning profile comprising the imaging profile while the treatment probe treats the target tissue.

Clause 77. The method of clause 50, wherein imaging the target site with the imaging probe comprises imaging the target site with the imaging probe operating in Doppler mode, and wherein the method further comprises identifying regions of high blood flow in the target site based on one or more images of the target site obtained with the imaging probe.

Clause 78. The method of clause 77, further comprising applying hemostasis to identified regions of high blood flow in the target site.

Clause 79. The method of clause 77, further comprising performing biopsy of tissue located at identified regions of high blood flow in the target site.

Clause 80. The method of clause 77, further comprising identifying the regions of high blood flow as cancerous tissue.

Clause 81. The method of clause 77, wherein imaging the target site with the imaging probe comprises rotating the imaging probe.

Clause 82. The method of clause 50, wherein imaging the target site with the imaging probe comprises generating an intra-operative image of the target site.

Clause 83. The method of clause 82, further comprising mapping the intra-operative image with a pre-operative image of the target site.

Clause 84. The method of clause 83, wherein the pre-operative image of the target site comprises one or more of an X-ray image, a fluoroscopic image, a computed tomography (CT) image, an ultrasound image, or an MRI image.

Clause 85. The method of clause 83, wherein mapping the intra-operative image with the pre-operative image comprises mapping one or more anatomical regions within the intra-operative and pre-operative images with one another.

Clause 86. The method of clause 85, wherein the one or more anatomical regions comprise one or more of a bladder neck, an external sphincter, or a verumontanum.

Clause 87. A method of operating a robotic arm to image or treat target tissue at a target site of a patient, said method comprising: coupling at least one probe to at least one robotic arm; manually adjusting the at least one robotic arm in a passive mode to manually adjust the at least one probe to a manually set position; and releasing the at least one robotic arm from the passive mode; wherein the at least one robotic arm maintains the manually set position of the at least one probe after the releasing from manual adjustment; and wherein the at least one probe one or more of images or treats the target tissue at the target site of the patient from the maintained manually set position.

Clause 88. The method of clause 87, wherein the at least one probe is coupled to the at least one robotic arm prior to inserting the at least one probe into the patient.

Clause 89. The method of clause 87, wherein the at least one probe is coupled to the at least one robotic arm after inserting the at least one probe into the patient.

Clause 90. The method of clause 87, wherein the at least one robotic arm maintains the manually set position of the at least one probe with a locked configuration of the at least one robotic arm and optionally wherein sensors of the joints of the at least one robotic arm and actuators coupled to the joints of the robotic arm maintain the manually set position of the at least one robotic arm in the locked configuration.

Clause 91. The method of clause 87, wherein manually adjusting the at least one robotic arm in the passive mode comprises manually adjusting the at least one probe in one or more of at least one rotational axis or at least one translational axis.

Clause 92. The method of clause 91, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 93. The method of clause 92, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 94. The method of clause 87, wherein the at least one robotic arm maintains the manually-set position within a tolerance in one or more of a rotational axis or a translational axis and optionally wherein the tolerance is within 50 for rotation about one or more of three axes and 5 mm for translation along the one or more of three axes and optionally for each of the one or more of three axis and optionally wherein a rotational tolerance is within 30 and optionally wherein a translational tolerance is within 3 mm and optionally 2 mm.

Clause 95. The method of clause 87, wherein coupling the at least one probe to the at least one robotic arm comprises one or more of coupling a treatment probe to a first robotic arm or coupling an imaging probe to a second robotic arm.

Clause 96. The method of clause 95, wherein manually adjusting the at least one robotic arm in the passive mode comprises aligning the treatment probe and the imaging probe to one another.

Clause 97. The method of clause 96, wherein the treatment probe and the imaging probe are aligned to one another to be one or more of parallel or co-planar.

Clause 98. The method of clause 96, wherein the at least one robotic arm maintains the alignment between the imaging and treatment probes after the releasing from manual adjustment.

Clause 99. The method of clause 98, wherein the alignment between the imaging and treatment probes is maintained within a tolerance in one or more of a rotational axis or a translational axis and optionally wherein the tolerance is within 5° for rotation about one or more of three axes and 5 mm for translation along the one or more of three axes and optionally for each of the one or more of three axis and optionally wherein a rotational tolerance is within 30 and optionally wherein a translational tolerance is within 3 mm and optionally 2 mm.

Clause 100. A system comprising: a processor configured with instructions to perform the method of any one of the preceding clauses.

Clause 101. A system for operating a robotic arm to image or treat target tissue at a target site of a patient, said system comprising: at least one robotic arm coupled to at least one probe for one or more of treating or imaging the target tissue of the patient; and one or more computing devices operably coupled with the at least one robotic arm, the one or more computing devices configured to execute instructions for: operating the at least one robotic arm in a passive mode such that the at least one robotic arm can be manually adjusted to manually adjust the at least one probe to a manually set position, releasing the at least one robotic arm from the passive mode after the at least one probe has been manually adjusted to the manually set position, and maintaining the manually set position of the at least one probe after the release from manual adjustment.

Clause 102. The system of clause 101, wherein the at least one probe is configured to couple to the at least one robotic arm prior to inserting the at least one probe into the patient.

Clause 103. The system of clause 101, wherein the at least one probe is configured to couple to the at least one robotic arm after inserting the at least one probe into the patient.

Clause 104. The system of clause 101, wherein the at least one robotic arm maintains the manually set position of the at least one probe with a locked configuration of the at least one robotic arm and optionally wherein sensors of the joints of the at least one robotic arm and actuators coupled to the joints of the robotic arm maintain the manually set position of the at least one robotic arm in the locked configuration.

Clause 105. The system of clause 101, wherein the one or more computing devices are further configured to execute instructions for controlling movement of the at least one robotic arm.

Clause 106. The system of clause 101, wherein the at least one robotic arm is configured to be manually adjusted to manually adjust the at least one probe in one or more of at least one rotational axis or at least one translational axis.

Clause 107. The system of clause 106, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 108. The system of clause 107, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 109. The system of clause 106, wherein the at least one robotic arm is configured to maintain the manually-set position with a tolerance in one or more of a rotational axis or a translational axis and optionally wherein the tolerance is within 5° for rotation about one or more of three axes and 5 mm for translation along the one or more of three axes and optionally for each of the one or more of three axis and optionally wherein a rotational tolerance is within 3° and optionally wherein a translational tolerance is within 3 mm and optionally 2 mm.

Clause 110. The system of clause 101, wherein the at least one probe comprises one or more of a treatment probe or an imaging probe.

Clause 111. The system of clause 110, wherein the at least one probe comprises the treatment probe and the imaging probe, and wherein the at least one robotic arm comprises a first robotic arm coupled to the treatment probe and a second robotic arm coupled to the imaging probe.

Clause 112. The system of clause 110, wherein the at least one probe comprises the treatment probe and the imaging probe, and wherein the treatment probe and the imaging probe are configured to be manually adjusted to align the treatment probe and the imaging probe to one another.

Clause 113. The system of clause 112, wherein the treatment probe and the imaging probe are aligned to one another to be one or more of parallel or co-planar.

Clause 114. The system of clause 113, wherein the at least one robotic arm maintains the alignment between the imaging and treatment probes after the releasing from manual adjustment.

Clause 115. The system of clause 114, wherein the alignment between the imaging and treatment probes is maintained within a tolerance in one or more of a rotational axis or a translational axis.

Clause 116. A system for treating target tissue at a target site of a patient, the system comprising: a first robotic arm coupled to a treatment probe for treating the target tissue of the patient; a second robotic arm coupled to an imaging probe for imaging the target tissue of the patient; and one or more computing devices operably coupled with the first robotic arm and the second robotic arm, the one or more computing devices configured to execute instructions for controlling movement of one or more of the first robotic arm or the second robotic arm.

Clause 117. The system of clause 116, wherein the one or more computing devices are configured to execute instructions for controlling the movement of the first robotic arm or the second robotic arm to adjust one or more of a pitch, yaw, roll, or linear position of the treatment probe or the imaging probe along an axis of entry of the treatment probe or the imaging probe into the patient.

Clause 118. The system of clause 116, wherein the one or more computing devices are configured to execute instructions comprising controlling the movement of the first robotic arm or the second robotic arm to retract the treatment probe or the imaging probe, respectively along the axis of entry.

Clause 119. The system of clause 118, wherein the one or more computing devices are configured to execute instructions comprising controlling the movement of the first robotic arm or the second robotic arm to retract, but not advance, the treatment probe or the imaging probe, respectively, along the axis of entry.

Clause 120. The system of clause 116, wherein the one or more computing devices are configured to execute instructions comprising controlling the movement of the first robotic arm or the second robotic arm in response to user instructions received with a user input device operably coupled with the one or more computing devices.

Clause 121. The system of clause 116, wherein the one or more computing devices are configured to execute instructions comprising controlling the movement of the first robotic arm or the second robotic arm to move the treatment probe or the imaging probe, respectively, within an allowable range of motion for the treatment probe or the imaging probe stored in the one or more computing devices.

Clause 122. The system of clause 121, wherein the one or more computing devices are configured to execute instructions comprising establishing the allowable range of motion for the treatment probe or the imaging probe in response to a user input.

Clause 123. The system of clause 121, wherein the one or more computing devices are configured to execute instructions comprising establishing the allowable range of motion for the treatment probe or the imaging probe in response to a distance or alignment between the treatment probe and the imaging probe.

Clause 124. The system of clause 121, wherein the one or more computing devices are configured to execute instructions comprising establishing the allowable range of motion for the treatment probe or the imaging probe in response to a position of the treatment probe or the imaging probe relative to the target tissue.

Clause 125. The system of clause 124, wherein the one or more computing devices are configured to execute instructions comprising detecting the position of the treatment probe or the imaging probe relative to the target tissue based on one or more images of the target tissue, the one or more images comprising one or more tissue landmarks.

Clause 126. The system of clause 121, wherein the one or more computing devices are configured to execute instructions for updating the allowable range of motion for the treatment probe or the imaging probe in real-time.

Clause 127. The system of clause 116, wherein the one or more computing devices are configured to execute instructions comprising controlling the movement of the first robotic arm or the second robotic arm to maintain an alignment between the treatment probe and the imaging probe and optionally wherein the alignment maintains the treatment probe within a field of view of the imaging probe.

Clause 128. The system of clause 127, wherein the alignment maintained between the treatment probe and the imaging probe comprises a substantially parallel alignment between the treatment probe and the imaging probe, wherein longitudinal axes of the treatment probe and the imaging probe are substantially parallel with one another.

Clause 129. The system of clause 127, wherein the alignment maintained between the treatment probe and the imaging probe comprises a co-planar alignment between the treatment probe and the imaging probe, wherein longitudinal axes of the treatment probe and the imaging probe are co-planar with one another.

Clause 130. The system of clause 127, wherein the alignment maintained between the treatment probe and the imaging probe comprises a non-parallel alignment between the treatment probe and the imaging probe, wherein longitudinal axes of the treatment probe and the imaging probe are transverse with one another.

Clause 131. The system of clause 116, wherein the one or more computing devices are configured to execute instructions comprising detecting one or more of a distance or an alignment between the treatment probe and the imaging probe.

Clause 132. The system of clause 116, wherein the one or more computing devices are configured to execute instructions comprising controlling the movement of the first robotic arm or the second robotic arm to prevent contact between portions of the treatment probe and the imaging probe disposed outside the patient.

Clause 133. The system of clause 116, wherein the one or more computing devices are configured to execute instructions for automatically adjusting movement of the first robotic arm in response to movement of the second robotic arm.

Clause 134. The system of clause 116, wherein the one or more computing devices are configured to execute instructions for automatically adjusting movement of the second robotic arm in response to a position of the first robotic arm and optionally wherein the second robotic arm moves the imaging probe in response to the position of the treatment probe to maintain the treatment probe within a field of view of the imaging probe.

Clause 135. The system of clause 116, wherein the one or more computing devices are configured to execute instructions for controlling the movement of the first robotic arm or the second robotic arm to automatically move the treatment probe or the imaging probe along a scanning profile stored on the one or more computing devices.

Clause 136. The system of clause 135, wherein the one or more computing devices are configured to execute instructions for controlling the movement of the first robotic arm to automatically move the treatment probe along the scanning profile comprising a treatment profile.

Clause 137. The system of clause 135, wherein the one or more computing devices are configured to execute instructions for controlling the movement of the second robotic arm to automatically move the imaging probe along the scanning profile comprising an imaging profile.

Clause 138. The system of clause 137, wherein the imaging profile comprises a plurality of transverse view scans or a plurality of sagittal view scans of the target site, and wherein the one or more computing devices are further configured to execute instructions comprising generating a 3-dimensional image of the target site.

Clause 139. The system of clause 137, wherein the one or more computing devices are configured to execute the instructions to automatically move the imaging probe along the scanning profile comprising the imaging profile while the treatment probe treats the target tissue.

Clause 140. The system of clause 116, wherein the one or more computing devices are configured to execute instructions comprising controlling the movement of the first robotic arm or the second robotic arm in response to sensor data received from one or more sensors operably coupled with the one or more computing devices.

Clause 141. The system of clause 140, wherein the one or more sensors are operatively coupled to one or more of the first or second robotic arm.

Clause 142. The system of clause 140, wherein the one or more sensors comprise one or more position sensors coupled to one or more of the first robotic arm, the treatment probe, the second robotic arm, or the imaging probe.

Clause 143. The system of clause 140, wherein the one or more sensors comprise one or more force sensors configured to detect compression of a tissue of the patient with the treatment probe or the imaging probe, and wherein the one or more computing devices are configured to execute instructions comprising moving the treatment probe or the imaging probe away from the tissue in response to a determination that the detected compression of the tissue exceeds a predetermined threshold level of compression.

Clause 144. The system of clause 140, wherein the one or more sensors comprise one or more motion sensors configured to detect movement of the patient, and wherein the one or more computing devices are configured to execute instructions comprising adjusting a position of the treatment probe or the imaging probe in response to the detected movement of the patient.

Clause 145. The system of clause 116, wherein each of the first robotic arm and the second robotic arm comprises a plurality of joints operably coupled with a plurality of actuators, wherein the plurality of actuators are operably coupled with the one or more computing devices, and wherein the instructions for controlling the movement of the first robotic arm or the second robotic arm comprise instructions for controlling actuation of one or more of the plurality of actuators.

Clause 146. The system of clause 116, further comprising a mobile base coupled to the first robotic arm and the second robotic arm.

Clause 147. The system of clause 146, wherein the mobile base comprises one or more user input devices operably coupled with the one or more computing devices and configured to receive user instructions for controlling the movement of one or more of the first robotic arm or the second robotic arm.

Clause 148. The system of clause 146, wherein the mobile base comprises the one or more computing devices configured to execute instructions for controlling the movement of one or more of the first robotic arm or the second robotic arm.

Clause 149. The system of clause 116, wherein the one or more computing devices are operably coupled with one or more of the treatment probe or the imaging probe, and wherein the one or more computing devices are further configured to execute instructions for controlling one or more of treatment with the treatment probe or imaging with the imaging probe.

Clause 150. The system of clause 116, wherein the one or more computing devices are further configured to execute instructions comprising displaying, on a display operably coupled with the one or more computing devices, one or more images of the target site obtained with imaging probe.

Clause 151. The system of clause 116, wherein the first robotic arm or the second robotic arm comprises a coupling structure configured to couple magnetically to the treatment probe or the imaging probe, respectively.

Clause 152. The system of clause 116, wherein the first robotic arm or the second robotic arm comprises a coupling structure configured to removably couple to the treatment probe or the imaging probe, respectively, with a quick-release mechanism configured to uncouple the first robotic arm or the second robotic arm from the treatment probe or the imaging probe, respectively, when an error is detected in an operation of the first robotic arm or the second robotic arm.

Clause 153. The system of clause 116, further comprising a common arm, wherein the first robotic arm is operatively coupled to the common arm at a first location and the second robotic arm is operatively coupled to the common arm at a second location.

Clause 154. The system of clause 153, further comprising a mobile base operatively coupled to the common arm.

Clause 155. The system of clause 116, wherein the imaging probe comprises an ultrasound transducer configured to capture an ultrasound image of the target tissue.

Clause 156. The system of clause 155, wherein the ultrasound transducer is configured to be operated in Doppler mode such that regions of high blood flow in the target site are identifiable.

Clause 157. The system of clause 116, wherein the one or more computing devices are configured to execute instructions for operating the first robotic arm in a passive mode in which the first robotic arm is configured to be manually adjusted to position the treatment probe to a manually-set position.

Clause 158. The system of clause 157, wherein when the first robotic arm is in the passive mode, the treatment probe is configured to be manually adjusted in one or more of at least one rotational axis or at least one translational axis.

Clause 159. The system of clause 158, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 160. The system of clause 159, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 161. The system of clause 157, wherein the one or more computing devices are configured to execute instructions for maintaining the manually-set position of the treatment probe after the first robotic arm is released from manual adjustment.

Clause 162. The system of clause 161, wherein the first robotic arm is configured to maintain the manually set position with a tolerance in one or more of a rotational axis or a translational axis.

Clause 163. The system of clause 116, wherein the one or more computing devices are configured to execute instructions for operating the second robotic arm in a passive mode in which the second robotic arm is configured to be manually adjusted to position the imaging probe to a manually-set position.

Clause 164. The system of clause 163, wherein when the second robotic arm is in the passive mode, the imaging probe is configured to be manually adjusted in one or more of at least one rotational axis or at least one translational axis.

Clause 165. The system of clause 164, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

Clause 166. The system of clause 165, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

Clause 167. The system of clause 163, wherein the one or more computing devices are configured to execute instructions for maintaining the manually-set position of the imaging probe after the second robotic arm is released from manual adjustment.

Clause 168. The system of clause 167, wherein the second robotic arm is configured to maintain the manually-set position with one or more of a tolerance a tolerance in one or more of a rotational axis or a translational axis.

Clause 169. A system for treating a patient, the system comprising: a probe; a coupling structure to receive the probe; a support to receive the patient; an arm coupled to the support; a first slider coupled to the arm to translate in a first direction; a second slider coupled to the first slider, the arm and the support to translate in a second direction transverse to the first direction; and an adjustable extension between the second slider and the coupling structure, the adjustable extension comprising an extension joint configured to extend and retract in a third direction transverse to the first direction and the second direction; wherein the coupling structure is supported with the arm, the first slider, the second slider and the extension to allow the coupling structure to move within a three-dimensional volume.

Clause 170. The system of clause 169, further comprising a pivot coupled to the arm and the coupling structure between the coupling structure and the extension joint, the pivot configured to rotate the coupling structure up and down relative to the patient and optionally wherein a pivot axis of rotation extends in a substantially horizontal direction and optionally wherein substantially horizontal comprises an angle within about 10 degrees of horizontal.

Clause 171. The system of clause 170, further comprising a turret coupled to the arm and the coupling structure between the coupling structure and the extension joint, the turret configured to allow rotation of the coupling structure about an axis of rotation and optionally wherein an axis of rotation of the turret is within about 10 degrees of vertical and optionally wherein the turret is coupled to the coupling structure and the arm between the coupling structure and the pivot.

Clause 172. The system of clause 171, wherein each of the first slider, the second slider, the extension joint, the turret and the pivot comprises a brake to lock a position of the first slider, the second slider, the extension joint, the turret and the pivot to maintain a position and orientation of the probe when the probe has been inserted into the patient and coupled to the arm with coupling structure.

Clause 173. The system of clause 171, further comprising a processor controlled actuator coupled to one or more of the first slider, the second slider, the extension joint, the turret or the pivot to move the coupling structure toward a coupling structure of the probe when the probe has been inserted into the patient.

Clause 174. The system of clause 173, further comprising a linkage coupled to a processor to control one or more of a position or orientation of the coupling structure and wherein the linkage comprises one or more of the first slider, the second slider, the extension joint, the turret and the pivot coupled to a corresponding actuator.

Clause 175. The system of clause 171, further comprising a second coupling structure to couple to a second probe and optionally wherein the second coupling structure is configured to support the second probe above the probe.

Clause 176. The system of clause 171, further comprising a second coupling structure to couple to a second probe, the second coupling structure coupled to a second extension joint, a second turret and a second pivot, the second coupling structure, the second extension joint, the second turret and the second pivot supported with the arm to support the second probe.

Clause 177. The system of clause 169, wherein the first direction is perpendicular to the second direction.

Clause 178. The system of any one of the preceding clauses, wherein the coupling structure of the probe comprises one or more of a protrusion or a groove on a lower surface of the probe and the coupling structure supported with the arm comprises one or more of a protrusion or a groove on an upper surface of the coupling surface to couple the coupling structure of the probe to the coupling structure supported with the arm.

Clause 179. A mounting assembly for coupling to a patient support, comprising: a first clamp to affix to a first rail on a first side of the patient support; a first arm having a first end and a second end, the first end pivotally connected to the first clamp; a second clamp to affix to a second rail on a second side of the patient support; and a second arm having a first end and a second end, the first end pivotally connected to the second clamp; wherein an elongate support extends between the first arm and the second arm to support a probe to be inserted into the patient.

Clause 180. The mounting assembly of clause 179, wherein first arm and the second arm are each pivotally connected to the elongate support to accommodate a variation in distance between the first rail and the second rail.

Clause 181. The mounting assembly of clause 180, wherein the first rail is substantially parallel to the second rail and the first arm and the second arm are pivotally connected to the first clamp and the second clamp, respectively to allow the first and second clamps to engage the first rail and the second rail in a substantially parallel configuration.

Clause 182. The mounting assembly of clause 179, further comprising: a first coupler to pivotally connect to the first clamp and first arm, the first coupler configured to releasably couple to the first end of the first arm; and a second coupler to pivotally connect the second clamp and second arm, the second coupler configured to releasably couple to the first end of the second arm.

Clause 183. The mounting assembly of clause 182, wherein the first coupler and the second coupler each has a longitudinal axis to receive the first end of the arm and a pivot axis that is transverse to the longitudinal axis.

Clause 184. The mounting assembly of clause 183, wherein the first coupler defines a first hollow cavity configured to accept the first end of the first arm and wherein the second coupler defines a second hollow cavity configured to accept the first end of the second arm.

Clause 185. The mounting assembly of clause 179, wherein the first clamp and the second clamp each comprises a first jaw and a second jaw configured for relative movement therebetween to securely-connect to the rail.

Clause 186. The mounting assembly of clause 185, wherein the first jaw is moveable toward the second jaw with a lever.

Clause 187. The mounting assembly of clause 179, wherein the first rail and the second rail comprise portions of one or more rails of the patient support and optionally wherein the patient support comprises a bed.

Clause 188. The mounting assembly of clause 179, wherein the first arm is configured to pivot relative to the first clamp and the second arm is configured to pivot relative to the second clamp to accommodate variable spacing between the first rail on a first side of the patient support and the second rail on a second side of the patient support.

Clause 189. The mounting assembly of clause 179, wherein mounting assembly is configured to limit movement of the elongate support relative to the first rail and the second rail to no more than 5 mm in response to a 150 kg load to the elongate support and optionally wherein the movement is no more than 3 mm in response to a 100 kg load to the elongate support.

Clause 190. The mounting assembly of clause 179, wherein the elongate support, the first clamp, the first arm, the second clamp and second arm are configured in order to limit movement of the elongate support to no more than 5 mm in response to a 150 kg load to the elongate support and optionally wherein the movement is no more than 3 mm in response to a 100 kg load to the elongate support.

Clause 191. The mounting assembly of clause 190, wherein the probe to be inserted into the patient comprises a distance within a range from about 20 cm to about 60 cm, and wherein the mounting assembly is configured to move a distal end of the probe no more than 6 mm in response to the load to the elongate support.

Clause 192. The mounting assembly of clause 179, further comprising a robotic arm attached to the elongate support.

Clause 193. The mounting assembly of clause 192, wherein the probe is connected to the robotic arm.

Clause 194. The mounting assembly of clause 193, wherein the probe comprises one or more of a treatment probe or an imaging probe.

Clause 195. The mounting assembly of clause 194, wherein the robotic arm comprises a first robotic arm and a second robotic arm attached to the elongate support.

Clause 196. The mounting assembly of clause 195, wherein the treatment probe is coupled to the first robotic arm and the imaging probe is coupled to the second robotic arm.

Clause 197. The mounting assembly of clause 196, wherein the treatment probe and the imaging probe are aligned with one another to be substantially co-planar.

Clause 198. The mounting assembly of clause 179, further comprising one or more extendable legs connected to one or more of the elongate support, the first arm, the second arm, the first clamp, or the second clamp and extending downwardly therefrom to engage a floor surface.

Clause 199. The mounting assembly of clause 179, further comprising an extendable leg connected to the elongate support and extending downwardly therefrom to engage a floor surface.

Clause 200. The mounting assembly of clause 179, further comprising a first extendable leg connected to the first clamp and extending downwardly therefrom to engage a floor surface and a second extendable leg connected to the second clamp and extending downwardly therefrom to engage a floor surface.

Clause 201. The mounting assembly of clause 179, further comprising a third clamp to engage the first rail and a fourth clamp to engage the second rail, the first clamp coupled to the third clamp with a first brace extending therebetween to distribute a first load along the first rail, the second clamp coupled to the fourth clamp with a second brace extending therebetween to distribute a first load along the second rail.

Clause 202. The mounting assembly of clause 179, wherein the elongate support comprises a crossbar extending between the first arm and the second arm.

Clause 203. A system for treating target tissue at a target site of a patient, the system comprising: the mounting assembly of any one of clauses 179 to 198; a first robotic arm coupled to the elongate support; a treatment probe coupled to the first robotic arm; a second robotic arm coupled to the elongate support; and an imaging probe coupled to the second robotic arm.

Clause 204. A system as in clause 203, wherein the treatment probe is coupled to a linkage configured to translate the treatment probe along an elongate axis and to rotate the treatment probe about the elongate axis while an end of the first robotic arm remains stationary and wherein the imaging probe is coupled to a linkage to translate the imaging probe along an elongate axis of the imaging probe while an end of the second robotic arm remains stationary.

Clause 205. A system as in clause 203, wherein the first robotic arm comprises a first plurality of joints to translate and rotate the treatment probe and wherein the second robotic arm comprises a second plurality of joints to translate and rotate the treatment probe.

Clause 206. A system as in clause 203, wherein each of the robotic arms comprises from 5 to 7 degrees of freedom.

Clause 207. A system to treat a patient comprising: a robotic arm; a probe to couple to the robotic arm, the probe sized and shaped for insertion into the patient; a plurality of sensors coupled to the robotic arm to indicate a relative position and orientation of the probe in relation to the robotic arm with the probe decoupled from the robotic arm; and a processor operatively coupled to the robotic arm and the plurality of sensors, the processor configured with instructions to move the robotic arm into an engagement position and orientation to engage the probe with the robotic arm.

Clause 208. The system of clause 207, wherein the processor is configured with instructions to seek the probe with the robotic arm and to engage the probe with the robotic arm.

Clause 209. The system of clause 208, wherein the processor is configured with instructions to seek the probe with the robotic arm while a user holds the probe steady with the probe inserted into the patient and optionally wherein a gap extends between the probe and the robotic arm prior to seeking the probe and wherein a distal end portion of the robotic arm contacts the probe to engage the probe.

Clause 210. The system of clause 207, wherein the robotic arm comprises an engagement structure to engage the probe and the probe comprises an engagement structure to engage the robotic arm with the engagement position and orientation.

Clause 211. The system of clause 210, wherein the processor is configured with instructions to move the robotic arm into an orientation corresponding to the engagement orientation prior to contacting the probe and to translate the robotic arm onto the probe with the in the engagement orientation.

Clause 212. The system of clause 207, wherein the plurality of sensors comprises a coarse sensor for the robotic arm to sense the probe at a far distance and a proximity sensor and optionally wherein the plurality of sensors is located on the robotic arm.

Clause 213. The system of clause 212, wherein the coarse sensor comprises an infrared transmitter and a beacon.

Clause 214. The system of clause 212, wherein the coarse sensor comprises an infrared transmitter and a beacon.

Clause 215. The system of clause 207, wherein the plurality of sensors comprises a sensor array coupled to the robotic arm and one or more fiducials on the probe to determine a position and an orientation of the probe in relation to the robotic arm.

Clause 216. The system of clause 207, wherein the plurality of sensors is oriented toward the probe when the probe has engaged the robotic arm.

Clause 217. A system to treat a patient comprising: a robotic arm; a probe to couple to the robotic arm, the probe sized and shaped for insertion into the patient; a plurality of sensors coupled to the probe between an engagement structure to couple robotic arm and a distal end of the probe; and a processor operatively coupled to the robotic arm and the plurality of sensors, the processor configured with instructions to move the robotic arm in response to user input detected from the plurality of sensors.

Clause 218. The system of clause 217, wherein the processor is configured with instructions to establish a zero gravity-mode with the probe on the robotic arm in a free-standing configuration prior to inserting the probe into the patient and wherein the zero gravity mode is configured to drive joints of the robotic arm with forces to substantially counteract the weight of the robotic arm with the probe coupled on the arm.

Clause 219. The system of clause 217, wherein the user input comprises strain detected with the plurality of sensors and wherein the strain comprises strain related to deflection of the probe between the distal end and the engagement structure.

Clause 220. The system of clause 217, wherein the probe comprises an elongate probe sized and shaped for insertion into the patient.

Clause 221. The system of clause 220, wherein the probe comprises an elongate portion for the user to grasp between the plurality of sensors and the distal end of the probe, and wherein a resistance of tissue to insertion of the probe pushes opposite an insertion force from a hand of the user so as to decrease input to the plurality of sensors and decrease advancement of the probe into the patient.

Clause 222. The system of clause 221, wherein the resistance of the tissue to insertion is perceived by the user with the deceased advancement of the probe.

Clause 223. The system of clause 217, wherein the plurality of sensors and the probe are arranged to provide haptic feedback to the user when the probe encounters a resistance to movement.

Clause 224. The system of clause 217, wherein the robotic arm comprises a plurality of joints and a plurality of internal joint sensors and wherein the processor is configured to implement a passive mode of the probe to allow the user to insert the probe into the patient and wherein the processor is configured to provide reactive forces to the plurality of internal joints to stabilize the arm in the passive mode.

Clause 225. The system of clause 217, wherein one or more of the probe or the distal portion of the robotic arm comprises an inertial measurement unit ("IMU") to detect movement of the probe and optionally wherein the processor is configured to receive output from the IMU to determine the position and orientation of the probe.

Clause 226. The system of clause 225, wherein the probe is configured to mount on the arm with a predefined position and orientation relative to the IMU in order to determine the position and orientation of the probe in response to the position and orientation of the IMU and optionally wherein the IMU is coupled to the arm with a predefined position and orientation in relation to a distal end of the arm.

Clause 227. The system of clause 225, wherein the processor is configured to receive the output from the IMU and the output from the plurality of sensors to determine one or more of a position or an orientation to move the probe.

Clause 228. The system of clause 225, wherein the probe is configured for the user to grasp the probe and the sensors and the processor are configured to determine the user input in response to the user grasping the probe.

Clause 229. A system to treat a patient, the system comprising: a sheath sized and shaped for insertion into the patient, the sheath comprising an elongate axis; an arm coupled to the sheath; a treatment probe comprising an energy source, the treatment probe comprising an elongate axis, the treatment probe sized and shaped for insertion into a lumen of the sheath; and a robotic arm coupled to the treatment probe, wherein the robotic arm is configured to align the elongate axis of the treatment probe with the elongate axis of the sheath and to advance the treatment probe into the sheath.

Clause 230. The system of clause 229, wherein the robotic arm coupled to the treatment probe is configured to align the axis of the treatment probe with the axis of the sheath prior to advancing the treatment probe into the sheath.

Clause 231. The system of clause 229, wherein the robotic arm comprises a sensor to determine an orientation of the treatment probe and optionally wherein the sensor comprises one or more of an accelerometer, a gyroscope, or an inertial measurement unit.

Clause 232. The system of clause 229, wherein the arm coupled to sheath comprises a sensor to determine an orientation of the sheath and optionally wherein the sensor comprises one or more of an accelerometer, a gyroscope, or an inertial measurement unit.

Clause 233. The system of clause 229, wherein the arm coupled to the sheath comprises a robotic arm.

Clause 234. The system of clause 229, wherein the sheath comprises a proximal opening to receive the treatment probe and a distal opening and wherein the treatment probe comprises a length sufficient to extend to at least the distal opening.

Clause 235. The system of clause 234, wherein the treatment probe is dimensioned for the energy source to extend to at least the distal opening when the treatment probe has been advanced into the sheath.

Clause 236. The system of clause 235, wherein the energy source extends to at least the distal opening with a gap between an end portion of the robotic arm and the sheath.

Clause 237. The system of clause 229, wherein the sheath comprises a stiff sheath.

Clause 238. The system of clause 229, wherein the sheath comprises an irrigation lumen coupled to one or more openings to provide an irrigation fluid through the one or more openings.

Clause 239. The system of clause 229, wherein the sheath comprises an aspiration channel extending to an opening in the lumen to aspirate resected tissue from the lumen.

Clause 240. The system of clause 229, wherein the lumen of the sheath is sized to receive the treatment probe, an endoscopic camera and an aspiration lumen and an irrigation lumen.

Clause 241. The system of clause 240, wherein the aspiration lumen extends to an opening to aspirate tissue resection products.

Clause 242. The system of clause 240, wherein the irrigation lumen extends to an opening to irrigate a treatment site.

Clause 243. The system of clause 240, wherein the aspiration lumen and the irrigation lumen comprise lumens of a dual lumen tube.

Clause 244. The system of clause 229, wherein the treatment probe comprises a stiff portion to advance into the sheath.

Clause 245. The system of clause 229, wherein the treatment probe comprises a flexible portion to advance into the sheath.

Clause 246. The system of clause 229, wherein the treatment probe is configured to rotate and translate the energy source.

Clause 247. The system of clause 246, wherein the energy source comprises one or more of a laser beam, a water jet, an electrode, or an ultrasound transducer.

Clause 248. The system of clause 246, wherein the robotic arm is configured to rotate the energy source.

Clause 249. The system of clause 246, wherein the treatment probe is coupled to a linkage placed on the robotic arm to rotate the treatment probe.

Clause 250. The system of clause 249, wherein the linkage is configured to translate the treatment probe.

Clause 251. The system of clause 240, wherein the endoscopic camera comprises a lens and a sensor array configured to view the treatment probe when advanced into the sheath.

Clause 252. The system of clause 251, wherein the endoscopic camera is coupled to a linkage to advance and retract the endoscopic camera.

Clause 253. The system of clause 252, wherein the linkage is coupled to the robotic arm.

Clause 254. The system of clause 252, wherein the endoscopic camera comprises a flexible extension configured to couple to the linkage with sufficient column strength to advance and retract the endoscopic camera within the lumen.

Clause 255. The system of clause 252, wherein the endoscopic camera comprises a stiff extension configured to couple to the linkage.

Clause 256. The system of clause 229, further comprising an arm coupled to an ultrasound probe.

Clause 257. The system of clause 256, wherein the arm coupled to the ultrasound probe comprises a robotic arm.

Clause 258. The system of clause 257, wherein the robotic arm coupled to the ultrasound probe is configured to position a field of view of the ultrasound probe to image the treatment probe.

Clause 259. The system of clause 258, wherein the robotic arm coupled to the ultrasound probe is configured to move the ultrasound probe in response to a position of the treatment probe.

Clause 260. The system of clause 256, wherein the ultrasound probe comprises a trans-rectal ultrasound (TRUS) probe.

Clause 261. The system of clause 256, wherein the ultrasound probe comprises a linkage to translate and rotate the ultrasound probe to position the treatment probe within a field of view of the ultrasound probe.

Clause 262. The system of clause 229, further comprising a coupling assembly configured to couple to an end portion of the robotic arm, the coupling assembly configured to couple the treatment probe to the robotic arm.

Clause 263. The system of clause 262, wherein the coupling assembly is configured to couple to the end portion of the robotic arm with an orientation in relation to the end portion of the robotic arm in order to establish an orientation of the treatment probe with respect to the end portion of the robotic arm and optionally wherein the orientation of the coupling assembly in relation to the end portion comprises a predetermined orientation.

Clause 264. The system of clause 263, wherein the coupling assembly comprises engagement structures to couple to the end of the robotic arm and wherein the robotic arm comprises corresponding engagement structures.

Clause 265. The system of clause 262, wherein the coupling assembly is configured to rotate the treatment probe while the end portion of the robotic arm remains stationary.

Clause 266. The system of clause 265, wherein the coupling assembly is configured to translate the treatment probe while the end portion of the robotic arm remains stationary.

Clause 267. The system of clause 266, wherein coupling assembly is configured to translate an endoscopic camera while the end portion of the robotic assembly remains stationary.

Clause 268. The system of clause 266, wherein coupling assembly is configured to translate a distal opening of an irrigation lumen while the end portion of the robotic assembly remains stationary.

Clause 269. The system of clause 266, wherein coupling assembly is configured to translate a distal opening of an aspiration lumen while the end portion of the robotic assembly remains stationary.

Clause 270. The system of clause 262, wherein the coupling assembly is configured to translate the treatment probe, an endoscopic camera, an irrigation lumen, and an aspiration lumen together.

Clause 271. The system of clause 262, wherein the coupling assembly is configured to translate the treatment probe, an endoscopic camera, an irrigation lumen, and an aspiration lumen independently.

Clause 272. The system of clause 229, further comprising a processor coupled to the robotic arm.

Clause 273. The system of clause 272, wherein the processor configured with instructions to advance the treatment probe into the sheath.

Clause 274. The system of clause 272, wherein the processor is configured to align the elongate axis of the treatment probe with the elongate axis of the sheath.

Clause 275. The system of clause 274, wherein the processor is configured with instructions to receive an input indicating that the elongate axis of the treatment probe has been aligned with the elongate axis of the sheath and to advance the treatment probe along the elongate axis of the sheath in response to the input.

Clause 276. The system of clause 272, wherein the processor is configured to determine an orientation of the stiff sheath and wherein the processor is configured with instructions to orient the treatment probe with the orientation of the sheath.

Clause 277. The system of clause 276, wherein the arm coupled to the sheath comprises a sensor to determine an orientation of the sheath.

Clause 278. The system of clause 276, wherein the processor is configured to determine the orientation of the sheath from joint states of the arm coupled to the sheath.

Clause 279. The system of clause 276, wherein the robotic arm comprises a sensor to determine an orientation of the treatment probe.

Clause 280. A coupling assembly configured to an end portion of the robotic arm, the coupling assembly comprising: a structure to receive a treatment probe; and an engagement structure to couple to an end portion of a robotic arm to establish an orientation of the treatment probe with respect to the end portion of the robotic arm.

Clause 281. The coupling assembly of clause 280, wherein the orientation of the coupling assembly in relation to the end portion comprises a predetermined orientation to establish a predetermined orientation of the probe with respect to the end portion of the robotic arm.

Clause 282. The coupling assembly of clause 280, wherein the robotic arm comprises corresponding engagement structures.

Clause 283. The coupling assembly of clause 280, wherein the coupling assembly is configured to rotate the treatment probe while the end portion of the robotic arm remains stationary.

Clause 284. The coupling assembly of clause 283, wherein the coupling assembly is configured to translate the treatment probe while the end portion of the robotic arm remains stationary.

Clause 285. The coupling assembly of clause 280, wherein coupling assembly is configured to translate an endoscopic camera while the end portion of the robotic assembly remains stationary.

Clause 286. The coupling assembly of clause 280, wherein coupling assembly is configured to translate a distal opening of an irrigation lumen while the end portion of the robotic assembly remains stationary.

Clause 287. The coupling assembly of clause 280, wherein coupling assembly is configured to translate a distal opening of an aspiration lumen while the end portion of the robotic assembly remains stationary.

Clause 288. The coupling assembly of clause 280, wherein the coupling assembly is configured to translate the treatment probe, an endoscopic camera, an irrigation lumen, and an aspiration lumen together while the end portion of the robotic arm remains stationary.

Clause 289. The coupling assembly of clause 280, wherein the coupling assembly is configured to translate the treatment probe, an endoscopic camera, an irrigation lumen, and an aspiration lumen independently while the end portion of the robotic arm remains stationary.

Clause 290. The coupling assembly of clause 280, wherein the coupling assembly comprises one or more linkages to move the treatment probe, an endoscopic camera, an irrigation lumen, or an aspiration lumen together while the end portion of the robotic arm remains stationary.

Clause 291. A method of treating a patient, the method comprising: aligning an elongate axis of the treatment probe with an elongate axis of the sheath; receiving an input indicating that the elongate axis of the treatment probe has been aligned with an elongate axis of the sheath; and advancing the treatment probe along the elongate axis of the sheath in response to the input.

Clause 292. A system or method as in any one of the preceding clauses, wherein the passive mode comprises a zero-gravity mode.

Clause 293. A system or method as in any one of the preceding clauses, further comprising a sensor coupled to a clamp, the clamp configured to couple to a rail, the sensor configured to measure loading of one or more of the clamp, the rail, or support coupled to a robotic arm.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system of treating or imaging a target tissue of a patient, said system comprising:
   a probe sized for insertion into the patient;
   a robotic arm configured to couple to the probe;
   one or more computing devices operatively coupled to the robotic arm and configured with instructions for:
      receiving an angular range of motion and a fulcrum location generated by a user manually manipulating the probe with the angular range of motion about the fulcrum location with the probe inserted into the patient while the robotic arm is in a passive mode;
      establishing a restriction on an allowable range of motion for the probe, the restriction comprising the fulcrum location and the angular range of motion about the fulcrum location with the probe inserted into the patient wherein the restriction is stored on a memory of the one or more computing devices;
      treating or imaging the target tissue of the patient with the probe; and
      moving the robotic arm to affect movement of the probe within the allowable range of motion of the probe.

2. The system of claim 1, wherein the probe is configured to couple to the robotic arm while the robotic arm is in the passive mode.

3. The system of claim 1, wherein establishing the fulcrum location and the allowable angular range of motion about the fulcrum location for the probe comprises establishing the allowable range of motion for the probe in response to a position of the probe.

4. The system of claim 3, wherein the position of the probe relative to the target tissue is determined in response to one or more tissue landmarks in one or more images of the target tissue.

5. The system of claim 1, further comprising updating the fulcrum location and the allowable angular range of motion about the fulcrum location for the probe in real-time.

6. The system of claim 1, further comprising a user input device operably coupled with the one or more computing devices to provide one or more user instructions for controlling movement of the robotic arm, and wherein moving the robotic arm under control of the one or more computing devices comprises moving the robotic arm in response to the one or more user instructions for controlling movement of the robotic arm.

7. The system of claim 6, wherein the user input device comprises one or more of a controller near the end of the robotic arm, a user interface on a display screen, a user interface on a console, or a controller that responds to forces on the end of the arm provided by the user to guide the probe on the robotic arm into position.

8. The system of claim 1, further comprising one or more force sensors operably coupled with the probe and the one or more computing devices to detect compression of a tissue of the patient with the probe.

9. The system of claim 8, wherein the one or more computing devices comprise a processor configured with instructions to interrupt a treatment in response to a detected compression of the tissue exceeding a predetermined threshold level of compression.

10. The system of claim 8, wherein the one or more force sensors are operatively coupled to the robotic arm.

11. The system of claim 10, further comprising one or more motion sensors operably coupled with the probe and the one or more computing devices to detect movement of the patient, and wherein the one or more computing devices are configured to adjust a position of the probe in response to the detected movement of the patient.

12. The system of claim 1, wherein in the passive mode the probe is supported with the robotic arm and the probe comprises a plurality of sensors at an interface between the robotic arm and the probe to receive user input from a handle coupled to the plurality of sensors for the user to direct the probe.

13. The system of claim 12, wherein the handle coupled to the plurality of sensors is configured to receive user manipulations of the handle and the plurality of sensors at the interface is coupled to a processor of the one or more computing devices to manipulate the probe in response to the user manipulations of the handle.

14. The system of claim 13, wherein the plurality of sensors is configured to detect user manipulations of the handle with 6 degrees of freedom and wherein the processor is configured to move the probe with 6 degrees of freedom with motion corresponding to the 6 degrees in response to the user manipulations.

15. The system of claim 1, wherein to manually manipulate in the passive mode comprises manually adjusting the probe in one or more of at least one rotational axis or at least one translational axis.

16. The system of claim 15, wherein the at least one rotation axis comprises a first rotational axis, a second rotational axis orthogonal to the first rotational axis, and a third rotational axis orthogonal to the first and second rotational axes, and wherein the at least one translational axis comprises a first translational axis, a second translational axis orthogonal to the first translational axis, and a third translational axis orthogonal to the first and second translational axes.

17. The system of claim 16, wherein the first rotational axis comprises a pitch axis, the second rotational axis comprises a yaw axis, the third rotational axis comprises a roll axis, the first translational axis comprises an X-axis, the second translational axis comprises a Y-axis, and the third translational axis comprises a Z-axis.

* * * * *